United States Patent
Ford et al.

(10) Patent No.: US 12,054,720 B2
(45) Date of Patent: Aug. 6, 2024

(54) COMPOSITIONS AND METHODS FOR USE IN CONTROLLING MOSQUITO-BORNE VIRUSES

(71) Applicant: The Penn State Research Foundation, University Park, PA (US)

(72) Inventors: Suzanne Ford, State College, PA (US); Elizabeth McGraw, State College, PA (US)

(73) Assignee: The Penn State Research Foundation, University park, PA (US)

( * ) Notice: Subject to any disclaimer, the term of this patent is extended or adjusted under 35 U.S.C. 154(b) by 733 days.

(21) Appl. No.: 17/272,269

(22) PCT Filed: Aug. 29, 2019

(86) PCT No.: PCT/US2019/048857
§ 371 (c)(1),
(2) Date: Feb. 26, 2021

(87) PCT Pub. No.: WO2020/047284
PCT Pub. Date: Mar. 5, 2020

(65) Prior Publication Data
US 2021/0171959 A1 Jun. 10, 2021

Related U.S. Application Data

(60) Provisional application No. 62/724,468, filed on Aug. 29, 2018.

(51) Int. Cl.
*C12N 15/113* (2010.01)
*A61K 31/713* (2006.01)

(52) U.S. Cl.
CPC ........ *C12N 15/1138* (2013.01); *A61K 31/713* (2013.01); *C12N 15/1137* (2013.01); *C12N 2310/14* (2013.01); *C12N 2320/31* (2013.01); *C12Y 302/01024* (2013.01)

(58) Field of Classification Search
CPC .............. C12N 15/1138; C12N 5/1137; C12N 2310/14; C12N 2320/31; A61K 31/713; C12Y 302/01024
See application file for complete search history.

(56) References Cited

U.S. PATENT DOCUMENTS

| | | |
|---|---|---|
| 2014/0298501 A1 | 10/2014 | O'Neill et al. |
| 2016/0227787 A1 | 8/2016 | Whyard |
| 2017/0191065 A1 | 7/2017 | Paldi et al. |
| 2018/0010130 A1 | 1/2018 | Estep, III et al. |
| 2018/0216110 A1 | 8/2018 | Sayre et al. |

FOREIGN PATENT DOCUMENTS

WO  2018/013801 A1  1/2018

OTHER PUBLICATIONS

Campbell et al., "Aedes aegypti uses RNA interference in defense against Sindbis virus infection", BMC Microbiology, Published Mar. 2008 (Year: 2008).*
Airs et al., "RNA Interference for Mosquito and Mosquito-Borne Disease Control", Insects, Published Jan. 2017, pp. 1-12 (Year: 2017).*
cdc.gov [retrieved on Nov. 16, 2023]. Retrieved from the Internet: <URL: https://www.cdc.gov/niosh/topics/outdoor/mosquito-borne/other.html>. (Year: 2016).*
cdc.gov [retrieved on Nov. 16, 2023]. Retrieved from the Internet: <URL: https://www.cdc.gov/mosquitoes/about/mosquitoes-in-the-us.html>. (Year: 2020).*
cdc.gov [retrieved on Nov. 16, 2023]; Retrieved from the Internet: <URL: https://www.cdc.gov/mosquitoes/mosquito-control/community/emerging-methods/genetically-modified-mosquitoes.html>). (Year: 2022).*
Rai et al., "Mosquito Genomes: Structure, Organization, and Evolution", Advances in Genetics, vol. 41, 1999, pp. 1-27 (Year: 1999).*
Colpitts, T.M., et al., Use of a tandem affinity purification assay to detect interactions between West Nile and dengue viral proteins of the mosquito vector, Virology, Jun. 23, 2011, vol. 417, pp. 179-187.
Terradas, G., et al., The RNA pathway plays a small part in Wolbachia-mediated blocking of dengue virus in mosquito cells, Scientific Reports, Mar. 6, 2017, vol. 7, pp. 1-13.

\* cited by examiner

*Primary Examiner* — Brian Whiteman
*Assistant Examiner* — Stephanie L Sullivan
(74) *Attorney, Agent, or Firm* — Hodgson Russ LLP

(57) ABSTRACT

Provided are compositions and methods for inhibiting transmission of viruses that use mosquitoes as vectors, such as dengue (DENV), Zika (ZIKV) and Chikungunya (CHIKV) viruses. Inhibiting transmission includes reducing viral load of the virus in mosquitoes. The viral load is reduced in mosquitoes that are exposed to the virus by introducing into the mosquitoes or mosquito larvae one or more agents that can participate in RNA interference (RNAi) of expression of one or more mosquito genes, such as alpha-mannosidase 2, or Cadherin87A, or a combination thereof. Also provided are modified mosquitoes or mosquito larvae that comprise the RNAi agents. The modified mosquitoes can be released into a population of unmodified mosquitoes to inhibit transmission of the virus between mammalian hosts. Also provided are compositions comprising an RNAi agent or an expression vector that encodes the RNAi agent for use in the described methods.

6 Claims, 13 Drawing Sheets
Specification includes a Sequence Listing.

Figure 2, continued

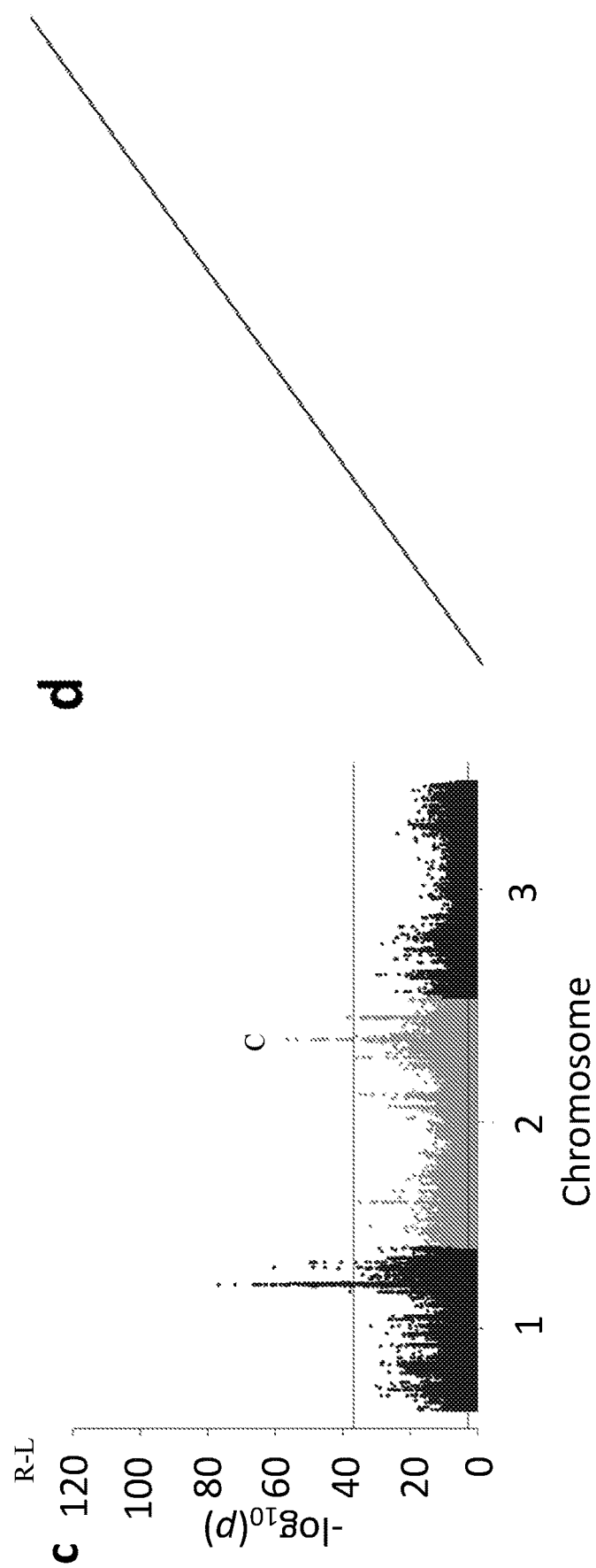
Figure 4, continued

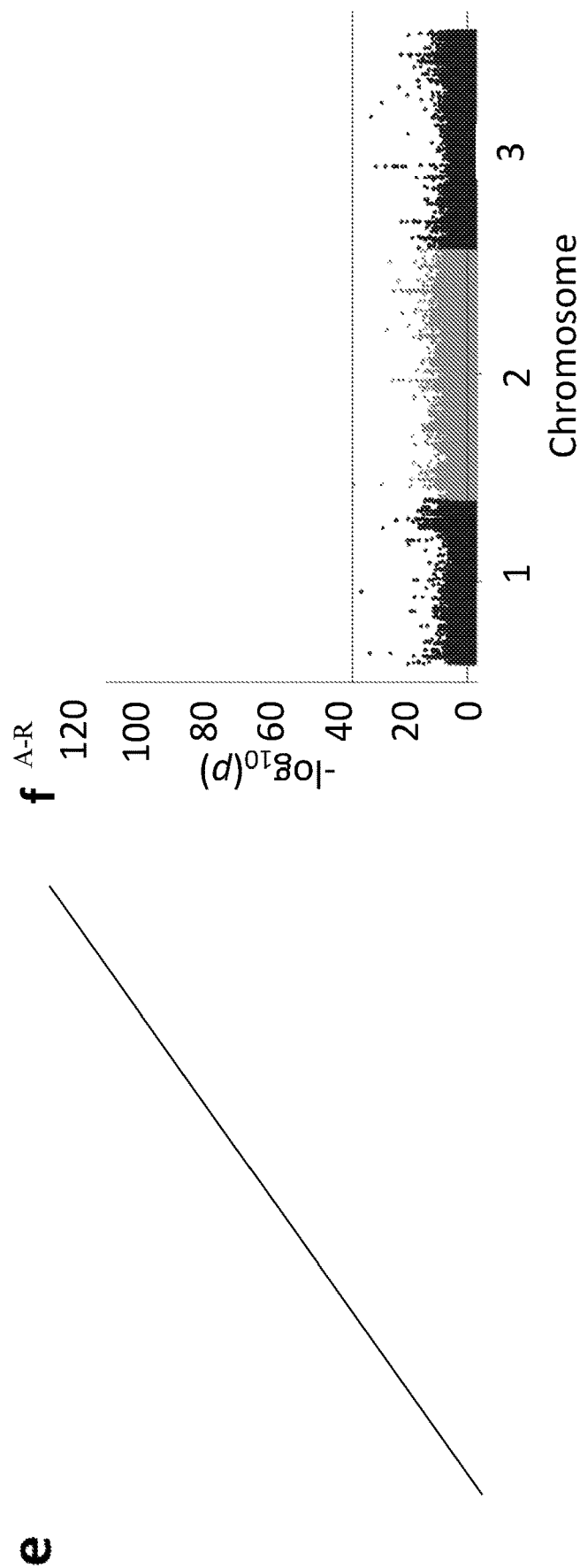
Figure 4, continued

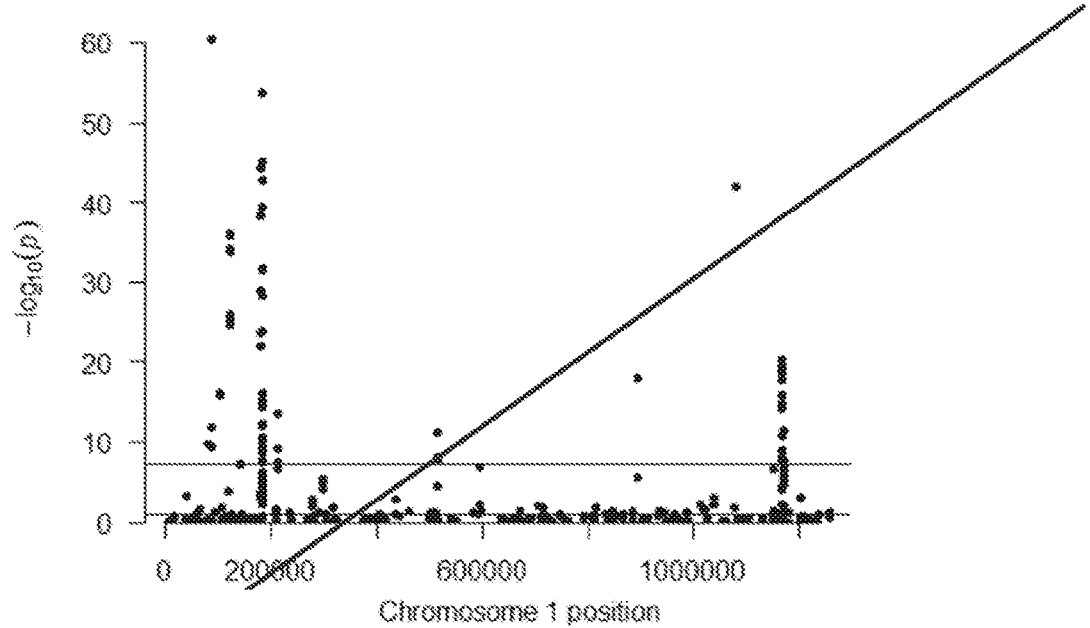
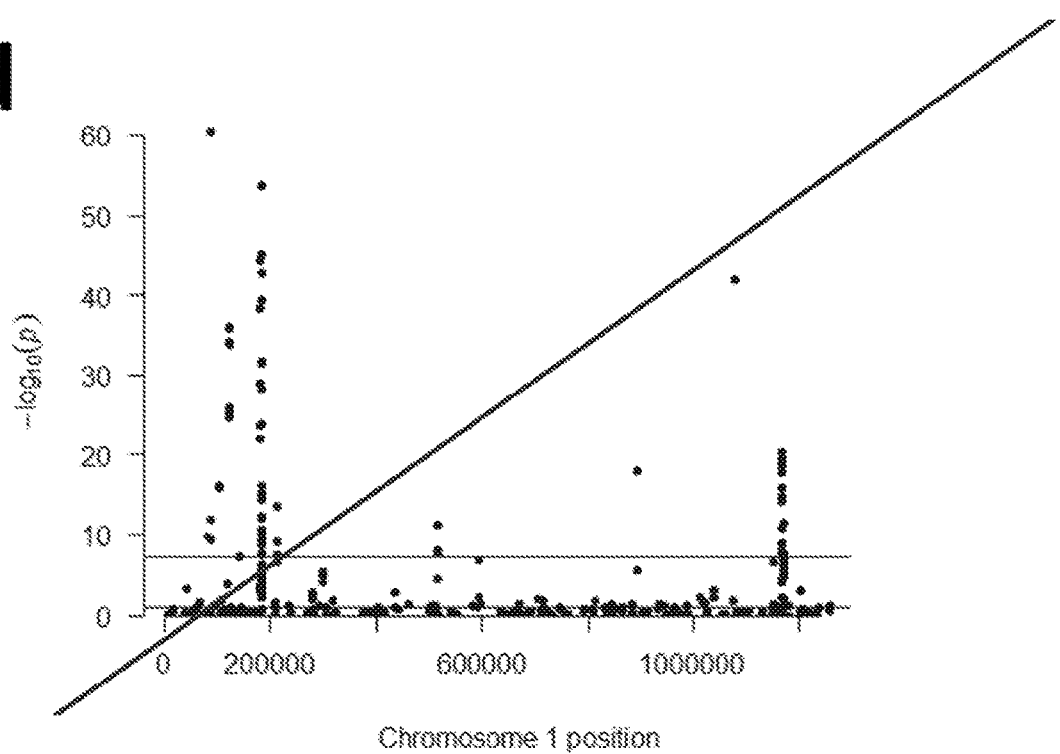
Figure 5, continued

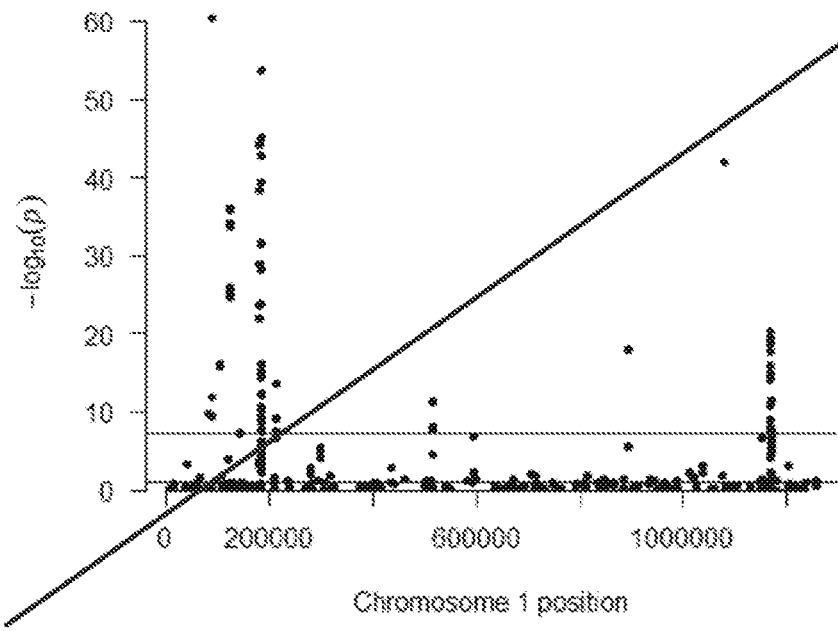
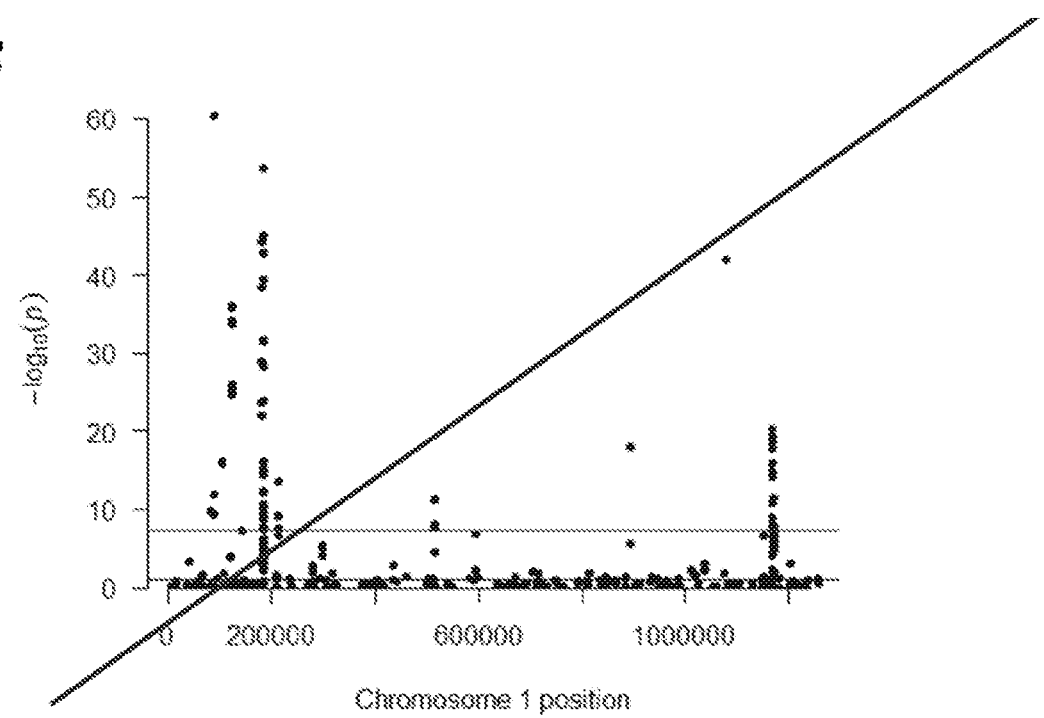
Figure 5, continued

COMPOSITIONS AND METHODS FOR USE IN CONTROLLING MOSQUITO-BORNE VIRUSES

CROSS-REFERENCE TO RELATED APPLICATIONS

This application claims priority to U.S. provisional application No. 62/724,468, filed Aug. 29, 2018, the disclosure of which is incorporated herein by reference.

STATEMENT REGARDING FEDERALLY SPONSORED RESEARCH OR DEVELOPMENT

This invention was made with government support under Hatch Act Project No. PEN04608 awarded by the United States Department of Agriculture. The government has certain rights in the invention.

FIELD

The present disclosure relates generally to inhibiting transmission of mosquito-borne viruses, such as dengue (DENV), Zika (ZIKV) and Chikungunya (CHIKV) viruses, and more specifically to inhibition of expression of mosquito genes to achieve this inhibition.

SEQUENCE STATEMENT

The instant application contains a Sequence Listing, which has been submitted electronically in .txt format and is hereby incorporated by reference in its entirety. Said txt file, was created Sep. 2, 2019, is named 074439.00149-McGraw_PSU_PCT, and is 53,900 bytes in size.

BACKGROUND

The *Aedes aegypti* mosquito transmits a range of viruses between humans, including DENV, ZIKV and Chikungunya (CHIKV). These viruses cause significant morbidity and mortality globally, with dengue fever alone estimated to affect 96 million people each year[1]. Vaccines and anti-viral chemotherapies against these viruses are either currently unavailable or are limited in their efficacy[2,3], while urbanisation, globalisation and the spread of insecticide resistance is making traditional methods of mosquito control increasingly difficult[3-6]. Consequently, novel strategies could play a major role in alleviating human populations from these pathogens[5]. One control strategy that may be used against these viruses is the use of a bacterium called *Wolbachia pipientis* that lives within insect cells. *Wolbachia* can 'block' the growth and transmission of viruses when introduced into the mosquito vector *Aedes aegypti*. Despite successful releases of *Wolbachia* into natural mosquito populations, it is unclear whether the blocking phenotype will remain stable over time. Thus, there is an ongoing need for improved compositions and methods for controlling these viruses that do not rely on use of *Wolbachia*. The present disclosure is pertinent to this need.

SUMMARY

The present disclosure provides compositions and methods for inhibiting transmission of viruses that use mosquitoes as vectors. In embodiments, the viruses are DENV, ZIKV, or CHIKV. In embodiments, the mosquitoes are *Aedes aegypti*. In embodiments, RNA interference (RNAi) is used to inhibit expression of one or more mosquito genes. In embodiments, the mosquito gene is alpha-mannosidase 2, or Cadherin87A, or expression of a combination of mosquito genes is inhibited. In embodiments, the mosquitoes may be infected by *Wolbachia* bacteria. In embodiments, the mosquitoes are not infected by *Wolbachia* bacteria.

RNAi inhibition can be achieved using a variety of RNAi agents and RNAi delivery techniques, such as by direct injection of an RNAi agent, administration of a recombinant vector encoding an RNAi agent, or by infecting the mosquitoes with bacteria that are modified to express the RNAi agent. Combinations of such approaches are included in the disclosure.

In a particular embodiment, the disclosure provides a method for reducing viral load in mosquitoes. The method comprises administering to the mosquitoes or mosquito larvae an RNAi agent that inhibits expression of mosquito alpha-mannosidase 2, or an RNAi agent that inhibits expression of mosquito Cadherin87A, or administering a combination of said RNAi agents, such that exposure of the mosquitoes to the virus results reduced viral load. The reduced viral load may be relative to any suitable control value, such as viral load in mosquitoes that are exposed to the virus but do not comprise the administered RNAi agent.

The disclosure also includes modified mosquitoes or mosquito larvae. The modified mosquitoes and/or the larvae comprise at least one administered or recombinantly expressed RNAi agent that inhibits expression of mosquito alpha-mannosidase 2, or mosquito Cadherin87A, or a combination of said RNAi agents. Such modified mosquitoes may be resistant to a viral infection and/or exhibit reduced capacity to transmit the viral infection to a mammalian host.

The disclosure also provides a method for inhibiting transmission of a virus between mammalian hosts. This approach comprises releasing the modified mosquitoes into a population of unmodified mosquitoes.

In another aspect, the disclosure provides an RNAi agent or an expression vector that encodes the RNAi agent, that can inhibit expression of *Aedes aegypti* alpha-mannosidase 2, or inhibit expression of *Aedes aegypti* Cadherin87A. Compositions comprising such RNAi agents are also included.

Each point is an average for each line. *Wolbachia* density is the relative number of *Wolbachia* genome copies relative to mosquito genome copies (measured by amplification and quantification of the *Wolbachia* gene WD0513 and the *A. aegypti* gene RPS17 using qPCR.).

Figure 4:
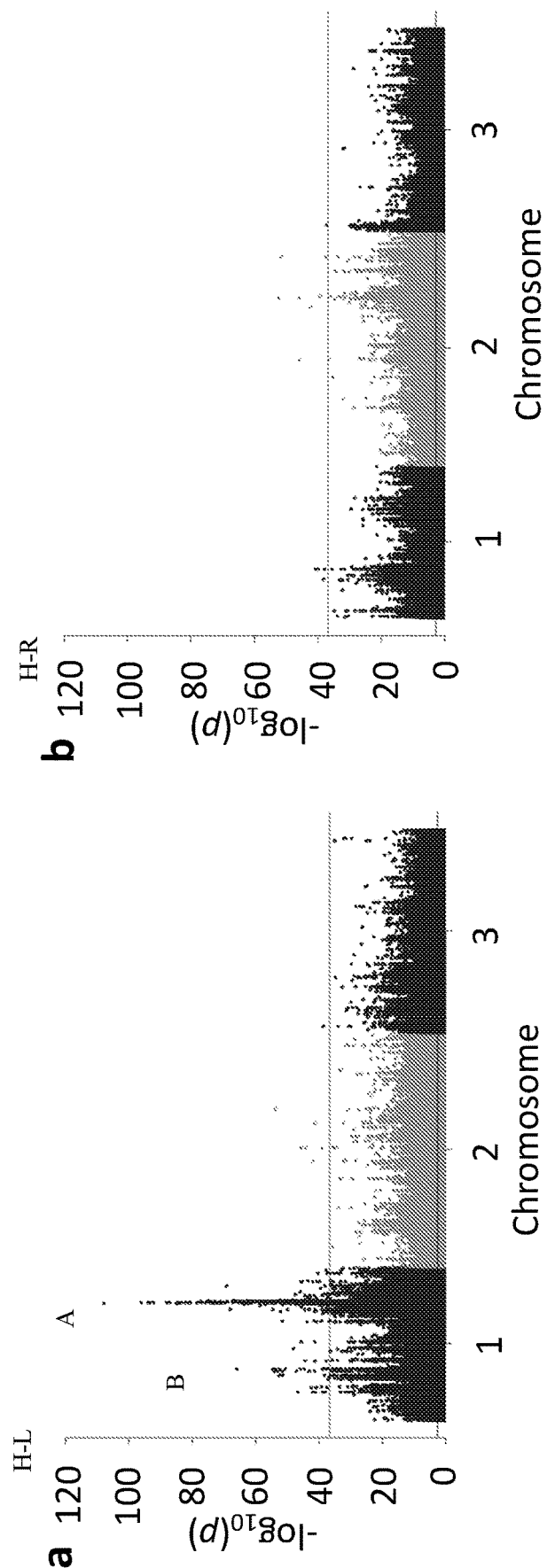

FIG. 4. Manhattan plots showing significantly differentiated SNPs over the *A. aegypti* genome using the Cochran-Mantel-Haenszel (CMH) test. Pairwise comparison between: a, High and Low blocking populations; b, High and Random blocking populations; c, Low and Random populations; d, Ancestral and High populations; e, Ancestral and Low populations; f, Ancestral and Random populations.

Figure 5:
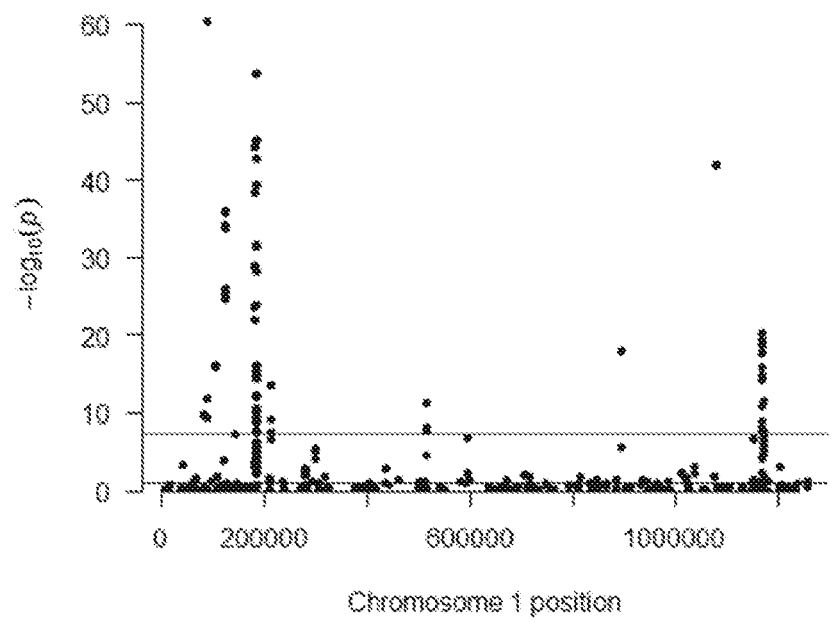
Figure 5:
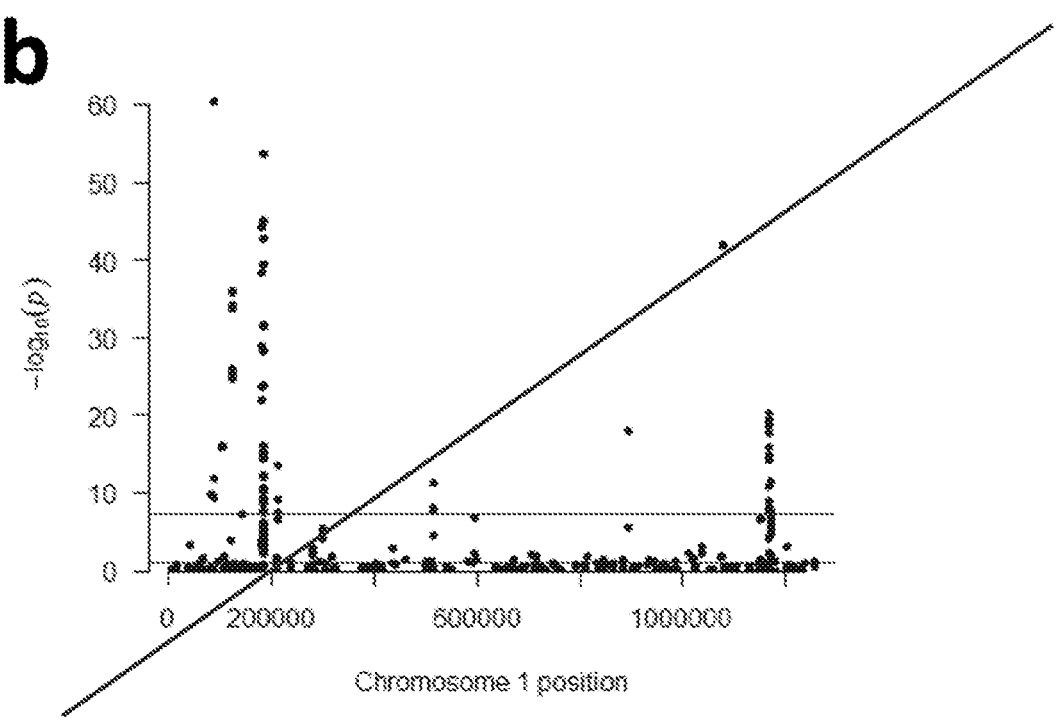

FIG. 5. Manhattan plots showing significantly differentiated SNPs over the *Wolbachia* genome using the Cochran-Mantel-Haenszel (CMH) test. Pairwise comparison between: a, High and Low blocking populations; b, High and Random blocking populations; c, Low and Random populations; d, Ancestral and High populations; e, Ancestral and Low populations; f, Ancestral and Random populations.

Figure 6:
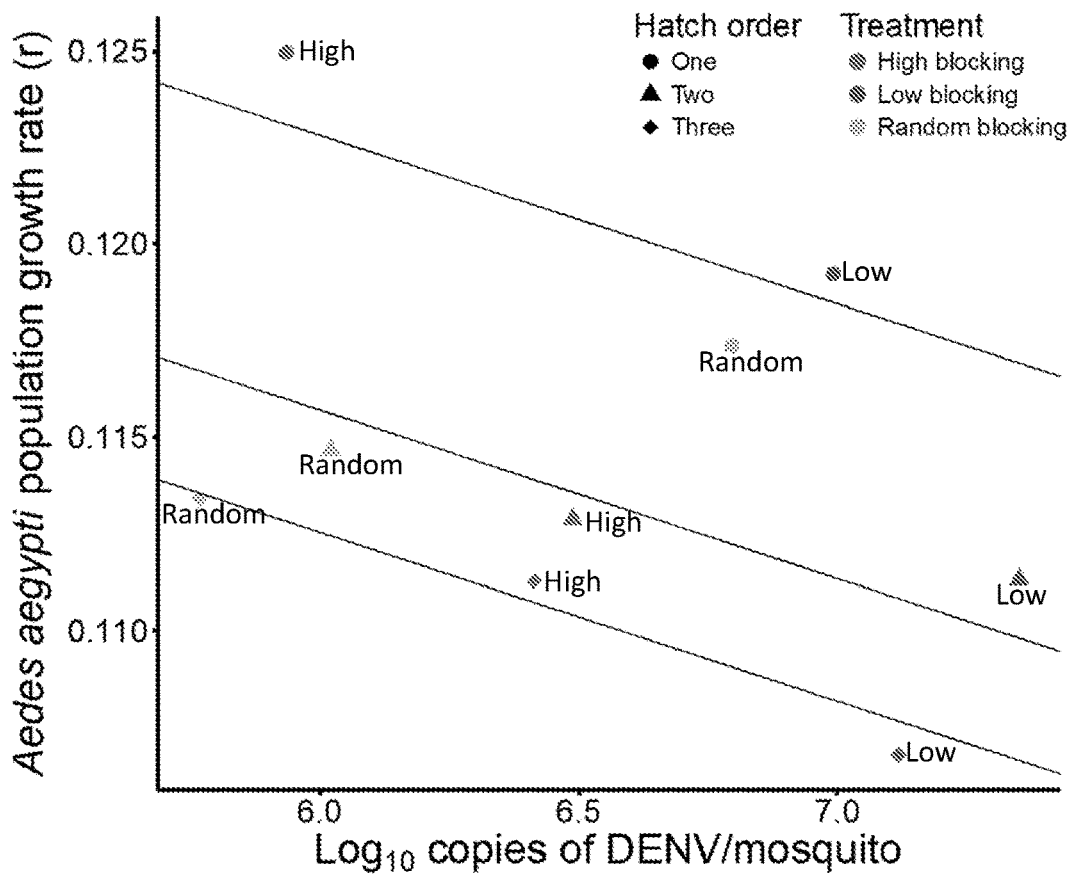

FIG. 6. Correlation between the population growth rate (r) of *Wolbachia*-infected mosquitoes and their ability to block DENV assuming low larval survival (43%). The population growth rate (r) is measured in the absence of DENV infection and thus is the intrinsic fitness of each mosquito population. It is calculated from an age-structured Leslie matrix model which combines different fitness measures. This output assumes low larval survival (43%), based upon unpublished data (Cator, L). The output under high larval survival (92%) is presented in FIG. 10. Hatch order was included as a random effect in the statistical analysis and so is represented here as separate lines of best fit.

Figure 7:
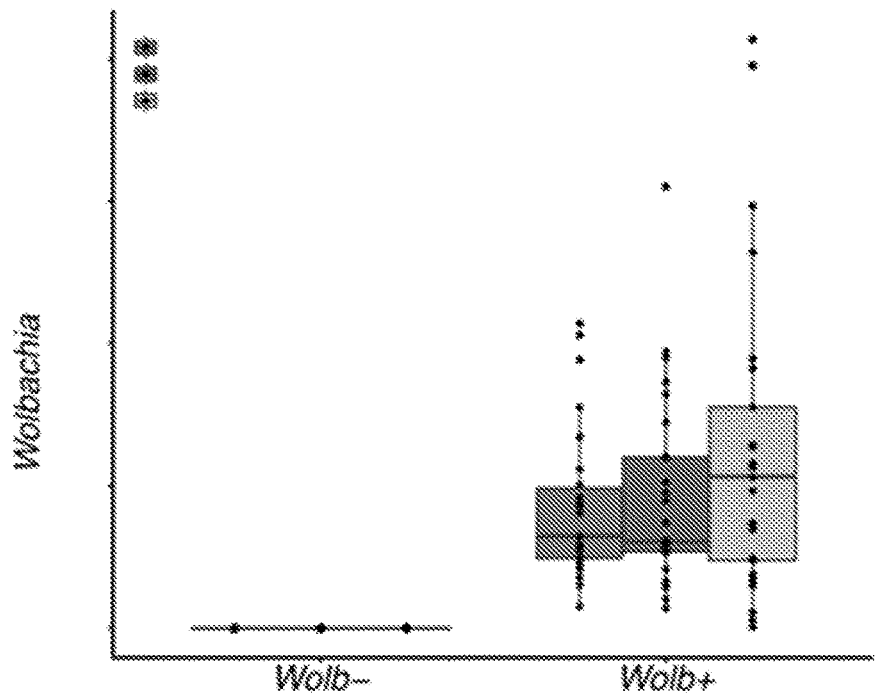

FIG. 7. *Wolbachia* removal with antibiotics. *Wolbachia* density in evolved lines that have been treated with the antibiotic tetracycline to cure them of *Wolbachia* (Wolb−) or not (Wolb+). *Wolbachia* density is measured by genome copies of *Wolbachia* (measured by amplification of the *Wolbachia* gene WD0513) relative to mosquito genome copies (measured by amplification of the *A. aegypti* gene RPS17).

Figure 8:
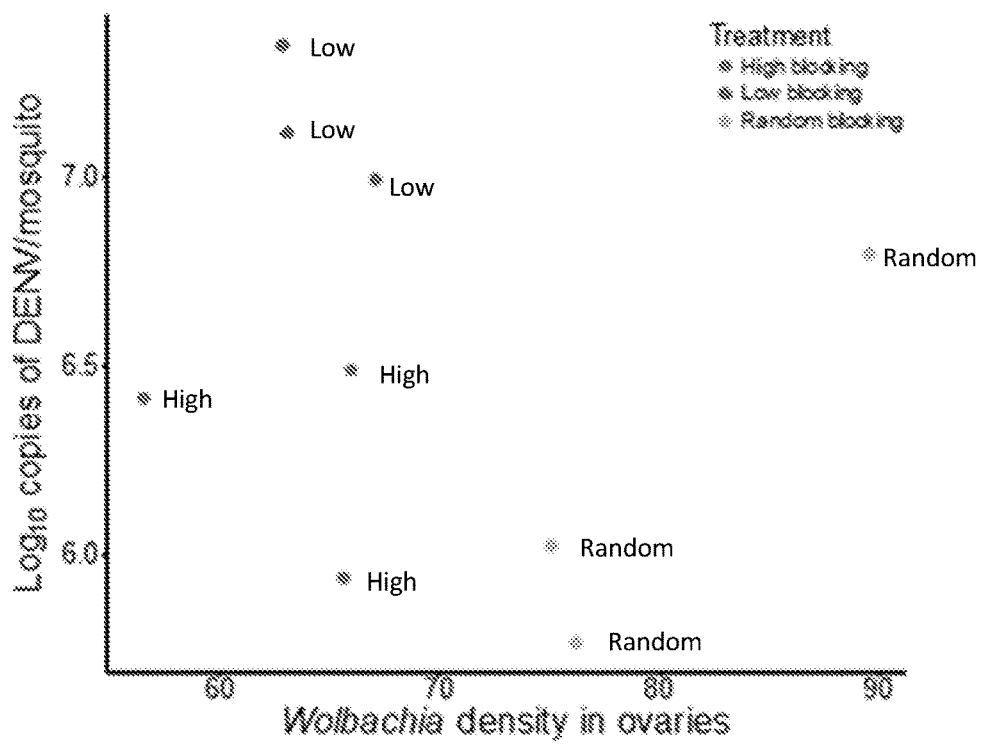

FIG. 8. There is no correlation between dengue virus load and *Wolbachia* density in mosquito ovaries. *Wolbachia* density is measured by genome copies of *Wolbachia* (measured by amplification of the *Wolbachia* gene WD0513) relative to mosquito genome copies.

Figure 9:
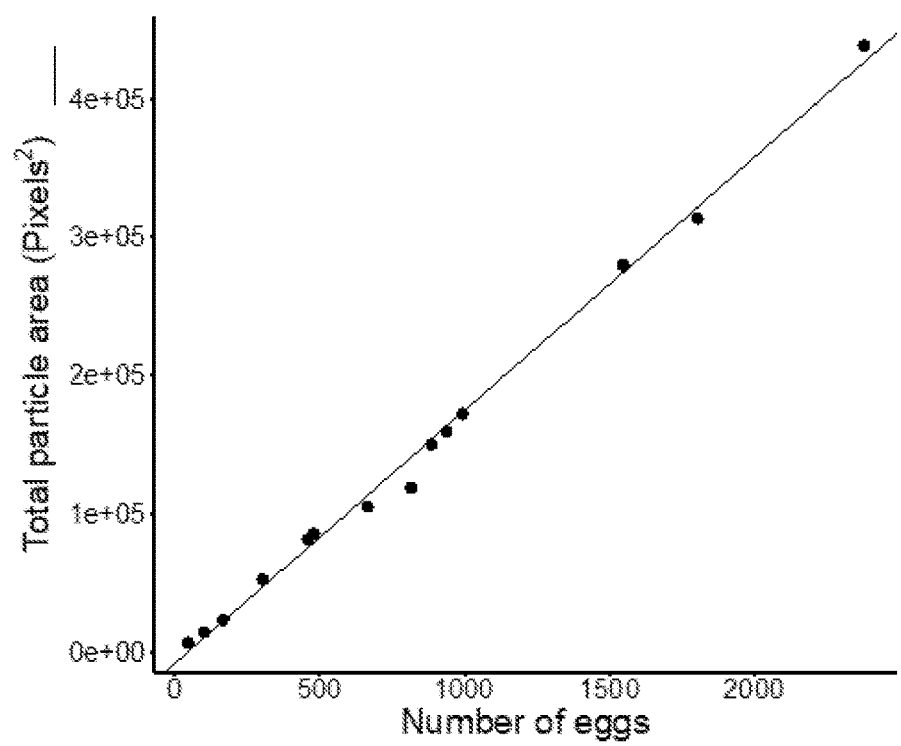

FIG. 9. Reference curve relating image detection of eggs (total particle area in Pixels$^2$) with a manual count of the eggs. Linear regression (Y=183.1547X-8596.8768).

Figure 10:
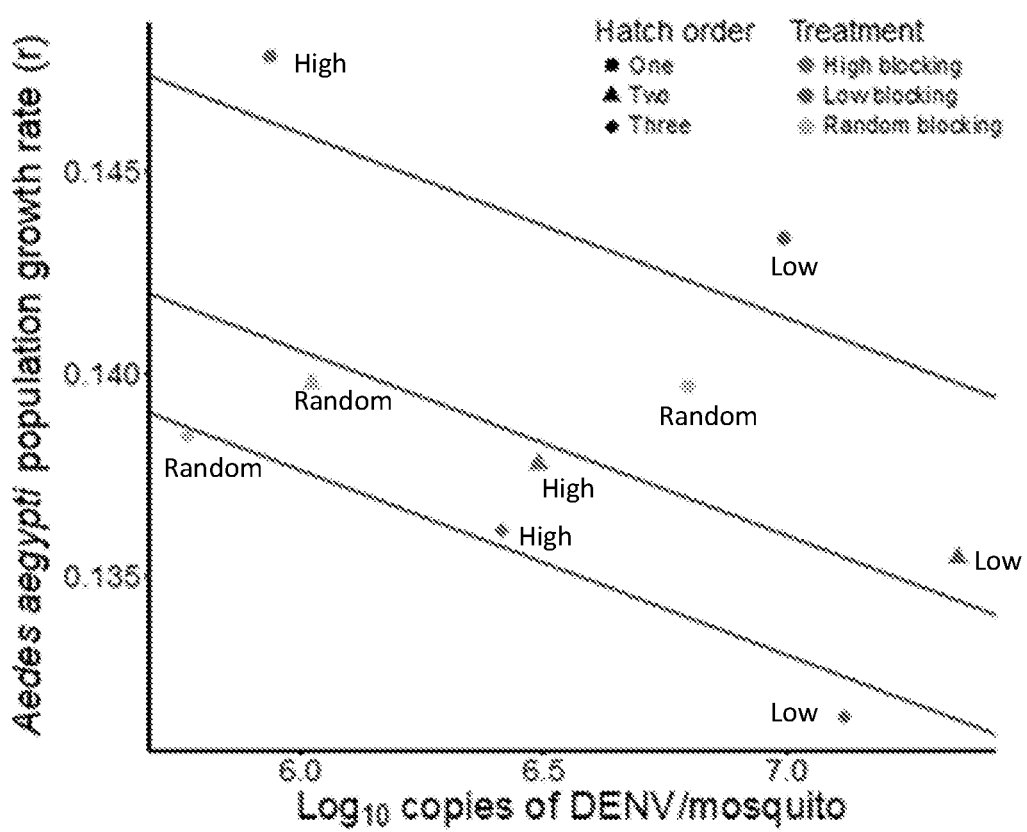

FIG. 10. Correlation between the population growth rate (r) of *Wolbachia*-infected mosquitoes and their ability to block DENV assuming high larval survival (92%). The population growth rate (r) is measured in the absence of DENV infection and thus is the intrinsic fitness of each mosquito population. It is calculated from an age-structured Leslie matrix model which combines different fitness measures. This output assumes high (92%) larval survival, based upon unpublished data. Hatch order was included as a random effect in the statistical analysis and so is represented here as separate lines of best fit.

Figure 11:
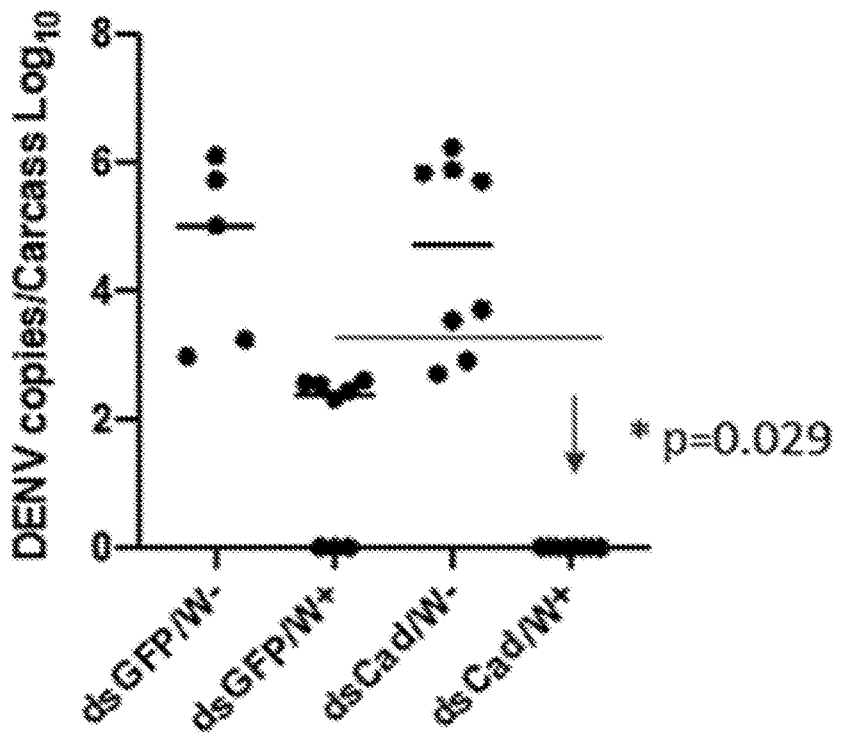

FIG. 11. RNA silencing of Cadherin gene in mosquitoes. Significant effect on dengue virus load in the carcass of *Wolbachia* infected mosquitoes 14 days post feeding of virus via blood meal. Double stranded RNA designed to target GFP served as the negative control. W+/− indicates *Wolbachia* infection status. P value by Sidak's multiple comparisons test.

Figure 12:
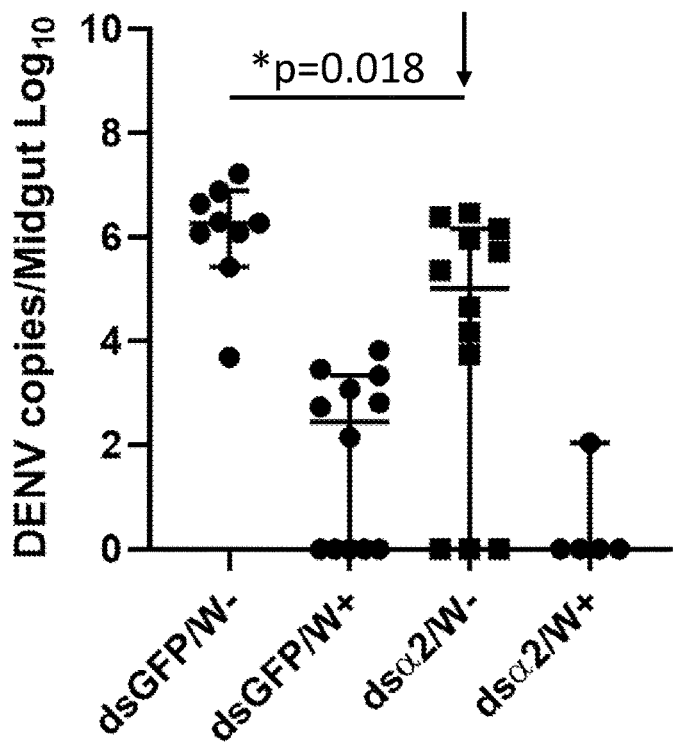

FIG. 12. RNA silencing of alpha mannosidase gene in mosquitoes. Significant effect on dengue virus load in the midgut of *Wolbachia* free mosquitoes 10 days post feeding of virus via blood meal. Double stranded RNA designed to target GFP served as the negative control. W+/− indicates *Wolbachia* infection status. P value by Sidak's multiple comparisons test.

DETAILED DESCRIPTION OF DISCLOSURE

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes the DNA equivalent of every RNA sequence described herein, and the RNA equivalent of every DNA sequence described herein. The disclosure includes all complementary sequences, as well as reverse complement sequences.

The disclosure includes all single-nucleotide polymorphisms (SNPs) described herein, and all manner of testing for such SNPs using any suitable sample obtained or derived from mosquitoes, as described further below.

The disclosure also includes sequences that have at from 80-99% identity with the sequences described herein, provided nucleotide or amino acid changes do not alter the function of the molecule in question so that it does not achieve its intended effect. Thus, polynucleotide sequences described herein may have nucleotide insertions, deletions, and mutations. The disclosure includes the proviso that any polynucleotide that occurs naturally in mosquitoes can be excluded from invention. Accordingly, the disclosure comprises in certain embodiments use of a segment of an artificially generated RNA that would target mosquito mRNA using one or more molecular-biology based approaches, including but not necessarily limited to by altering the copy number of the gene encoding the RNA, by using only a segment of the RNA, by overexpressing the RNA, or by expressing the RNA or a segment thereof as further described herein from an expression vector. Modified mosquitoes that express any polynucleotide, or exhibit increased amounts and/or have increased gene copy numbers, are included in the disclosure.

Non-limiting embodiments of the disclosure are illustrated using a dsRNA adapted from *Aedes aegypti* mRNA encoding cadherin, and separately an *Aedes aegypti* mRNA encoding alpha mannosidase. All of the description that relates to this example applies to each and every other RNA polynucleotide described herein, including but not necessarily limited to those sequences represented by the information presented in Table A, which provides genes, cDNA sequences, and other information regarding *Aedes aegypti*.

TABLE A

| Gene | No. of snps | #nucs | Snps per bp | Min-pvalue | Max-pvalue | gene name |
|---|---|---|---|---|---|---|
| AAEL004389 | 357 | 7138 | 19.99439776 | 1.00E−100 | 0.04994742 | Alpha mannosidase |
| AAEL023845 | 627 | 9594 | 15.30143541 | 7.58E−97 | 0.04941792 | cadherin |
| AAEL018695 | 267 | 5470 | 20.48689139 | 8.16E−76 | 0.04992507 | |
| AAEL014511 | 210 | 4375 | 20.83333333 | 7.34E−70 | 0.04875134 | N/A |
| AAEL006196 | 35 | 2836 | 81.02857143 | 1.07E−68 | 0.04758416 | hemomucin |
| AAEL022656 | 65 | 1139 | 17.52307692 | 7.98E−68 | 0.04167159 | N/A |
| AAEL023759 | 32 | 3832 | 119.75 | 1.23E−66 | 0.04845109 | N/A |
| AAEL008334 | 217 | 9624 | 44.35023041 | 2.97E−64 | 0.04955478 | N/A |
| AAEL002769 | 327 | 10154 | 31.05198777 | 1.72E−59 | 0.04810721 | |
| AAEL014528 | 36 | 1968 | 54.66666667 | 2.31E−55 | 0.048897 | |
| AAEL010881 | 401 | 1141 | 2.845386534 | 1.72E−54 | 0.04979738 | |
| AAEL019422 | 357 | 5530 | 15.49019608 | 2.34E−53 | 0.04965694 | N/A |
| AAEL027527 | 131 | 5172 | 39.48091603 | 3.70E−53 | 0.0492046 | N/A |
| AAEL005813 | 53 | 4412 | 83.24528302 | 2.48E−52 | 0.04113651 | NELF |
| AAEL025611 | 9 | 4700 | 522.2222222 | 3.01E−52 | 0.02686835 | N/A |
| AAEL004233 | 385 | 3660 | 9.506493506 | 1.95E−51 | 0.04952328 | N/A |
| AAEL019927 | 35 | 2932 | 83.77142857 | 3.80E−51 | 0.04424921 | N/A |
| AAEL019447 | 136 | 4920 | 36.17647059 | 3.80E−51 | 0.04673519 | N/A |
| AAEL004396 | 456 | 3657 | 8.019736842 | 8.28E−50 | 0.04974027 | |
| AAEL022231 | 157 | 714 | 4.547770701 | 8.28E−50 | 0.04855324 | N/A |
| AAEL002173 | 29 | 2483 | 85.62068966 | 5.67E−49 | 0.04144512 | N/A |
| AAEL002169 | 39 | 9999 | 256.3846154 | 2.93E−48 | 0.049814 | N/A |
| AAEL022176 | 48 | 2777 | 57.85416667 | 2.98E−48 | 0.04664656 | N/A |
| AAEL002876 | 341 | 8046 | 23.59530792 | 2.98E−48 | 0.04946527 | N/A |
| AAEL009466 | 249 | 8180 | 32.85140562 | 1.46E−47 | 0.04844907 | |
| AAEL020340 | 418 | 5253 | 12.56698565 | 9.35E−47 | 0.04911214 | N/A |
| AAEL021067 | 573 | 4325 | 7.547993019 | 1.73E−46 | 0.04969989 | N/A |
| AAEL004700 | 118 | 2001 | 16.95762712 | 1.94E−46 | 0.04773173 | cdkl1/4 |
| AAEL024283 | 485 | 6723 | 13.86185567 | 3.41E−45 | 0.04962042 | N/A |
| AAEL013026 | 101 | 2669 | 26.42574257 | 1.56E−44 | 0.03990847 | |
| AAEL024147 | 95 | 3805 | 40.05263158 | 3.00E−44 | 0.0391458 | N/A |
| AAEL019752 | 427 | 8435 | 19.75409836 | 5.50E−44 | 0.04994045 | N/A |
| AAEL010513 | 240 | 4144 | 17.26666667 | 6.20E−44 | 0.04989911 | |
| AAEL019639 | 146 | 6661 | 45.62328767 | 1.30E−43 | 0.04783913 | N/A |
| AAEL020614 | 198 | 5633 | 28.44949495 | 3.64E−43 | 0.04969003 | N/A |
| AAEL019720 | 98 | 9507 | 97.01020408 | 1.02E−42 | 0.0457651 | N/A |
| AAEL005802 | 16 | 3863 | 241.4375 | 2.67E−42 | 0.04815738 | |
| AAEL014044 | 29 | 2815 | 97.06896552 | 3.16E−42 | 0.04769956 | N/A |
| AAEL019638 | 281 | 6518 | 23.19572954 | 6.63E−42 | 0.04991624 | N/A |
| AAEL018306 | 225 | 5292 | 23.52 | 1.07E−41 | 0.04928079 | N/A |
| AAEL024508 | 15 | 3343 | 222.8666667 | 1.83E−41 | 0.000932615 | N/A |
| AAEL008617 | 67 | 8005 | 119.4776119 | 1.29E−40 | 0.04903814 | N/A |
| AAEL020230 | 277 | 5162 | 18.63537906 | 5.29E−40 | 0.04854234 | N/A |
| AAEL025250 | 569 | 5397 | 9.485061511 | 1.21E−39 | 0.04994368 | N/A |
| AAEL007483 | 85 | 3889 | 45.75294118 | 1.22E−39 | 0.04357599 | N/A |
| AAEL010721 | 43 | 2580 | 60 | 3.86E−39 | 0.04873577 | |
| AAEL002879 | 99 | 8839 | 89.28282828 | 4.88E−39 | 0.04611968 | |
| AAEL023695 | 99 | 5972 | 60.32323232 | 6.68E−39 | 0.04794791 | N/A |
| AAEL013723 | 1129 | 10081 | 8.929140833 | 7.57E−39 | 0.04993501 | |
| AAEL019426 | 363 | 5999 | 16.5261708 | 1.80E−38 | 0.04970021 | N/A |
| AAEL002571 | 330 | 6941 | 21.03333333 | 1.82E−38 | 0.04968003 | |
| AAEL002859 | 722 | 10617 | 14.70498615 | 2.94E−38 | 0.04980661 | N/A |
| AAEL018215 | 236 | 7299 | 30.9279661 | 3.99E−38 | 0.04928266 | N/A |
| AAEL006208 | 31 | 3705 | 119.516129 | 4.80E−38 | 0.02803775 | N/A |
| AAEL006817 | 20 | 1406 | 70.3 | 7.44E−38 | 0.005209389 | N/A |
| AAEL019991 | 18 | 715 | 39.72222222 | 1.80E−37 | 0.03445773 | N/A |
| AAEL020617 | 78 | 10877 | 139.4487179 | 3.58E−37 | 0.0486428 | N/A |
| AAEL004572 | 498 | 7443 | 14.94578313 | 7.69E−37 | 0.04988507 | N/A |
| AAEL011522 | 146 | 2116 | 14.49315068 | 1.57E−36 | 0.0476363 | |
| AAEL007205 | 78 | 4816 | 61.74358974 | 2.34E−36 | 0.04866314 | |

The disclosure includes all polynucleotide and amino acid sequences described herein, including in the text, figures, tables, and any supplemental material that is part of this disclosure. Any reference to a database that includes an accession or gene or other number or alphanumeric indicator includes the sequences associated with the database entry as of the filing date of this application or patent. For example, in Table A, each alphanumeric designation under the Gene column provide is an alphanumeric identifier for a gene that is indexed in, for example, www.vectorbase.org. Querying this database for, for instance, AAEL004389, leads to a transcript table. In the transcript table, there are RefSeq links. Each of these links leads to a GenBank accession entry for an *Aedes aegypti* gene, such as alpha-mannosidase 2 mRNA sequence using the AAEL004389 designation, provided as a cDNA sequence. The same approach applies to the Cadherin-87A gene (AAEL023845). The database entry also provides the amino acid sequence encoded by the cDNA sequence. All of these cDNA sequences (and their corresponding mRNA sequences) for each gene in Table A, the amino acid sequences encoded by those genes, and any polynucleotide encoding the amino acid sequences, are incorporated herein by reference as they exist in the database on the filing date of this application or patent. Further, those skilled in the art will recognize alternative methods for accessing the sequences, and will recognize that all of these sequences are encompassed for use in any embodiment of this disclosure.

This disclosure also shows that a gene in the mosquito showing evolutionary change in association with both weakened and improved DENV blocking is the cadherin-87A gene (AAEL023845). Therefore any RNAi agent that could be designed to target the mRNA of this gene and affect its expression is encompassed by this disclosure for use in, for example, limiting viral replication. The same applies to the alpha-mannosidase gene. Accordingly, the present disclosure provides for inhibiting transmission and/or blocking replication or transmission of DENV, ZIKV, CHIKV, or any combination thereof, to mammalian hosts, and thereby includes inhibiting development of viral infections in the mammalian hosts, including but not necessarily limited to human hosts.

In particular embodiments, the disclosure relates to inhibiting expression of *Aedes aegypti* Cadherin87A, and/or *Aedes aegypti* alpha-mannosidase, or any gene or protein encoded by the gene described by way of Table A, using a polynucleotide targeted to a segment of such gene(s) and/or RNA(s) encoded by them.

In non-limiting embodiments, the disclosure provides compositions and methods that relate to use of engineered polynucleotides that can participate in RNAi-mediated inhibition, to inhibit translation of mRNA, and/or to degrade mRNA, that encodes *Aedes aegypti* protein(s). All mRNAs, including all splice variants, which encode an *Aedes aegypti* CAD or *Aedes aegypti* alpha-mannosidase, or any RNA or protein described in Table A, are included as targets of the RNAi agents of this disclosure. In non-limiting embodiments, an approach of this disclosure use of a segment of RNA or derivative thereof encoding the *Aedes aegypti* Cadherin87A (CAD) protein or the *Aedes aegypti* alpha-mannosidase protein for RNAi mediated gene expression inhibition. The disclosure includes targeting any RNA encoding the *Aedes aegypti* CAD protein, the sequence of which is as follows.

```
Aedes aegypti Cadherin 87A protein (CAD)
                                     (SEQ ID NO: 1)
MIASTQKQQQRWTVLIPLLTIGFLIRTCHCNLPPIFTQDMNNLALP

ETTPVGSVVYRLEGYDPEGGNVSFGLLGSDNFMVDPISGDVKVIKP

LDREDQDTLSFSVTIKDRISTAGIDSENDNVVNVPITIIVLDENDN

PPEFRNVPYETEVLEDAKPGTTVFSDILVTDRDTVGDNLIVNCIPQ

PQNPDACEKFAIETLESGQDRLTASVVLKGRLDYNERMIYQILLEA

TDGMFNATAGLEIHVKDVQNSAPVFQGSLAAVINEDSKIGTLVMMI

HARDGDRGQPRKIVYELVTNPMDYFLLDRQTGELRTAKPLDKEALP

DDTGLIILTVKARELIDGVPGNDNLTTATTQASITIRDVNDSPPMF

NKKEYFVSLSENTAPGTPLPIEMSVHDPDVGENAVFSLRLNDVSEV

FDVEPKLVTGSSQISIRVANGSLDYENPNQRKFIVLVIAEETQTNP

KLSSTATLTVSITDSNDNRPIFEQDSYSTTVSETAHPGHLITTITA

RDLDSGHFGDQGIRYSLSGTGAELFNVDPITGAITVADCPSVDNDN

NKRRRRRRQIPSSDELTQDYPDMKRFNVSTDGRSGVLDRGVDYMAY

KIYNSGESNEYRDVNVVAPPTVSSSWETSSLEESDSTPAIESEEYF

TPSSTTTPIHSNEIQHRSDVGPGRAPCLDYENQSVYYLSYKATDDE

GRGQTSVVSLRITLLDANDSPPVCESPLYRASVDEGATLFEPPLVI

KARDPDVISEINYRIIGNEAITRHFEIDKRSGQLTISKSTALDVNH

LKSENVFFAVEASDGLFTTLCNVNITIRDVNNHAPQFSREHYLASI

EENFPIGTRVERLQAIDLDTGINAEIRYRIQQGSFDDFAIDNQTGV

VTIARKLDYDRRNTYQMEIVAADLGTPSLSGTTTLTVSIINSNDKA

PYFTPTTQRAEISEDAEVGTLVHTLVALDPDVASSEALDYAATEPI

TAVDKDGKEVRDTEDFKDMFRIDRTGKVFVNRKLQRDDFAVIRITV

LVTDTTAPSIQQGEGLLIITIIDVNEEPPLFVPPWTPADPRYRFQV

LEEQPIGTILTTMQATDADSTVAEYRMTDNSHFEINNTTGLIRTKA

RIDYEQTPTIQFNVTVVDTGIPQLTSTAEVTVDIINTNDNDPAFDE

PEYEMSVVENAPTGTVVGIVSARDADSGPYGQITYSLVGDHSAASF

AIDPDTGVITVRDGTTLDRERT1EIGLTAIATDRAPDGTSRSTTAP

VTIKLLDENDNVPTFSQKIYHATVAENAALNPPAAILQVLATDPDE

GAAGDVKYSIIGSDIENTFRLDANSGILYPYASLLGLDGNYRIQIE

ARDGLGSGPHSDRAEIKIEIQSINQHRPIFIMPALSNATVEIPENL

AMTDYLVMTVKANDSDEGTNGKVLYHLQVNNQNVQETDEFIINEMS

GELRIRKPLNRKKQARFELILVARDQGTPAWFETLRFLTVLLVDVN

ENHPEFPDASNPYRFFIAENSPRDIRIGKIQAYYDTPDPKIYYYMM

LGNEDGAFYVDKTTGDIYTNKTLDREEADVYALYIKASKKQDLLIT

ERDRMMMSTKKLERDSTVAKVVVITVLDVNDNPPVFKQDVYYAGVS

SKAAINELVTIVNATDRDLGVNSTMELFISGSYLYKYGATKTTGSI

VPSPFTISKDGRITTANYMAEYNQDRFILDIVAKEVESPERVATTK

VYVVVIFNPEQLVRVILSRPPSEVHMERDEIISELSNATQKLIIVD

EIRYHVDSLGRIRMDWCDMYFHAIDMSSQTIVSVEEILREIDAKYD

FLQDYNAGFSIENVVPAYATNVQDEFDLALAAIIALLIVLFVGAVS

FIVLCCCLKHWVITIPNETRRKDALIKKQIIEDLNTTENPLWIEQK

LKLYEEQELTMQVFSEPELTQQQQQHHHQQQLNSSNNTSSSLASHQ

NQHHHVMQQQEQALVLGLDRRDSYPELSQGGGDNTYATIQPRNYAS

NLSSVLMGTSGIGGGGGGGSGNGAAPAGGLSGEMSDYATLRNSRAP

SMYEFRGSTFQVQQLNGGPGGDQPDYVTELI
```

The following is a representative cDNA encoding of the mRNA encoding the *Aedes aegypti* CAD protein.

```
Aedes aegypti cadherin-87A (LOC110674038),
transcript variant X4, mRNA (provided as
cDNA sequence):
                                     (SEQ ID NO: 2)
TAGCAAAACGTAGCTGCTCCGTTGGTTCAGACTACAGTTGACGTCG

CGATTTCAACCCGATTGGATTGGCTTCCCTTCAATCCGGACAAAAA

CTCGGAAGAAACGTAAACGCCGCTTTTCGAACAGAGCATCTTGGTT

GCTTTTGGGGCCTCGTGAAGCTCGTGTCGCCGGATGAGAGGATTTG

GAAATACAGCAACAATAGCAGGATAATCTCCATATCATTGGTTGAC
```

-continued

TATGGTAGCTCGTCATCGCTGTCGCTGGCTCACTGGTGAGCAAGGG
AGGAAGCGTGGTGGTGAATAATTCGATAGGTGCAATTTTCACGGTG
ATTGCTCGAGTGGTCGATTGAGAAGGACTGGCTGGGAAAACCGGTT
TTCCACCAATTCAGTGTCGATTGTCGAAAGAAACCGACAAACAGTA
TCGTTGGGTTCGTTTTGTGTGGCGGAGTGGGTTGAGTGTCTGATTA
GAAATAAAAGTGGAAGAATATCATCACTGGCAGTTATCTGTAACTG
ATTCGTTGCAGGCGTCGGTACCGCACCTGGCTCCGCGAAGCAATAT
CAGCTCCGCTGTTGATGAAAGTTTTGCTTTAAGTTCTTCAGCTCCA
AGTTTCTGTTGTTGTTTGCCCGGTTGTTGTTGTCAGTGCTGGTGTT
TCTCCCATCCCCGGAAACCGGTACCATTACATAAAGAGCAAAGTTC
TTCGCCGTACACCCAAGGCTTGCAACCGCGAACACGATGCGATGCT
AAATCCTAAGCCAGTCTTCGAGGCGTTCCACTAGGACATTTGTGCC
TCCTTCGGGAAAGTGATCTGGCGTCGTCATGAATATTTTATACGCG
CTACGACGAGTGTGCTTCGCTTTTGCGATTTCCTGTCAGTCTGTGC
AAAAATAATATCCCACTCAATACAAGAGCAGAAGCAAAAAGCCCCA
CAGTAAGAAAAATAGTAGCAAAGCAGCATATCATAATAGTCGTTAA
GAATAAAGAAAATATAATTGAAACGTGTTTCCGAGCGAAAAGGGAA
AAAGTGTTGCCTCGGCGAGAGTTGCACAAAAAGTGGAGGAAATTAA
AAGAAGCTACTATTCTCGTAACGAAAAGCCAAGAAGCGTGGTTGGT
TGTGCGAAGGAAAAAGTGAATGATTTATTCAGTGGATCGTCTCTCG
GGTTCGTTGGAGGAAACGTGTAAGAGAAGAGCAGTCAGCAGCAAGG
TGAAGATTGTGCGAAAACTGTAAATCAAGCGGAACGACGACGGCGA
CGAATATGAATGCGAAAGTTGAAGTCGACGGCCAGGTCGTCTTCAT
CAGCATCATCAGAGAAGTTGTGGGCTGTAGTGACGGGTGGTGTAAA
GTGTAGGAGTCTGCTGGTAAAGCTGAGTTGTAGTGGTTTTGTTTTT
ATCAAGAAAGGATTCCAAGAAAGAAGAAAAGAACATTTAAGGAGAG
TAGTGTCTTTGGCGTTTGGAGCTTTGCCGGTGCGGAACCCAATTAG
AGCAGCTAAAGAAAGATTCATCTTTCGTAATTCAATATCTCTAAAC
TGAACGGAAGTGAACTAGAATTGTGTGTGTGTGGCAAGGACGACCA
GGCGACGAAGCAGCCGCCATTCAGCAATGATAGCCTCCACCCAGAA
GCAGCAACAGCGATGGACAGTTTTAATACCGCTCCTAACGATAGGG
TTCCTGATTCGGACATGTCACTGCAACCTGCCGCCGATTTTCACGC
AGGACATGAACAACTTGGCCCTGCCGGAGACAACTCCGGTGGGAAG
CGTCGTTTACCGGCTGGAGGGTTACGATCCGGAGGGCGGTAACGTC
TCGTTTGGGCTGCTCGGCTCGGACAACTTTATGGTGGACCCAATCA
GTGGGGACGTCAAGGTGATAAAACCGCTGGACCGTGAGGACCAGGA
CACCCTCTCCTTCTCGGTGACCATCAAGGATCGCATCAGCACCGCA
GGAATCGATTCCGAGAACGACAACGTGGTCAACGTTCCCATCACGA
TAATCGTCCTGGACGAAAACGACAACCCACCGGAATTTCGCAATGT
TCCCTACGAAACAGAGGTCCTGGAGGACGCCAAGCCAGGCACCACC
GTGTTCAGCGATATCCTGGTTACCGATCGGGACACCGTCGGAGATA

-continued

ACCTGATCGTGAACTGTATTCCACAACCGCAGAACCCGGATGCTTG
CGAAAAGTTCGCCATCGAAACCCTCGAAAGCGGTCAGGATCGACTA
ACGGCTTCGGTGGTGCTGAAGGGTCGCCTAGACTACAACGAACGGA
TGATCTACCAGATTCTGCTGGAGGCTACCGATGGGATGTTCAACGC
CACGGCTGGACTGGAGATCCACGTGAAGGATGTTCAGAACAGTGCG
CCGGTGTTCCAAGGATCGTTGGCGGCGGTAATCAACGAGGACAGCA
AGATCGGGACGCTGGTGATGATGATCCACGCAAGGGATGGCGATCG
GGGTCAACCGAGGAAGATTGTCTACGAATTAGTTACGAACCCAATG
GATTACTTCTTGCTGGATCGTCAAACGGGTGAGCTACGCACGGCCA
AACCACTCGACAAGGAAGCCCTTCCCGACGACACCGGGTTGATAAT
CCTGACGGTTAAAGCTCGCGAGCTGATCGACGGAGTTCCCGGTAAT
GACAATCTGACCACGGCAACAACACAAGCGTCGATCACGATTCGCG
ATGTGAACGATTCTCCACCGATGTTCAACAAAAAGGAATACTTCGT
ATCGCTGTCGGAGAATACGGCTCCGGGAACGCCACTTCCGATCGAA
ATGAGCGTTCATGATCCGGATGTTGGAGAGAACGCTGTGTTTTCTC
TACGCTTGAATGATGTTTCGGAAGTGTTCGATGTGGAGCCAAAATT
GGTGACGGGATCGTCACAGATTAGTATTCGTGTAGCGAATGGTTCG
CTGGATTACGAAAACCCTAACCAACGGAAGTTCATCGTATTGGTGA
TCGCTGAAGAAACCCAGACGAACCCTAAGCTGTCATCGACAGCTAC
TTTAACGGTGTCTATCACCGACTCGAATGACAACCGTCCGATCTTC
GAGCAGGACTCGTACTCTACAACTGTATCGGAAACTGCTCATCCCG
GTCATTTGATAACGACCATCACCGCCAGAGATCTCGACTCAGGTCA
TTTCGGCGACCAAGGAATTCGGTATTCCTTGTCTGGAACGGGAGCC
GAACTCTTCAACGTCGACCCGATAACCGGCGCTATAACGGTCGCTG
ATTGCCCATCCGTAGACAACGACAACAACAAAAGACGTCGTCGGCG
ACGTCAGATTCCTTCATCCGATGAGCTGACTCAAGACTACCCGGAT
ATGAAACGTTTCAACGTGTCAACCGACGGACGTTCGGGCGTCCTAG
ACCGTGGCGTAGACTATATGGCCTACAAGATCTACAACAGTGGCGA
ATCGAACGAGTACCGAGACGTGAATGTCGTCGCACCTCCAACGGTT
TCCAGCAGCTGGGAAACGTCCAGTTTGGAGGAAAGCGACTCCACCC
CGGCCATCGAGTCGGAAGAATACTTCACGCCATCTAGCACCACCAC
TCCCATCCACTCGAACGAAATCCAGCACCGTTCGGATGTGGGCCCA
GGGCGAGCTCCTTGCTTGGACTACGAAAATCAATCGGTGTACTATC
TGTCCTACAAGGCCACGGATGACGAGGGCCGGGGTCAAACGTCGGT
AGTATCGCTCCGGATCACCCTTCTGGATGCGAACGATTCGCCGCCG
GTGTGCGAGAGCCCTCTCTATAGGGCATCGGTCGACGAGGGAGCCA
CCCTATTTGAGCGCCGCTCGTCATCAAAGCCCGCGATCCGGACGT
TATTTCGGAAATTAATTATCGCATAATTGGTAACGAAGCAATTACG
CGCCATTTCGAAATCGACAAACGGTCCGGACAGTTGACCATCTCCA
AGAGTACCGCCCTGGACGTGAACCATCTGAAGTCGGAAAACGTGTT

-continued

CTTCGCCGTGGAGGCAAGCGATGGCCTCTTCACCACCCTGTGCAAC
GTGAACATCACCATCCGGGACGTGAACAACCATGCACCGCAGTTCT
CCCGGGAGCACTATCTTGCCTCGATCGAGGAGAACTTCCCGATTGG
CACCCGAGTCGAACGTTTACAGGCAATCGATTTGGATACCGGCATC
AACGCCGAGATCAGGTACCGCATCCAGCAGGGAAGCTTCGATGACT
TTGCCATCGACAACCAAACCGGGGTGGTGACCATCGCCCGGAAGTT
GGACTACGACCGGAGGAACACCTACCAGATGGAAATAGTGGCAGCG
GATCTGGGCACCCCAAGTCTGTCGGGACAACCACCCTGACGGTGA
GCATCATCAATAGCAACGACAAAGCCCCGTACTTTACGCCGACTAC
TCAGCGGGCGGAAATATCGGAGGATGCGGAAGTGGGAACGTTGGTC
CACACGCTGGTGGCACTCGATCCGGATGTGGCGTCCAGCGAAGCGT
TGGATTATGCGGCAACGGAACCCATCACGGCCGTTGACAAGGACGG
AAAGGAGGTGCGGGACACGGAAGATTTCAAGGACATGTTCCGCATC
GATCGGACCGGAAAGGTGTTCGTCAATCGGAAGCTGCAGCGGGATG
ATTTTGCGGTGATCCGAATCACGGTTCTGGTAACGGACACAACCGC
CCCATCGATTCAGCAGGGCGAAGGTCTCCTCATAATCACAATCATC
GACGTAAATGAAGAGCCACCGCTGTTCGTGCCCCCGTGGACTCCGG
CGGATCCCCGCTACCGGTTCCAGGTGCTGGAGGAACAACCGATCGG
TACCATCCTGACGACGATGCAAGCAACAGATGCCGACTCGACCGTC
GCCGAGTACCGGATGACAGATAACAGCCATTTCGAGATAAACAACA
CAACAGGTCTGATCCGCACCAAAGCCCGTATCGATTACGAGCAAAC
GCCAACGATCCAGTTCAACGTCACCGTGGTGGACACCGGAATCCCG
CAGTTGACGTCCACCGCCGAAGTAACGGTCGACATCATCAACACCA
ACGACAACGATCCGGCCTTCGACGAGCCTGAGTACGAAATGTCCGT
CGTGGAAAACGCACCCACCGGAACGGTTGTGGGCATAGTTTCAGCG
CGGGATGCCGACTCGGGACCGTATGGCCAAATCACCTACTCCCTGG
TCGGTGACCACAGTGCTGCCAGCTTTGCCATCGATCCAGACACCGG
AGTTATCACGGTGCGCGACGGCACAACCTTGGACCGTGAACGGACA
ACGGAAATCGGCCTCACTGCCATTGCCACGGATCGGGCCCCGGATG
GAACCAGCCGGTCGACCACCGCACCGGTTACCATCAAACTGCTGGA
CGAGAACGACAATGTGCCGACCTTCTCGCAGAAGATTTATCACGCC
ACGGTAGCGGAAAATGCGGCACTCAATCCACCGGCAGCAATCTTGC
AGGTTTTGGCCACCGATCCGGACGAGGGCGCTGCTGGGGACGTGAA
ATATAGCATCATCGGTAGCGATATTGAAAACACCTTCCGGCTGGAC
GCAAACTCGGGCATCCTGTATCCGTACGCCAGTTTGCTGGGACTCG
ACGGCAACTATCGCATCCAAATCGAGGCCCGCGATGGCCTAGGATC
CGGACCTCACAGCGATCGGGCTGAAATTAAAATTGAAATACAAAGC
ATCAACCAGCATCGTCCGATTTTCATCATGCCGGCACTGTCCAACG
CAACGGTGGAAATCCCCGAGAATTTAGCGATGACGGATTATCTCGT
GATGACGGTTAAAGCGAACGACAGCGACGAGGGAACGAACGGCAAA
GTTTTGTACCATCTGCAGGTCAACAACCAGAACGTCCAGGAAACGG

-continued

ACGAGTTCATCATCAACGAAATGTCCGGCGAACTGCGCATTCGCAA
GCCCCTCAACCGCAAGAAGCAGGCCCGCTTCGAGTTGATCCTGGTG
GCCCGGGACCAGGGTACCCCTGCGTGGTTCGAAACGCTCCGTTTCC
TCACCGTACTGCTGGTCGACGTCAACGAAAACCACCCGGAGTTTCC
GGACGCCTCAAACCCCTACAGGTTCTTCATCGCCGAGAACAGTCCT
CGGGACATCCGCATCGGTAAAATCCAGGCCTATTACGACACACCCG
ACCCGAAAATCTACTACTACATGATGCTCGGCAACGAGGATGGAGC
GTTCTACGTGGACAAAACCACCGGCGATATCTACACCAACAAAACG
CTGGACCGCGAGGAAGCGGATGTCTACGCTCTCTATATCAAAGCCA
GCAAGAAACAAGACCTGCTGATCACTGAGCGCGATCGGATGATGAT
GTCGACCAAAAAGCTGGAACGCGATAGCACGGTTGCGAAGGTCTGG
ATCACAGTCCTCGATGTCAACGACAATCCCCCGGTCTTTAAACAGG
ACGTTTACTACGCTGGCGTAAGCTCCAAGGCTGCCATCAACGAATT
GGTGACAATTGTCAATGCGACCGATCGAGATCTGGGCGTGAACTCT
ACCATGGAACTGTTCATCAGCGGGTCTTATCTTTACAAATACGGAG
CTACGAAGACAACTGGTAGCATAGTTCCAAGTCCGTTCACTATTTC
CAAGGACGGTCGTATAACTACCGCAAACTACATGGCCGAATATAAC
CAGGACCGTTTCATTCTGGACATTGTAGCAAAAGAGGTGGAATCTC
CTGAGCGAGTTGCCACCACCAAAGTCTACGTCTGGATCTTCAATCC
AGAACAACTAGTGCGTGTGATCCTGTCGAGGCCACCCTCGGAAGTT
CACATGGAGCGAGATGAGATCATATCCGAACTTTCGAATGCCACCC
AGAAGCTGATTATTGTCGATGAGATTCGATACCACGTGGACAGCTT
GGGTCGCATTCGGATGGATTGGTGCGACATGTACTTCCATGCGATC
GATATGAGTTCGCAGACGATCGTGTCGGTAGAGGAGATTCTGCGGG
AGATCGACGCCAAATATGATTTCCTACAGGATTACAATGCCGGCTT
TTCGATCGAGAACGTAGTCCCGGCCTACGCAACCAACGTCCAGGAC
GAGTTCGATTTGGCCCTGGCTGCGATAATCGCCCTGCTGATAGTGC
TGTTTGTCGGTGCCGTAAGCTTCATCGTCCTGTGCTGCTGTCTCAA
ACATTGGGTCATTACGATTCCGAACGAAACCAGAAGAAAGGACGCC
TTGATCAAAAAGCAGATTATCGAAGATTTAAATACGACCGAGAATC
CACTTTGGATCGAGCAAAAACTGAAGCTCTACGAAGAGCAGGAACT
GACGATGCAAGTGTTTTCCGAGCCGGAACTGACGCAACAGCAGCAG
CAGCACCACCACCAACAGCAGTTGAACAGCTCGAACAATACTTCGT
CGTCGTTGGCCAGCCACCAGAACCAGCACCACCATGTGATGCAACA
GCAGGAACAAGCGTTGGTCCTGGGGCTGGATCGGCGGGATTCGTAC
CCGGAATTGTCCCAAGGGGCGGCGATAACACGTACGCCACCATCC
AGCCACGCAATTATGCGTCCAATCTGAGCTCGGTGCTGATGGGCAC
TAGCGGGATTGGTGGCGGCGGCGGTGGCGGAAGCGGAAACGGTGCG
GCCCCGGCAGGCGGACTGAGCGGAGAAATGTCGGATTATGCGACAC
TGCGGAACAGCAGGGCACCCTCGATGTACGAGTTCCGAGGTTCAAC

-continued

CTTCCAGGTACAGCAGCTAAACGGTGGACCCGGCGGTGACCAGCCA
GACTACGTGACGGAACTGATTTAAGAGTAAACAACCTTCGAACAGC
ATCGAACCGTTTTGACCCAACTCAGCCCCAAAAGTGCAACAGTGGA
ACAAACCGTTTTACGCTCTCGAGATGGACAGAGAAAGAGAGAGCAA
CATCACTTTTTGGGTTTTTAGCATAGGATATCATCAGGAGACTAGA
AAGCGGTTTGGAATTTACAAACCAACCGGAATCGCCGGATTGCCAA
TTTGGATTTGTAGAAAATGAATGCTCAATGTGTATGACACCCGAAT
GAAATACTCAAGTGAAGGAAAAGTTCGGAAAGCGATTTTTTAAATT
ACTGATGAGAGGCACAGATTACAAAACACTCTTTGATAGACAATAA
ATAGGAGATATCTTAAAAGGATAGTATTTATGACGGAGGAAGCAAC
ATTGAAGAGATAAACGCACCCGGAGAAAATTGAATCATTCCACACG
CGTACTCATTCCGAGTTTAAGTTGTAATTAATTTAAGTTCACAAAA
ATACATTAACAGATGACCACCAGAATCGAATTCGAGCTATCACGAC
CCGACTCCCCCTTCATTTAAAGGTGCTCGATAGGCAGGGAGCGGAC
GAGTGGCCATTTACTTCACTTGGATACCTCGGCGGTCTGGGGCCAG
CGGCCATTTCGAGCTCATTATAATTTCTCCCATTTTCTGCCAATTA
CCAACGAACGTTCGCTCCACCACACTCTCACACGTGGTCGGTACCG
GCACGCGCTTGAGTTCAACAAATGAATGCAATTAAAAATTACGCAA

AACGAGATTGGGGGAAAAATTCTGCGCACCAAAAGGCATCAATGTG

CAATTTTTCGAGAGAGGCAGGAAGAATATACTGAAAGGGATAAGAG
GTCGAATGTGTCGAAATAGTCGAAATCAAGCATTTTTCGAATGGGT
TTCCCTACGAAAGGCGGAAATCACGAAAGGCTCAACTCGTAAAAGC
TGAAAATATCAAAATACTGAATGGTATTCAAGTCTTCTCTAGTAAA
TCTAGTTTCTAGATGTCATCTTGCAATTCAACTAGCCCGAATGACA
CTAACTTGCAAGCATCTTATCCGAACTTTATGAACATTCAGCTTTT
TTTGTTTCGGCCTTAAGTTGGAATCCTTCGGATGTTACTTTTCTAG
GGTTGCACAGCATCCAGTGAACTGACAATGGCAGTTGAAGAGGCAC
AATTTAATAATTTTGAAAATTACTTACAAATTCGTTGACATAAAAA
AAACTCCGTGAGCTCACTAGAAAATTGTAAAAAATGTCGTTTTGAT

ACAACCTGTATGAAAAATTTGTTTTAACTCAAAACTTATTACGAGT

TTCAAAATCAATTCAGTTCAAATCAGCATCAAACGCCTCATTTCGT
TCAATACTCTTTCGTTGAGAATATTTGTCTACCGTTCGCATTTGGA
ATACAACTTTTATGTATTTCGACCTAAAGACCATTCGACCTATTAT
CGCGATGCGAAACAACCCCCAACTGTGAAGTGAATATCAGCGCGTG

TCGTTCGAAAAAAAAAGACTCAAAAATCCAACCGCCGACGCCAAAC

CGTCGAGGTATCGAGAGTCGAACATTGTAAATAATTAAATCTAGCA
AAATGGATGAGAATATTTAAATTATTAAAAATCAATTATGTTAACG
AGTTTACAGAGACATGCGGGAGGGTGAGGGCTTCGAACAAGGGTCT
GAGGGATTGCATCGCCCTCGGGCTTTAGTTTCGATAGCCAGCCTCG

GTGCGATAAAAAAGGGCTCGACCGATCCAATTCAGCGAGAGCGTCA

-continued

AGAGTAACTGCCCATTTTGTGAAAGGATTGAAAAAGAGGACGACGC
TACGAAAGGACAGCTACCCTCTATCG

The disclosure includes targeting any RNA encoding the *Aedes aegypti* alpha mannosidase protein, the sequence of which is as follows.

>AAEL004389-RB peptide:

(SEQ ID NO: 3)

MTVKIFRRGSARCIGLLSAFVTILLCLYY1SMGQPSNTPTTTATSG

GSSLHKDAALHQKRLSNLHADPHHGAGSNPNANQSWHSWLRNNLNS

INNGGNGKDRPPGLGPEVSDSGGYPDGDGGGGGVGAAAAAVAGSHP

PRFSAKWDECVALEETPTDITTGDEYGNFDFQPEWMKTKEYWDKDF

ESRYEKLQKDPNRPPLKIVWPHSHNDPGWLKTFVNYFQSDSRQILN

LAVTKMPEYNNMSFIWSEISFLQLWWDQAHPTKQRILKKLVKSGRL

EITTGGWVMTDEANAHLYAMVDQLIEGHQWVKTNLNVTPKSGWSID

PFGHGSTVPYLLAASGFEGTIIQRIHYAWKQWFARHRYGDFLWSPY

WRTPSSGLDRKHTLLTHNMPFDIYSIKHSCGPHPFICLNFDFRKIP

GEYTEYSIKAQFITPENIESKADLLMEQYSRTASLFPHNVALIPVG

DDFRYNKDKEMEQQYTNYKKLIDYINENRNKYKAEISFGTPKDYFN

AIKERYDKFPTLKGDFFVYADIFNEGRPAYWSGYFTTRPYYKILSR

ELEHNLRSLEILFTLAFNRARQAGNSNAFKIYEKNYEKMILARRNL

GLFQHHDAITGTSKANVMRDYALRLFESIQDSVKLQEKTIELLVQK

KGTEHNFLIGELERDNFSKLPRKTPLIVTEARSTDFWYNALAQERI

EVVLIRTLTPRVKILDPKGNPMNIQINPVWNITETSSYASRKIIPS

DKEYEIMFVAKLAPLSLTTFTATYDDEFKPKMATLYCNECQDEKNE

IFEIRNKQPGDIQLENFKMRLLFDEQSGFLKSVTKKNMGKQIQCAI

KFAAYKSAQFHSGAYLFKTDPEQRNSEKEILEQYNDMTILITSGPL

ASDVTAIYGPFLAHTVRIFNSNTVLDNGIFIENDIDFEMPPKNRET

ELFMRFVTDIENGASENPEFFSDLNGFQYQKRVKVPSIGIEGNYFP

ITSGAFIQDDKMRLTLLTTHAQGAASLEPGQLEVMLDRRTLYDDYR

GMGEGVVDSRLTRHRFWVVLENIESHSPPLAENPPGPADEPKPAEF

QLPSIFANQLTNGLNYPANLFIVEKYDESNQIELNRAVQLLAAPFP

CDLHILNLRTLTEGNLPLFPSSGALLVLHRQGYDCRIGGEEWNYFC

NNSSSSVSLSSNSNNYKNVDKYNSRLQLFGGVQIEQITGTSLTGLH

PGAPVRSVGDIFLEPMELRTFNLTFVK

The following is a representative cDNA sequence of an mRNA encoding *Aedes aegypti* alpha mannosidase protein.

>AAEL004389-RB cdna: protein coding (SEQ ID NO: 4)

CACTACACCGCCTCGCCATTGCATTTTGGACCGTGGAAAGCCGGATCG

GGGATCTAATCTTGATGTAGCCGATTACCTCCACACCGTACCCACAAA

AAGGATCGCCCGAGTAGAAGAACACTTGAACGTGGCCAGCAGCAGCAG

CTTAGACGTCGCCATCATCTATTCGAAGAACAAAAATCCTAGAAAATG

-continued

TAATTTTCATTCCACCGGCAAGACCAAAGTGAATTAAACTGAACTCCC

CCGGATGTGAAGTCCTGTTTTAGCTTGTTGTGTGAGTGTTTGTGTGTC

AGAAGACAGAGGAAAAATCATAAAGTGTCACATTCTACCGTGAGTGAA

ACGTGAAAGCCGCATCGGCACCCATAAATGAGTGAATATCGCGCGCCG

AAAGTTTAGGGTGGAAAATTGCACCGAGTTGGTGGGGTGCTGCTTCCT

GTTTATTGCCCCATAATCAAGTGCCGAGGGAGCAGAAGCAGAAAAAAG

GTGCCTGCAGCGCCGCAGCATCATGACCGTGAAAATTTTCCGCCGGGG

TTCGGCCCGCTGCATAGGGCTCCTGTCGGCTTTCGTAACCATTTTGCT

GTGCTTGTACTACATCTCGATGGGACAGCCATCAAACACGCCAACGAC

GACCGCCACTTCCGGTGGCTCCTCGCTCCACAAGGATGCTGCCCTGCA

CCAGAAACGATTAAGCAACCTTCATGCAGATCCGCACCACGGCGCCGG

GAGCAATCCGAATGCAAACCAATCCTGGCACAGTTGGCTGCGGAACAA

TCTCAATTCGATCAACAACGGTGGCAACGGCAAGGATCGACCGCCCGG

CCTGGGACCGGAAGTGTCCGACAGTGGAGGCTACCCGGATGGTGATGG

GGGTGGAGGTGGTGTCGGGGCTGCTGCTGCAGCAGTGGCCGGAAGTCA

TCCGCCTCGGTTCAGCGCCAAGTGGGACGAATGTGTCGCACTGGAGGA

AACCCCAACCGATATCACCACCGGCGATGAGTATGGAAATTTCGACTT

CCAGCCCGAATGGATGAAAACAAAGGAATACTGGGACAAGGACTTCGA

GAGCCGTTACGAGAAGCTGCAGAAGGATCCGAACCGACCCCCGTTGAA

GATTGTGGTAGTTCCGCACTCCCATAATGACCCCGGGTGGTTGAAGAC

CTTCGTCAACTACTTCCAGTCGGATTCGAGGCAGATTCTGAACTTGGC

CGTCACTAAGATGCCCGAGTACAACAACATGTCGTTTATATGGAGTGA

GATCAGCTTTCTGCAGTTATGGTGGGATCAAGCACATCCCACCAAGCA

GAGGATATTGAAAAGTTGGTGAAATCAGGTCGTTTGGAGATCACTAC

TGGAGGCTGGGTCATGACGGATGAAGCGAATGCTCATCTTTATGCGAT

GGTTGATCAGCTTATTGAAGGTCATCAATGGGTCAAAACCAATCTGAA

CGTAACTCCGAAGAGCGGATGGAGTATAGATCCTTTTGGACATGGTAG

TACCGTCCCATACTTGTTAGCAGCAAGTGGTTTTGAAGGAACCATCAT

CCAACGGATACACTACGCGTGGAAGCAATGGTTCGCCCGTCATCGATA

CGGAGATTTCCTGTGGAGTCCCTACTGGCGAACACCTTCTAGTGGTCT

GGATCGAAAGCACACTCTCCTGACTCATAACATGCCCTTCGACATCTA

CTCAATCAAACATTCCTGCGGGCCACATCCATTCATCTGCCTTAATTT

CGACTTCCGCAAGATTCCTGGCGAGTATACTGAATACTCGATCAAAGC

TCAGTTCATCACACCGGAAAACATCGAATCCAAAGCTGACCTTCTCAT

GGAGCAATACTCGCGTACTGCTTCCCTGTTCCCTCACAATGTGGCACT

GATTCCCGTTGGAGACGATTTCCGTTACAACAAGGATAAAGAAATGGA

GCAACAGTACACCAACTACAAGAAGCTGATCGACTATATCAACGAGAA

CCGCAACAAGTACAAGGCGGAAATCAGCTTTGGTACTCCGAAGGACTA

CTTCAATGCCATCAAGGAACGCTACGATAAATTCCCGACTTTGAAAGG

AGACTTTTTCGTCTACGCAGACATCTTCAACGAAGGGCGTCCAGCATA

-continued

CTGGTCTGGATATTTCACCACCCGACCGTATTACAAGATTCTCAGTCG

AGAACTCGAACACAACCTTCGTAGCTTGGAAATTCTGTTCACCTTGGC

TTTCAACCGAGCCAGGCAAGCTGGTAATTCCAATGCCTTCAAGATCTA

CGAAAAGAACTACGAGAAGATGATCCTTGCTAGGCGGAACCTAGGCCT

TTTCCAACATCACGATGCCATCACCGGAACGTCCAAAGCCAATGTGAT

GCGAGACTACGCTCTGAGGCTGTTTGAAAGCATCCAAGACTCCGTCAA

GCTTCAAGAGAAAACCATAGAACTGCTCGTCCAGAAGAAAGGCACCGA

GCACAACTTTCTGATCGGAGAGCTGGAGCGGGATAACTTCAGCAAACT

CCCTCGGAAGACTCCTCTGATCGTCACGGAAGCACGGAGTACGGACTT

CGTGGTCTACAACGCCCTCGCGCAAGAACGGATAGAAGTCGTTCTGAT

CAGAACACTGACCCCGCGCGTTAAAATTCTGATCCGAAAGGTAACCC

AATGAACATACAAATCAACCCGGTGTGGAACATCACGGAAACTTCATC

TTACGCATCCCGGAAGATCATTCCCTCGGACAAGGAGTACGAAATCAT

GTTTGTGGCGAAGCTGGCACCTCTTTCGCTAACGACCTTTACGGCCAC

CTATGACGACGAGTTCAAACCGAAGATGGCAACGCTGTACTGCAACGA

GTGCCAAGATGAGAAAAATGAGATATTCGAGATCCGGAACAAACAACC

GGGCGACATTCAGCTGGAAAACTTCAAAATGAGGCTGTTGTTTGATGA

GCAGAGCGGTTTCTTGAAGTCCGTGACTAAGAAAAACATGGGTAAGCA

AATTCAGTGCGCGATCAAGTTTGCCGCGTACAAGAGTGCGCAGTTCCA

CTCTGGTGCGTATCTGTTCAAGACGGATCCGGAGCAAAGGAATTCAGA

GAAAGAGATACTAGAGCAGTATAATGACATGACAATTCTGATAACTTC

CGGCCCACTGGCAAGTGACGTTACAGCAATCTACGGACCATTCCTGGC

TCACACCGTGCGGATATTCAACTCCAACACGGTGCTGGATAACGGAAT

CTTCATCGAGAATGACATCGACTTTGAGATGCCTCCAAAGAACAGGGA

AACAGAACTGTTTATGCGTTTTGTGACAGACATTGAGAATGGGGCTAG

CGAAAACCCTGAATTCTTCTCAGATCTTAATGGATTCCAGTATCAGAA

GCGAGTGAAGGTCCCATCGATCGGTATCGAGGGCAACTACTTCCCTAT

CACCAGCGGGGCATTCATTCAAGATGATAAGATGAGGCTAACTTTGCT

CACGACCCACGCTCAAGGCGCTGCCAGCTTGGAACCCGGACAGCTGGA

AGTAATGCTCGATAGGCGAACTCTGTACGACGACTATCGTGGTATGGG

AGAAGGCGTTGTGGACAGTCGCCTGACCCGACATCGATTCTGGGTTGT

TCTAGAGAATATTGAATCCCATTCGCCACCGTTAGCTGAGAACCCTCC

GGGGCCAGCTGACGAACCAAAACCCGCCGAATTTCAACTGCCTAGTAT

ATTTGCCAATCAGCTCACCAACGGGCTCAACTATCCGGCCAATCTGTT

CATCGTGGAAAAGTACGACGAAAGTAACCAGATAGAGCTGAACCGGGC

GGTCCAACTGCTGGCCGCTCCGTTCCCTGTGATCTCCACATTCTGAA

TCTCCGAACCCTAACCGAGGGTAACCTGCCCCTGTTTCCGTCGAGCGG

AGCTCTGCTGGTTCTACACCGGCAAGGCTACGACTGCCGGATAGGTGG

CGAAGAAGTAGTAAATTATTTTTGTAACAATAGTAGTAGTAGCGTAAG

TCTTAGTAGTAATAGTAACAATTACAAAAATGTAGATAAGTACAATAG

CCGGCTGCAGCTCTTTGGTGGGGTGCAGATCGAACAAATTACCGGCAC

-continued

```
GTCGTTAACGGGTTTGCACCCGGGGGCACCGGTGCGTTCCGTGGGGGA

CATTTTCCTTGAACCGATGGAACTGCGGACGTTCAACCTGACGTTCGT

CAAGTGAGAAGGGGAGAGCGGTGGCGGTGGCGAAGAGACATCAAGCGA

AAGGCTTCCACTGGGTTCCTGGTTTTGGATTGGTTTTAGAAAGTTGTT

ACAAAGGTGGTCCTTGGATAGTTGGCTGGGAATCAGTTCGGGCTAAAG

ATTGGATGTCGGTTTTCTGTGGTCACTTTATGGTGCTTGATTTTAAAA

TACGATTGTAAGATTATCTTTCTTTCATGCCGATACCAGATCCGAGTA

GCTGCATTCTTTTAACGTGAAGGGTCGGCTTGACATAATTTATCCAGG

CATTTGCCCAGAAGATTATTTTTTATGGTGCTATGACCTGCGCCACAA

TGTTACGACAACAAACTCGATTGCCTCTAGTTTCTTGATCGTCCCAAA

CTTCCAAGGTCCTGCTCTACTTGGTCATGCCACCTAAGTCGGAGCGCC

CTTCCCCGGCCGGATTCGAGGTGAACTCCATTTTTGGAGGATTTATCA

CAATTACCCAGCCCATCGTACTCTTTCAGCATTGAAGACTTTCTAGAT

ATATCAAGTTCACCGTAGAGTTGCGCAAGCTATTGGTTCATACGTTTG

CTGGCATGAATTTCACTCAAAAGGCTTCGGTGTGATGCAAACGCAATA

AATTTTTACTCAGACGTTGTTGCAAGGGTTTGAACGGCTTGCTCATTG

GTTGATTCAAACACAGAGTGTAATAAGAAAAACTCAGCAATCACAGAA

AAAGAAAACCGTCTTCGTGAGTCTCGTCTCAGTTCTTAAGCGTTTCCT

ACGCATCGAGATAGGCGATTATTATTCTTGTCAGTAGCAAACCAGCCC

TTAAGCCAGATTTGTTGCTGAAAAGGAACCGCTAAAGACGTTAATCGC

CGACTTCTTGCCGAAATTTCCTATAGTGAGTTCCGTTTGAACTGACAT

TTCTTTTCAACTGCGTACTGCGATCAGAAAAAGGGCTTTCTTGATCGA

TTTGTTACAGGCATTTCCCATAGATATTTAAGCAAATCAGGCTTTAGC

CTGTTTTACTGCTATCTGTAACGTTTTTCCGATGGTTCATTTGATGTG

GAAATTAGTTTAACGGGTTCAATCGCCCTCGTACCTATCCCTTGGGTT

CAATATATGCAAAGAAGTATTAGTGACATGACATGATAGACAGTCATA

ATCAACGAGGGACGATGTATACATCCTATAGGAATACGAATTGCAGAG

ATTGTGACGGGAATAAGTGCGGTGATCCTTCATTAAATCCGAAATGCG

AAAACTGCAGATATAGTGCGCTTATCGGACTTGTAGTTCAGAACCATT

GCATTTGAATTTTTTGCTCTTATTCATTTTACTGTTACTGTGCATAAA

CTAAAGATGCTACAAATAACAGATATCTAAGTCCAAATTGAAAACTGG

CAAGAATGTTAACCACAAACGATGATTTAACGGCCTTTCAAACTGGCA

ACACGTGTAGCGTCGCTGATATCATGGTGAAAATGAAACATTTCAGGA

TGTTCTTAATCACTACCAATTAACACAACATGCTGATCCACGTTGATA

TGTGGGTCAAGTGATATCACCATAGTTGGGTTTGAATGCTTATACAAC

TTTTGAGAAGGTTTTTGTTCCAACATCGATAACTTTTCCTGTGCTTGA

ACTTAGATACTAAGACAGCAAATGTCAAAAATATGAGTCACTTGTGGA

AATGTCTTCTAAGTCATCGCCATTTGTCTCTCATTGCTTCTACAGAAA

TTGAATTCGATCATCAAGACCAAGCTATCAAAACCAGATACGGAATCA

AACATAAGAAAATACAAACGACATCACTCTCTTCCAAGTCTATCCGAT
```

```
ATGTGAATCTCACAAATATTGATCTGAACTAGGGCAACAATTTTTCGA

ATATGGTTTTAAGTTATTTTATTGAAAACAAAAACAGCAGCTGAATCA

TTTCACACGACATAGACGAATCTAAGCAGAACCCCTCAATGTAATCAT

TCCACTTTTTAAGAGAAGAAAAAACAAGAAATCTGGTCCAGTATATAT

TGTTAGATTTATTATTACTGAACAATGCAAAAAATCCCCACAATTTAA

TTTTATGTTCGAAACAAAAAGTGCATGTACCATTCAAGTTGGAAAGAA

ACCTCTTTGCTCTGTATTGTACATACCAAAATCTAGCCCGTAGAATCT

CCTTATCTACATACTTTTGTGATTATAGTGTTAGTGATACGTTTCTTC

CCTGATTCTTCGATTTCTGTTGAAAACTTCCATTCATTTCCATCCTGG

GTCCAATTTAAATACCTCTATCCTTCACAAACGATTTGTTCTTTCAAT

CACAGCTATGATATTTAAAGTTTTAACCACCGTCCAGCAGGATTAGTT

GTTGTCACATAAAATTCCCTACTTTTATTAGTTACTATTTATTAATTA

AATCTAGGATACCCCTAAAATAGTGAGCGTGCGGACGAGCAGCTAATC

CCAAATGAGCCCCTGATATAAACTTGTTTGATATTATCCTACATAATA

ACAACTACGATCAAAAGCGATTTTACAAAGAAAAAAAAGCAAAGCAC

CTACAAGGTAATGCAAAAGAGCAAAACAAAAAAAACTAGCAAAAGATA

GTAAGTAAGCAAATCATCGCGTATGTTTAGAAAAAGGATTAGTTGTTT

TATAAAAGGAAATGAACCTACTGCAGCTAGAAATTAAATTTTAAAGGA

AATAACGGATCAACCGAGCAGGAATGAACAACCATATTCTTAAACTAG

AAGAGAAAGAATTTAACTATTTTATTGTTTATTGTCCCGTCGTTGAAT

CTCCGTTTATTTTACATTGATGTCTAAAGCGTCTGTCAGAAAATGTGT

GACCAGTTGTAGTAAAATTTGTTTTTAACAGTAAATTAACCATTTGTG

CAGCTCGGAAGTTTACAGTTGATTTCATTGCAAAAAGTAATCATTACA

TTTTTTGTTGCAAAATATGTATTGATAGAACAAA
```

In embodiments, the disclosure provides use of an RNA-agent to inhibit translation of an mRNA, or to degrade the mRNA encoding a protein described herein. In embodiments, the RNAi agent is not completely identical in length and sequence to an mRNA expressed by a mosquito. In embodiments, the RNAi agent comprises a segment of RNA that is targeted to an mRNA produced by a mosquito.

In embodiments, any RNA sequences or derivatives thereof described herein can be adapted for use as an RNAi agent, and such sequences may be modified in a variety of ways. In embodiments, the RNAi agent is used as an shRNA. The disclosure includes direct shRNA administration, and administering a vector that encodes the shRNA. In embodiments, the RNAi agent comprises a microRNA, and thus comprises direct administration of a microRNA, and administration of a vector that encodes the microRNA. The term "microRNA" can be used interchangeably with "miR," or "miRNA" to refer to, for example, an unprocessed or processed RNA transcript from an engineered miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 19-25 nucleotide RNA molecule, non-limiting examples of which are described above. This active 19-25 nucleotide RNA molecule is also called the "processed" miRNA gene transcript or "mature" miRNA. Any of these forms of microRNA can be adapted for use in embodiments of this disclosure. Further, in certain embodiments, the RNAi agent may be provided as a synthetic agent, such as a microRNA mimic, short interfering RNA (siRNA), a RNA interference (RNAi) molecule, double-stranded RNA (dsRNA), short hairpin RNA (shRNA), primary miRNAs (pri-miRNAs), small nucleolar RNAs (snoRNAs), a molecule capable of sequence-specific post-transcriptional gene silencing of miRNA, or any combination thereof, where the RNAi agent inhibits expression of the protein. Inhibition of the expression may therefore be achieved by inhibiting translation, transcription, and/or by mRNA degradation. In embodiments, a double-stranded (ds) RNA may be administered to a mosquito, and non-limiting examples of such dsRNA and their efficacy in reducing viral load are demonstrated in the examples.

The disclosure includes, without limitation, modified bacteria that express an RNAi agent described herein, and includes modified mosquitoes that express any such RNAi agent. The disclosure includes isolated RNAi agents, and any type of vector, including but not limited to viral vectors and plasmids that encode and are capable of expressing the RNAi agents in bacterial, and/or in insect cells, particularly mosquito cells. In embodiments, the disclosure provides modified viruses, such as viral particles, such as bacteriophages, that encode the RNAi agent, as well as phagemids that encode the RNAi agent. In embodiments, bacteriophages that are modified to comprise a genome that encodes a RNAi agent described herein are provided.

In certain implementations, an RNAi agent is expressed by a modified mosquito, or is introduced into a mosquito. In embodiments, the modified mosquito is, absent a modification described herein, susceptible of being a vector for one or more viruses, including but not limited to viruses that are DENV, ZIKV, CHIKV, or any combination thereof. In embodiments, a mosquito modified according to this disclosure is an *Aedes aegypti* mosquito. Thus, the disclosure provides for limiting, reducing, replacing, or eradicating susceptible mosquitoes from a mosquito population using modified mosquitoes that express an RNAi agent described herein. In embodiments, use of an RNAi agent as described herein reduces viral load in a mosquito. In non-limiting embodiments, use of an RNAi agent as described herein results in a reduction of DENV viral load in a mosquito. In embodiments, a reduction in viral load occurs in mosquitoes that are free of *Wolbachia* bacteria. In embodiments, a reduction in viral load occurs in mosquitoes that are infected with *Wolbachia*. Determination of viral load can be determined according to techniques that are well known in the art, including but not limited to PCR-based methods.

A mosquito modified to express or comprise an RNAi agent described herein can be modified as such in any suitable way, such as by introducing an episomal element that encodes the RNAi agent into mosquito cells so that the an RNAi agent is expressed. Expression of the RNAi agent may be transient or constitutive, and the expression of an RNAi agent may be inducible, such as being inducible by one or more virally encoded transcription factors. In embodiments, a mosquito chromosome is modified at a larval stage. In embodiments, one or more mosquito totipotent, pluripotent, or multipotent stem cells are modified. In embodiments, only one sex of mosquitoes in a mosquito population is modified. In embodiments, only female mosquitoes are modified. In embodiments, a mosquito chromosome is edited such that it can express an RNAi agent, wherein the modification is made using any suitable chromosome editing technique, including but not limited to CRISPR-based approaches as well as Talens and HEGs. The RNAi agent can be expressed using any promoter that can function in mosquito cells, including but not limited to a recombinantly-introduced promoter that is operably linked to the RNAi agent coding sequence. Additionally an infectious viral agent including but not limited to baculovirus could be used to introduce the gene into the mosquito genome.

In embodiments, the disclosure comprises introducing into mosquitoes an RNAi agent, and optionally a polynucleotide or other element that confers resistance to, for example, a pesticide, and thus comprises a resistance element. Accordingly, borrowing from previous approaches in the agricultural industry to, for example, control the growth of weeds, and/or to promote survival and/or reproduction of plants or the production of viable plant seeds that are resistant to a pest or pesticide or herbicide, the disclosure provides mosquitoes that are resistant to a selection agent via concomitant expression of the RNAi agent and at least one resistant agent that confers resistance to a selection agent. Using this approach, mosquitoes that are not resistant to harbouring viruses, due to a lack of expression of the RNAi agent and the resistance element, can be reduced or eliminated from a mosquito population. In embodiments, the disclosure comprises releasing modified mosquitoes into an environment. In embodiments, releasing the mosquitoes comprises at least a part of performing a gene drive to generate a population of mosquitoes that express or comprise an administered RNAi agent.

In certain embodiments, an RNAi agent is expressed by a modified bacteria. The bacteria may or may not be modified *Wolbachia*, and as such the disclosure includes any modified bacteria that are capable of infecting, and/or living symbiotically or commensally within mosquitoes. In embodiments, the modified bacteria is a bacteria that is adapted to live intracellularly in mosquito cells. Generating bacteria that express an RNAi agent can be performed using any of a wide variety of well-known techniques, such as by introducing a plasmid into the bacteria that encodes the RNAi agent, such that the RNAi agent is expressed by the bacteria. The plasmid may have any feature, such as a selectable marker, or any other component that facilitates its persistence in a bacteria population. The disclosure includes all bacteria, vectors and plasmids, plasmid cloning intermediates, primers, PCR amplifications, PCR amplicons, restriction enzyme digests, which are or could be generated while constructing final vectors or plasmids described herein. A range of bacterial species could be used, including any that naturally infect the mosquito gut and that could be grown and genetically modified.

It will be recognized from the foregoing that the disclosure includes methods for controlling viruses described herein by introducing into mosquitoes any RNAi agent, and further includes introducing an RNAi agent as a component of a pharmaceutical formulation, or as a component of a substance that is consumed by mosquitoes, or by introducing modified bacteria into the mosquitoes, or by introducing a DNA polynucleotide that is capable of expressing the RNAi agent into mosquitoes.

In embodiments, any RNAi agent or derivatives thereof described herein are used as a microRNA. The term "microRNA" can be used interchangeably with "miR," or "miRNA" to refer to, for example, an unprocessed or processed RNA transcript from an engineered miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 19-25 nucleotide RNA molecule, non-limiting examples of which are described above. This active 19-25 nucleotide RNA molecule is also called the "processed" miRNA gene transcript or "mature" miRNA. Any of these forms of microRNA can be adapted for use in embodiments of this disclosure. Further, in certain embodiments, the RNAi agent may be provided as a synthetic agent, such as a microRNA mimic, short interfering RNA (siRNA), a RNA interference (RNAi) molecule, double-stranded RNA (dsRNA), short hairpin RNA (shRNA), primary miRNAs (pri-miRNAs), small nucleolar RNAs (snoRNAs), a molecule capable of sequence-specific post-transcriptional gene silencing of miRNA, or any combination thereof, where the RNAi agent inhibits expression of the protein. Inhibition of the expression may therefore be achieved by inhibiting translation, transcription, and/or by mRNA degradation.

In embodiments, the RNAi agent may be modified to improve its efficacy, such as by being resistant to nuclease digestion. In embodiments, the RNAi agent polynucleotides which comprise modified ribonucleotides or deoxyribonucleotide, and thus include RNA/DNA hybrids. In non-limiting examples, modified ribonucleotides may comprise methylations and/or substitutions of the 2' position of the ribose moiety with an —O— lower alkyl group containing 1-6 saturated or unsaturated carbon atoms, or with an —O-aryl group having 2-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. In embodiments modified nucleotides comprise methyl-cytidine and/or pseudo-uridine. The nucleotides may be linked by phosphodiester linkages or by a synthetic linkage, i.e., a linkage other than a phosphodiester linkage. Examples of inter-nucleoside linkages in the polynucleotide agents that can be used in the disclosure include, but are not limited to, phosphodiester, alkylphosphonate, phosphorothioate, phosphorodithioate, phosphate ester, alkylphosphonothioate, phosphoramidate, carbamate, carbonate, morpholino, phosphate triester, acetamidate, carboxymethyl ester, or combinations thereof.

In non-limiting demonstrations, we used dsRNAs as RNAi agents. This approach achieved reduction in viral load in mosquitoes, as follows.

We used dsRNA targeted to *Aedes aegypti* alpha-mannosidase 2 mRNA as an RNAi agent. The dsRNA comprised the following RNA sequence, along with its complementary strand:

(SEQ ID NO: 5)
GGGAUAACUUCAGCAAACUCCCUCGGAAGACUCCUCUGAUCGUCACGGA

AGCACGGAGUACGGACUUCGUGGUCUACAACGCCCUCGCGCAAGAACGG

AUAGAAGUCGUUCUGAUCAGAACACUGACCCCGCGCGUUAAAAUUCUCG

AUCCGAAAGGUAACCCAAUGAACAUACAAAUCAACCCGGUGUGGAACAU

CACGGAAACUUCAUCUUACGCAUCCCGGAAGAUCAUUCCCUCGGACAAG

GAGUACGAAAUCAUGUUUGUGGCGAAGCUGGCACCUCUUUCGCUAACGA

CCUUUACGGCCACCUAUGACGACGAGUUCAAACCGAAGAUGGCAACGCU

GUACUGCAACGAGUGCCAAGAUGAGAAAAAUGAGAUAUUCGAGAUCCGG

AACAAACAACCGGGCGACAUUCAGCUGGAAAACUUCAAAAUGAGGCUGU

UGUUUGAUGAGCAGAGCGGUUUCUUGAAGUCCGUGACUAAGAAAAACAU

GGGUAAGCAAAUUCAGUGCGCGAUCAAGUUUGCCGCGUACAAGAGUGCG

CAGUUCCACUCUGGUGCGUAUCUGUUCAAGACGGAUCCGGAGCAAAGGA

AUUCAGAGAAAGAGAUACUAGAGCAGUAUAAUGACAUGACAAUUCUGAU

AACUUCCGGCCC

We used dsRNA targeted to *Aedes aegypti* cadherin mRNA as an RNAi. The dsRNA comprised the following RNA sequence, along with its complementary strand:

(SEQ ID NO: 6)
GGGACAUCCGCAUCGGUAAAAUCCAGGCCUAUUACGACACACCCGACC

CGAAAAUCUACUACUACAUGAUGCUCGGCAACGAGGAUGGAGCGUUCU

ACGUGGACAAAACCACCGGCGAUAUCUACACCAACAAAACGCUGGACC

GCGAGGAAGCGGAUGUCUACGCUCUCUAUAUCAAAGCCAGCAAGAAAC

AAGACCUGCUGAUCACUGAGCGCGAUCGGAUGAUGAUGUCGACCAAAA

AGCUGGAACGCGAUAGCACGGUUGCGAAGGUCUGGAUCACAGUCCUCG

AUGUCAACGACAAUCCCCCGGUCUUUAAACAGGACGUUUACUACGCUG

GCGUAAGCUCCAAGGCUGCCAUCAACGAAUUGGUGACAAUUGUCAAUG

CGACCGAUCGAGAUCUGGGCGUGAACUCUACCAUGGAACUGUUCAUCA

GCGGGUCUUAUCUUUACAAAUACGGAGCUACGAAGACAACUGGUAGCA

UAGUUCCAAGUCCGUUCACUAUUUCCAAGGACGGUCGUAUAACUACCG

CAAACUACAUGGCCGAAUAUAACCAGGACCGUUUCAUUCUGGACAUUG

UAGCAAAAGAGGUGGAAUCUCCUGAGCGAGUUGCCACCACCAAAGUCU

ACGUCUGGAUCUUCAAUCCAGAACAACUAGUGCGUGUGAUCCUGUCGA

GGCCACCC

TABLE B

| dsRNA name | Vector-base | Primer | Primer Sequence (5'-3') | dsRNA amplicon size |
|---|---|---|---|---|
| dsAlpha2 | AAEL0 04389 | Forward | taatacgac tcactataG GGATAACTT CAGCAAACT CC (SEQ ID NO: 7) | 649 bp |
|  |  | Reverse | taatacgact cactataGGG CCGGAAGTTA TCAGAAT (SEQ ID NO: 8) |  |
| dsCadherin | AAEL02 3845-RA | Forward | taatacgact cactataGGG ACATCCGCAT CGGTA (SEQ ID NO: 9) | 680 bp |

TABLE B-continued

| dsRNA name | Vector-base | Primer | Primer Sequence (5'-3') | dsRNA amplicon size |
|---|---|---|---|---|
| | | Reverse | taatacgact cactataGGG TGGCCTCGAC AGGAT (SEQ ID NO: 10) | |

In Table B, Lowercase letters=T7 promoter tag. Table B provides the primers that were used to produce the dsRNA constructs described above:

In more detail, RNA silencing of *Aedes aegypti* alpha-mannosidase 2 and *Aedes aegypti* Cadherin87A gene expression was performed using the dsRNA constructs described above. The dsRNAs were synthesized using standard techniques using the primers described above, and injected into *Aedes aegypti* mosquitoes, followed by viral challenge via a blood meal. Control dsRNA constructs were targeted to green fluorescent protein mRNA, which has no known homolog in mosquitoes. Introduction of the dsRNA was performed by adapting known techniques, such as those described in Pan X, et al., Proc Natl Acad Sci USA. 2012 Jan. 3; 109(1):E23-31, the disclosure of which is incorporated herein by reference. Subsequent to viral challenge by dengue virus serotype 2 via a blood meal, mosquitoes were sacrificed and viral load was assessed by PCR using known approaches. PCR was performed on tissue from scarified mosquitoes, which were sacrificed at the indicated time point post infection (DPI). Results in FIG. 11 show reduction in dengue virus load following RNA silencing of the cadherin gene in the mosquito carcass. Specifically, a reduction in dengue virus load following RNA silencing of the cadherin gene in the mosquito carcass 14 days post infection of *Wolbachia*-infected mosquitoes was achieved. These differences demonstrate that the expression of the cadherin gene is assisting with control of dengue virus in the presence of *Wolbachia* infection. Manipulation of Cadherin expression as described herein is therefore expected to strengthen *Wolbachia*-mediated blocking of viruses in mosquitoes.

For alpha mannosidase, we see a reduction in dengue virus load following RNA silencing of the same gene relative to GFP controls in mosquitoes not infected with *Wolbachia* at 10 days post infection in the midgut (FIG. 12). These data indicate that the targeting of alpha-mannosidase expression by as described herein may be expected to render wild type mosquitoes less able to replicate dengue virus in their midguts, thereby reducing transmission rates.

With respect to *Wolbachia*, it is known in the art as an alpha-proteobacterium that lives within the cells of approximately 40% of all insect species[7] and is transmitted from female insects to their offspring[8]. This bacterium has two traits that have made it a candidate for the biological control of mosquito-borne viruses: first, *Wolbachia* can spread rapidly through populations of insects via reproductively manipulating the hose; and second, *Wolbachia* has been found to limit viral replication in insects, a phenotype that is referred to as pathogen 'blocking'[9-11]. Although not naturally found in *A. aegypti*, the bacterium was stably introduced into the species via microinjection over a decade ago[12]. *Wolbachia*'s ability to reduce the transmission potential of DENV, ZIKV and CHIKV[9,13-17] has formed the basis of trial releases into mosquito populations throughout the tropics[18]. *Wolbachia* has successfully spread through *A. aegypti* field populations and remained at high frequencies[18-23]. The impact of these releases on the incidence of human disease is still unknown, but is being assessed[18].

The longevity of *Wolbachia's* use as a disease control agent will depend on the stability of its blocking phenotype over time[24]. For example, the Myxoma virus (MYXV) used against European and Australian rabbits, illustrates how evolutionary change in either the agent or the target can lead to reduced effectiveness. In the years after releases, the virus evolved into less virulent forms[25] and the host evolved resistance[26]. In its native South American rabbits, MYXV was less virulent than in the naïve target populations, suggesting that the evolution of lower virulence was adaptive. Similarly, there is concern that pathogen blocking may evolve to be less effective in the recently infected *A. aegypti* over time, since *Wolbachia* densities and viral blocking tend to be lower in natively infected hosts[1,27-29].

Predicting the long-term stability of *Wolbachia*-mediated blocking is particularly challenging because we do not understand the underlying genetic mechanism. There is some evidence that *Wolbachia* may compete with viruses for host resources[30,31], induce a heightened basal immune response in the host or manipulate host gene expression via the production of small RNAs[32]. None of these effects, however, fully explain the blocking phenotype[24]. Nevertheless, it is most widely observed that stronger blocking is associated with higher *Wolbachia* loads and broader tissue distributions[24,33-35]. While fitness costs for *Wolbachia* infection tend to be mild when measured in controlled laboratory environments, there is evidence that they increase with increasing *Wolbachia* density[19]. Thus, it has been predicted that selection could favour reduced *Wolbachia* density and so blocking[24].

Figure 1:
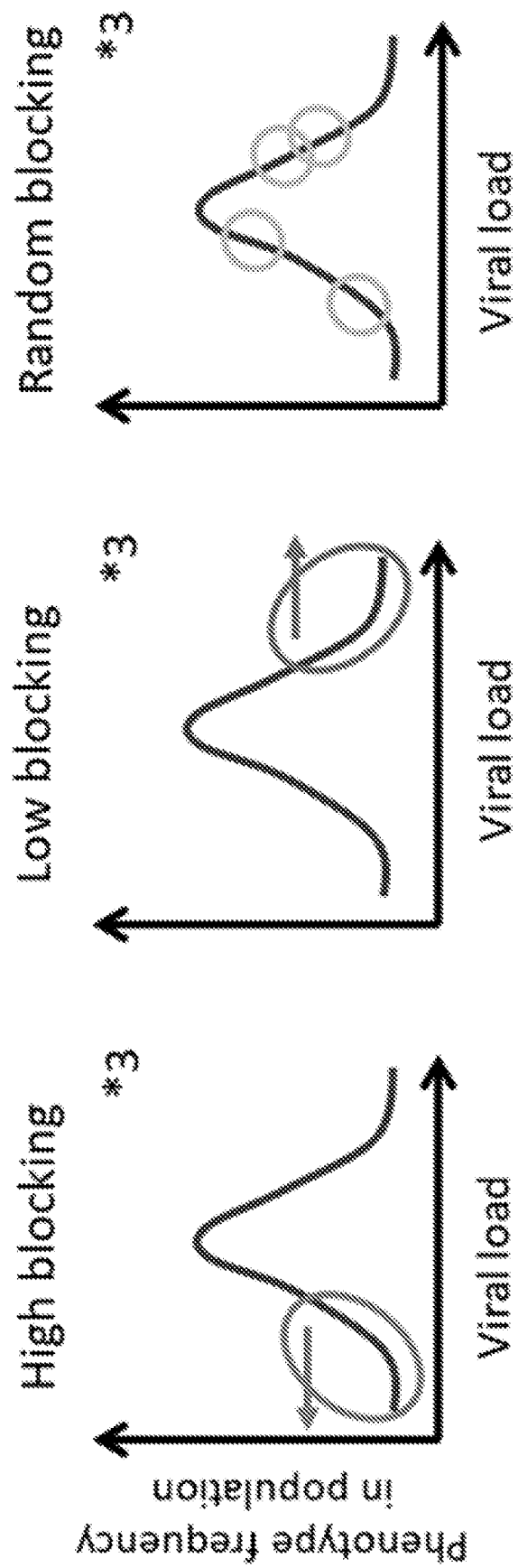
FIG. 1. Experimental design. Selection (High blocking and Low blocking) and control (Random blocking) treatments. Each treatment has 3 replicate lines and all lines are initiated from the same ancestral population of *Wolbachia*-infected *Aedes aegypti* (wMel strain) mosquitoes derived from and repeatedly outcrossed with a population from Queensland, Australia.

In the present disclosure, we used artificial selection to dissect genetic variation in the strength of *Wolbachia*-mediated DENV blocking in *A. aegypti* hosts and its effects on host fitness. Without intending to be constrained by any particular theory, our aim was to determine how *Wolbachia*-based biocontrol could persist by measuring: 1) genetic variation for blocking; 2) the genetic basis for blocking; and 3) how blocking may be maintained by natural selection[24,27]. We selected for high and low DENV blocking alongside a control treatment where mosquitoes were selected at random (FIG. 1). Each treatment was performed on 3 independent lines and all lines were initiated from the same ancestral population of *A. aegypti* mosquitoes from Queensland, Australia that were infected with the wMel strain of *Wolbachia*.

As a result of these tests, and others that are described more fully by the description and figures presented below, the present disclosure provides the aforementioned approaches to use of existing *Wolbachia* strains and/or RNAi agents to controlling viruses, as well as other modified bacteria and approaches that are described above.

From the analysis described herein, we found significant genetic variation for *Wolbachia*-mediated DENV blocking, resulting in a rapid response to selection. Moreover, the magnitude of blocking was correlated with *Wolbachia* density. We reveal that genetic variation in both *A. aegypti* and *Wolbachia* affected blocking strength and that this was strongly associated with mutations in *A. aegypti* genes involved in cell-to-cell adhesion and *Wolbachia* genes involved in translation and bacterial cell wall biosynthesis. Finally, we discovered that populations with high viral blocking had faster population growth, indicating the potential for *Wolbachia*-mediated DENV blocking to be maintained by natural selection within *A. aegypti*.

The following examples are intended to illustrate, but not limit the present disclosure.

Variation in Blocking Strength

To determine the degree of genetic variation for Wolbachia-mediated DENV blocking in A. aegypti we selected upon DENV load for 4 mosquito generations. We found that Wolbachia-mediated DENV blocking evolves rapidly, with significant divergence in phenotypes occurring after just 4 generations (FIG. 2a Mixed effects model: Treatment: Chisq=9.68, df=7, P=0.0079). DENV loads were significantly higher in the lines selected for low blocking relative to lines selected for high blocking (Post-hoc Tukey comparisons: L-H: 0.0021). The Low blocking lines also had significantly higher DENV loads than the Random blocking lines and there was no significant difference between the Random and High blocking lines (Post-hoc Tukey comparisons: L-R: 0.0006, R-H: 0.94). When we compared the treatments over time, we detected a significant interaction between Treatment and Generation (FIG. 2b Mixed effects model. Treatment: Chisq=6.73, df=7, P=0.03; Generation: Chisq=0.1, df=9, P=0.95; Treatment*Generation: Chisq=20.2, df=13, P=0.00046).

Figure 2:
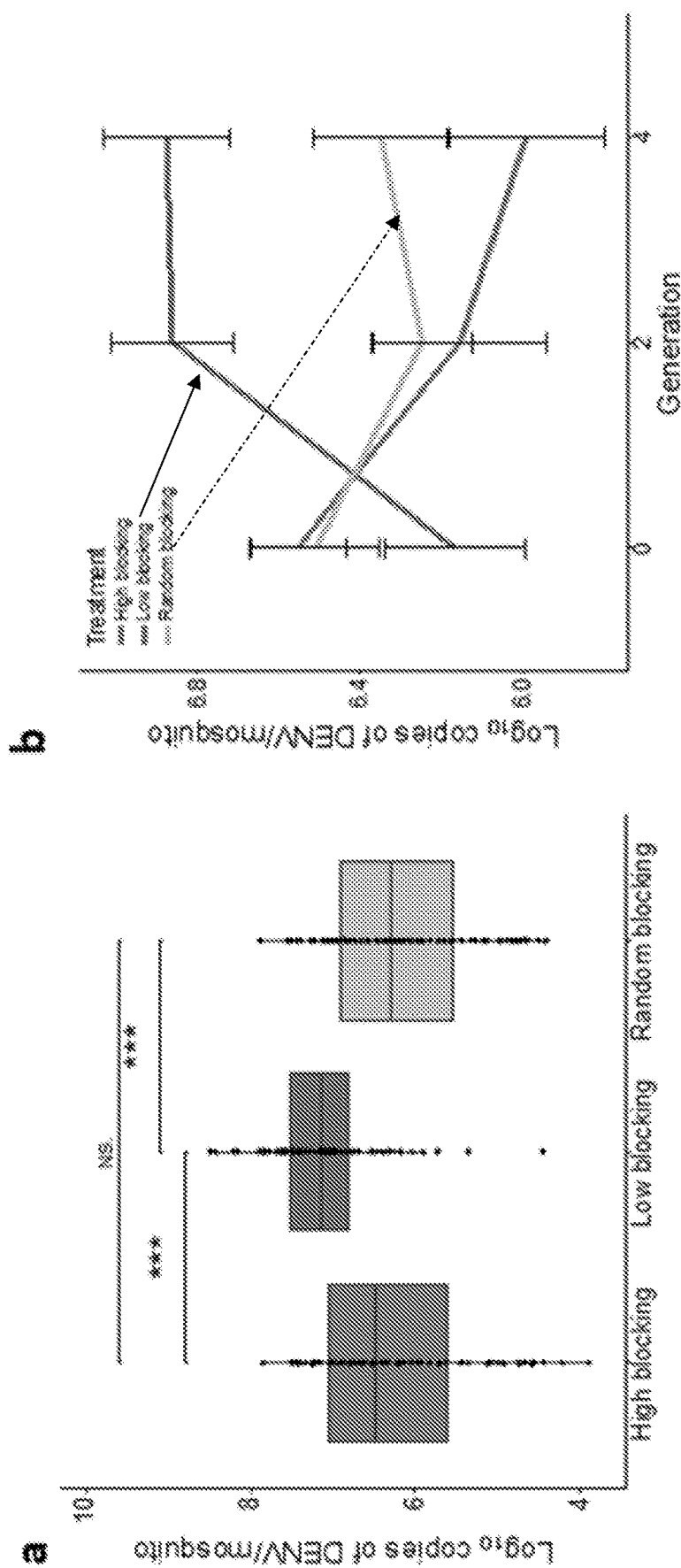
FIG. 2. The rapid evolution of *Wolbachia*-mediated DENV blocking. a, $Log_{10}$ copies of DENV per mosquito in the High, Low and Random blocking treatments after 4 rounds of selection (G4). b, $Log_{10}$ copies of DENV per mosquito in the High, Low and Random blocking treatments every 2 generations of the selection experiment (G0, G2 and G4). Error bars: mean+−1SE. c, $Log_{10}$ copies of DENV per mosquito in the evolved lines either treated with the antibiotic tetracycline to remove *Wolbachia* (Wolb−) or not (Wolb+). These mosquitoes were tested 4 generations after the selection experiment (G8). *$P<0.05$, $P<0.01$, *$P<0.001$.

By removing Wolbachia from each of the evolved lines with the antibiotic tetracycline[36,37] (see FIG. 7 for confirmation of Wolbachia removal), we found no significant difference between mosquito resistance to DENV (FIG. 2c Wolb− Mixed effects model. Treatment: Chisq=1.25, df=7, P=0.53, FDR-corrected P-value=0.69), confirming that the observed variation in DENV load is a result of Wolbachia-mediated DENV blocking (FIG. 2c Wolb+ Mixed effects model. Treatment: Chisq=12.9, df=7, P=0.0016, FDR-corrected P-value=0.0032. Post-hoc Tukey comparisons: H-R: P=0.95. R-L: P<1e−05. H-L: P=2.14e−05). On average, the Low blocking lines were 40% less effective at reducing DENV load than both the High and Random blocking lines.

Wolbachia Density

Several studies have found a heritable basis for Wolbachia density that also correlates with the strength of viral blocking[24,33-35]. Here we examined if Wolbachia density changed in response to selection and played a role in the observed divergence in blocking strength. To increase sensitivity, we removed the ovaries from each mosquito and analysed them separately as they are known to contain disproportionately high densities of Wolbachia[38]. In agreement with the literature, we identify a negative correlation between Wolbachia density and DENV load across the evolved lines within the bodies of mosquitoes (FIG. 3 Linear regression. Wolbachia density: t=−2.9, df=7, P=0.02*, $R^2$=0.55). We found this relationship only in the bodies of mosquitoes, not in the ovaries (FIG. 8, Linear regression. Wolbachia density: t=−0.56, df=7, P=0.59, $R^2$=0.042).

Genetic Basis of Variation

To understand the genetic basis underlying the phenotypic divergence observed in blocking, we sequenced pools of 90 individual mosquitoes from the ancestral populations and from each evolved line at generation 4 and looked for single nucleotide polymorphisms (SNPs) that were significantly differentiated between treatments by performing pairwise whole genome Cochran-Mantel-Haenszel (CMH) tests. Our threshold for significance was set as the smallest P-value from comparing the Random blocking populations with the ancestral population. This is based upon the assumption that differences between these populations are due to drift and so are false positives. Based upon this threshold, we found significantly differentiated SNPs in both A. aegypti and Wolbachia genomes when we compared the lines from the High blocking and Low blocking treatments, suggesting that both organisms played a role in determining the phenotypic extremes of Wolbachia-mediated DENV blocking (FIG. 4 and FIG. 5).

In A. aegypti there were approximately ~60 genes with significant SNPs differentiating the High and Low lines (Table 1). There was a particularly significant peak on chromosome 1 (labelled as region A in FIG. 4a), containing SNPs in two neighbouring genes. One of these genes is predicted to encode the cadherin-87A protein (AAEL023845), a glycoprotein that is involved in cell-to-cell adhesion[39]. We found 84 SNPs within this gene that have P-values smaller than the significance threshold. The other gene encodes alpha-mannisodase 2a (AAEL004389), an enzyme in the N-glycan biosynthesis pathway that plays a role in the functioning of cadherin[40,41]. We found 15 SNPs within this genes that have P-values smaller than the significance threshold. By performing CMH tests between the other evolved populations and the ancestral population, our data indicate that mutations associated with strong blocking in these genes that were frequent in the High blocking populations were also frequent in the ancestral and Random blocking populations. This is because, the peak of differentiation in these genes is not present in comparisons between the High, Random and ancestral populations. Consistent with this, SNPs in region A were also highly differentiated when we compare the Low blocking populations with the Random blocking populations (FIG. 4c) and the ancestral population (FIG. 4e). This therefore indicates that there could be a fitness advantage of stronger blockers, such that this phenotype is at a high frequency in the base population prior to directional selection and is maintained in the Random treatment in the absence of directional selection.

We find two main regions where the High and Random blocking populations differ, denoted B and C (FIG. 4). Although SNPs in these regions show some differentiation with the Low blocking populations, they are likely to be less critical for blocking strength since both High and Random blocking populations show strong blocking and differ in this region.

Far fewer differentiated SNPs were identified in the Wolbachia genome overall (see FIG. 5), consistent with its recent introduction into A. aegypti by microinjection[21]. By comparing lines from the High blocking and Low blocking treatments (FIG. 5a) we found differentiated SNPs within 14 genes that can be grouped by function (Table 1). These include: 1) five genes involved in mRNA translation; 2) four genes involved in the biosynthesis of the bacterial cell wall component, peptidoglycan; 3) three genes involved in stress response; and 4) two genes involved in changing DNA topology. Interestingly, each of the 5 genes involved in mRNA translation are either tRNAs or are translational machinery that bind tRNAs, suggesting some functional role of tRNAs. It has been shown that bacterial tRNAs can be reduced into small noncoding RNAs that can control gene expression[42,43]. We hypothesised that Wolbachia could be producing tRNA-derived small noncoding RNAs that alter host gene expression. We performed a BLAST search of the tRNA-Ile gene against the A. aegypti genome and found 95% identity across 20nt near the 3' end of the tRNA with the host gene DnaJ (AAEL005305). This gene encodes a heat shock protein in the 40 family (Hsp40) that is a co-chaperone in the Hsp70 chaperone function.

Implications of Variation on A. aegypti Fitness

To understand how the observed genetic variation could shape the evolution of Wolbachia-mediated viral blocking and so the stability and success of Wolbachia as a biological control strategy, we investigated the impact of the different genotypes on mosquito fitness. More specifically, we calculated the population growth rate (r) of the mosquitoes in the absence of DENV infection to estimate how fitness varies with blocking strength. We did this by measuring: median time to pupation, adult sex ratio, female adult survival, the number of eggs laid per female over 3 bloodmeals and the rate of egg laying. We combined these data to construct Leslie matrix models to gain an estimate of population growth rate (r) for each line[44]. To check the robustness of our findings we tested models across two values of larval survival to adulthood that were chosen to represent the low and high extremes (43% and 92%, respectively) of the range observed experimentally.

We found a significant negative correlation between DENV load per mosquito and *A. aegypti* population growth rate (r) across both low larval survival (FIG. 6 Mixed effects regression controlling for hatch order. $Log_{10}$ copies of DENV per mosquito: Chisq=9.13, df=4, P=0.0025) and high larval survival estimates (FIG. 10 Mixed effects regression controlling for hatch order. $Log_{10}$ copies of DENV per mosquito: Chisq=8.38, df=4, P=0.0038), indicating that *Wolbachia*-mosquito combinations that were better at blocking DENV were also inherently more fit. The strongest determinant of this difference appears to be the rate of egg laying.

It will be recognized from the foregoing that *Wolbachia* is a promising biological control agent against viruses including dengue, Zika and chikungunya within populations of the mosquito *Aedes aegypti*. Our aim was to understand the potential for the *Wolbachia*-mediated pathogen blocking phenotype to persist over evolutionary time. We used artificial selection as a tool to tease apart genetic variation for this trait in *A. aegypti* and investigate its relationship with mosquito fitness.

The response to selection was rapid and resulted in populations that differed in blocking strength by 40%. This demonstrates that even within a single mosquito population carrying a recently introduced *Wolbachia* infection, there remains substantial genetic variation for blocking. The implications for field release are two-fold. First, blocking may exhibit phenotypic variation when the *Wolbachia* strains are crossed into local mosquito populations around the globe in preparation for local field releases. Second, the presence of variation means that blocking may evolve in the *Wolbachia* and/or *A. aegypti* populations through time post release.

Little is known about the selection pressures that may shape the evolutionary trajectory of *Wolbachia*-mediated DENV blocking in *A. aegypti*[27]. Empirical evidence shows that high *Wolbachia* density and thus blocking strength tend to associate with large fitness costs[19] and so it has been predicted that selection could favour reduced blocking over time[24]. Here, we found that *Wolbachia* density did correlate with blocking strength, however *Wolbachia*-infected populations with stronger blocking had a higher intrinsic growth rate. For the first time, these data indicate the potential for stronger blockers to outcompete weaker blockers. Consistent with this result, populations selected for high blocking strength were most similar in phenotype and genotype to the Random and ancestral populations that were not subject to artificial selection. This suggests that high blocking genotypes are maintained at a high frequency in populations by natural selection. Published data on blocking stability 1 year after release trials in Australia show that blocking strength in field-collected mosquitoes was maintained at levels similar to the original lines[38]. Thus, our results suggest that this outcome is likely due to the maintenance of blocking by natural selection rather than a lack of genetic variation.

In the present disclosure, blocking strength was strongly associated with SNPs in the *A. aegypti* genome, demonstrating the capacity for the species to shape the nature of blocking. Crucially, the removal of *Wolbachia* from the evolved populations abolished the differences in blocking strength between the selection treatments, indicating that the genetic changes in the mosquito genome are only relevant in the context of an interaction with *Wolbachia*. This finding is in contrast with a recent study in *Drosophila melanogaster* natively infected with *Wolbachia* that found that evolutionary changes in host resistance explained most of the host adaptation to *Drosophila* C virus[45]. When we examined the identity of the genes within the *A. aegypti* genome that contained SNPs important for blocking strength, we found that they were not members of classical innate immune pathways (Toll, Imd, RNAi or JAK-STAT)[46]. Instead, they include a gene that encodes the glycoprotein cadherin that is important for cell-to-cell adhesion[39] and an alpha-mannisodase 2a enzyme which is involved in the N-glycan biosynthesis pathway. *Wolbachia* has been previously shown to alter the expression of genes involved in cell-cell adhesion and the N-glycan biosynthesis pathway[47]. The N-glycan biosynthesis pathway may be important as it is involved for the functioning of cadherin[40,41] and cadherin could be mediated in *Wolbachia's* interaction with the host cytoskeleton. Interestingly, DENV has been shown to bind cadherin within the cell[48] and could be a point of interaction between *Wolbachia*, DENV and *A. aegypti*. It is possible that *Wolbachia* is affecting the success of DENV by altering key molecules the virus needs for binding and entry into cells. Recent experimental work has suggested that the main impact of *Wolbachia* is at the point of limiting viral replication[49] however this work was carried out in cell culture where expression of genes involved in cell-to-cell adhesion could be altered.

Here, we used artificial selection as a tool to dissect genetic variation important for *Wolbachia*-mediated DENV blocking in *A. aegypti*. These findings highlight the capacity for both *Wolbachia* and *A. aegypti* genomic variation to affect blocking strength. Promisingly, however, strong blocking was also associated with a faster mosquito population growth rate, which may help to drive and maintain the strength of *Wolbachia* mediated viral blocking over the long-term. At a mechanistic level, we have highlighted changes in the *A. aegypti* genome that most likely modify the strength of blocking and from a series of changes in the *Wolbachia* genome, developed a possible model to explain the symbiont's mode of action. Understanding mechanism may help evaluate and improve the specificity of *Wolbachia* strains against diverse mosquito genetic backgrounds.

Supplementary Information

Ethics Statement

All experiments in this study that utilised a human volunteer for mosquito blood-feeding were carried out at Monash University, Melbourne (Australia). The Monash University Human Research Ethics Committee gave ethical approval for the use of human volunteers to provide bloodmeals to mosquitoes that were not infected with DENV (permit CF11/0766-2011000387). One volunteer was used throughout this study and provided written consent prior to the study.

Mosquitoes

We used a population of *Aedes aegypti* mosquitoes that were infected with the wMel (wMel.F) line of *Wolbachia* bacteria[21,53] and had since been maintained in the lab for 33 generations. Every 3 generations these mosquitoes were outcrossed with *Wolbachia*-free mosquitoes collected from Queensland, Australia to maintain standing genetic variation that represent a natural population[24,53]. During outcrossing, females from the lab population were only allowed to mate with males from the natural populations to ensure the maternal transmission of *Wolbachia*. This is because *Wolbachia* bacteria are passed through the maternal line.

Dengue Virus

An isolate of DENV serotype 3 from Cairns was used in this study[54,55]. Virus was grown within C6/36 *Aedes albopictus* cells following standard methods[24]. C6/36 cells were grown at 26° C. in T175 tissue culture flasks containing 25 ml RPMI 1640 media (Life Technologies, Carlsbad, CA) supplemented with 10% Fetal Bovine Serum (FBS, Life Technologies), 2% HEPES (Sigma-Aldrich, St. Louis, MO) and 1% Glutamax (Life Technologies). Prior to infection, C6/36 cells were grown to 80% confluency. At this point, the media was replaced with 25 ml RPMI supplemented with 2% FBS (Life Technologies), 2% HEPES (Sigma-Aldrich, St. Louis, MO) and 1% Glutamax (Life Technologies). 20 µl of a solution containing DENV-3 was added. After 7 days, the cells were scraped off and suspended in the media. The media was collected and centrifuged at 3200 g for 15 minutes at 4° C. The supernatant was then taken and frozen in single-use aliquots at −80° C. and all experiments in this paper were conducted using these aliquots. Viral titre was measured from a thawed aliquot by: 1) mixing 20 ul of the aliquot with 200 ul of TRIzol reagent (Invitrogen); 2) extracting the RNA following the manufacturer's protocol and treating with DNAse; and 3) quantifying DENV RNA using RT-qPCR (see section "Dengue virus quantification"). This was repeated 3 independent times for the same aliquot and an average viral titre was calculated.

Dengue Virus Quantification

The quantification of DENV was carried out via RT-qPCR using the LightCycler 408 (Roche). We used the TaqMan Fast Virus 1-Step Master Mix (ThermoFisher) in a total reaction volume of 10 ul, following the manufacturer's instructions[24]. The primers and probes used for DENV detection are listed in Table 3. The protocol for the RT-qPCR was as previously documented[56]. Data were analysed using absolute quantification where DENV copy number per sample was calculated from a reference curve. This reference curve was made up of known quantities of the genomic region of DENV that the primers amplify. This genomic region had previously been cloned into the pGEM-T plasmid (Promega, Madison, WI) and transformed into *Escherichia coli*[56]. After growing this transformed *E. coli* in liquid LB overnight at 37° C. we then extracted the plasmid using the PureYield Plasmid Midiprep System kit (Promega) and linearized the plasmid by restriction digest. We then purified the plasmid using phenol-chloroform extraction, resuspended in 20 ul of UltraPure distilled water (Invitrogen) and quantified the plasmid by Qubit. A dilution series of $10^7$, $10^6$, $10^5$, $10^4$, $10^3$, $10^2$ and $10^1$ copies of the viral genomic fragment were created and frozen as single-use aliquots. All assays measuring DENV load in this study used these identical aliquots and 3 replicates of the dilution series was run on every 96-well plate to create a reference curve for DENV quantification. For a given analysis, replicates from each population being compared were equally represented on each 96-well plate.

Wolbachia Quantification

We measured the density of *Wolbachia* as the number of genome copies relative to the number of mosquito genome copies via multiplex qPCR on the LightCycler 408 (Roche)[57]. We used the LightCycler480 Probes Master mix (2× concentration from Roche) in a total reaction volume of 10 ul. The list of primers and probes are given in Table 3. The protocol for the RT-qPCR was as previously documented[56]. Basic relative quantification was used with mosquito genome copies as the reference and *Wolbachia* genome copies as the target. For a given analysis, replicates from each population being compared were equally represented on each 96-well plate.

Selection Experiment

We performed a bi-directional artificial selection experiment where we selected for increased and decreased DENV load (Low and High blocking treatments, respectively). We also included a random control treatment that imposed no directional selection (Random blocking treatment, see FIG. 1a). Each treatment was replicated with 3 independent lines[58] generated randomly from the same ancestral population of mosquitoes.

Each generation, mosquito eggs were hatched in trays (30×40×8 cm). Each tray contained 2 L of autoclaved RO water and 150-200 larvae. Larvae were fed with common fish food each day (Tetramin®, Melle, Germany). Rearing was performed under controlled conditions of temperature (26±2° C.), relative humidity (~70%) and photoperiod (12: 12, light:dark). After pupation, pupae were placed within 30×30×30 cm cages in cups containing autoclaved RO water for eclosion. At this stage, cages housed ~450 individuals each. Dental wicks soaked in 10% sucrose water were placed in each cage as a food source. When mosquitoes were 5-7 days old the females from each line were allowed to blood-feed on the arm of a human volunteer in a random order. The next day, blood-engorged females were placed into separate cups enclosed with mesh (see FIG. 1b). Each cup contained filter paper sitting in autoclaved RO water to provide an oviposition site for female mosquitoes. A small petri dish was placed over the water to reduce the risk of mosquitoes drowning. A cotton wool ball soaked in 10% sucrose water was placed on top of the mesh as a food source for each cup.

After 4 days, the filter paper was collected from each female and dried following standard protocol for short-term egg storage[59]. Each set of eggs were numbered according to which mosquito they came from. On the same day, between 40 and 70 females from each population of the High and Low blocking lines were anaesthetised with $CO_2$ and injected with 3,903 genomic copies of dengue in 69 nl of RPMI media (5.66E−05 genomic copies/ml), delivered at a speed of 46 nl/sec into the thorax using a pulled glass capillary needle and a manual microinjector (Nanoject II, Drummond Sci.). The mosquitoes were then returned to individually labelled cups. Egg collection was done prior to injection to prevent the vertical transmission of DENV[60].

At 7 days post infection, females were anaesthetised with $CO_2$ and were placed into individual wells in a 96-well plate containing 50 µl of extraction buffer. These samples were then homogenised with a 3 mm glass bead. Extraction buffer was made up of squash buffer (10 mM Tris pH 8.2, 1 mM EDTA, 50 mM NaCl)[61] with proteinase k at a concentration of 12.5 µl/ml (Bioline). Samples were then incubated for 5 minutes at 56° C. and 5 minutes at 95° C. We then examined DENV load per mosquito using RT-qPCR (see "Dengue virus quantification"). This method was used for rapid phenotype determination of a large number of samples.

Mosquitoes where then ranked in order from: the lowest DENV load in the High blocking lines; the highest DENV load in the Low blocking lines; and using a random number generator in the random line. Eggs from the top 20 mosquitoes were placed into separate cups of autoclaved RO water. The next day, larvae were then taken from cups in rank order until ~200 larvae were collected for each replicate population. This was done to impose the strongest selection pressure as possible whilst ensuring enough mosquitoes will be reared for selection to also be possible in the subsequent generation. At this point, the passage protocol was repeated. In total, 4 rounds of selection were completed.

Dengue Virus Load and *Wolbachia* Density at Generation 4

After 4 rounds of selection, mosquitoes from each line were reared and injected with DENV as above (see "Selection protocol"). Seven days after injection, 30 mosquitoes from each line were dissected to separate the ovaries and the bodies since ovaries contain large densities of *Wolbachia* and could potentially mask patterns with DENV load in the body (ref?). Dissections were performed in 1× phosphate buffered saline (PBS) on a glass slide under a microscope using dissecting needles. Dissecting needles were soaked in 80% ethanol between each dissection and needles were changed between each line. Each body was placed into 1.5 ml tubes containing 200 ul of TRIzol reagent. Ovaries from 20 mosquitoes per line were collected in the same way. Each sample was then homogenised with a 3 mm glass bead and stored at −80° C. until used.

RNA was extracted from the TRIzol reagent for each mosquito body following the manufacturer's protocols and resuspended in 25 ul of UltraPure distilled water. Each sample was then treated with DNAse 1 (Sigma Aldrich) by adding 1 ul of enzyme and 2.9 ul of buffer. Samples were incubated at 37° C. for 30 minutes and then 75° C. for 10 minutes. At this point DENV quantification was carried out by RT-qPCR (see "Dengue load quantification"). DNA was also extracted from the TRIzol reagent for each mosquito body and set of ovaries collected following the manufacturer's protocols and resuspended in 25 ul of UltraPure distilled water. The density of *Wolbachia* was then measured using qPCR (see "*Wolbachia* quantification").

Dengue Virus Load Over Time

At generations 0, 2 and 4 of the selection experiment, additional mosquitoes from the High and Low selection treatments and mosquitoes from the Random treatment were injected with DENV as above (see "Selection protocol") to assess the change in DENV load over time. Seven days after injection, 10 mosquitoes from each line were collected in 1.5 ml tubes containing 200 ul of TRIzol reagent and homogenised with a 3 mm glass bead per sample. Samples were stored at −80° C. prior to RNA extraction. RNA extraction and DNAse treatment was carried out as above (see "Dengue virus load and *Wolbachia* density at generation 4") and DENV load was quantified by RT-qPCR (see "Dengue load quantification").

Role of *Wolbachia* in Phenotypic Differences

To confirm that the divergence in DENV load between treatments was as a result of *Wolbachia*-mediated DENV blocking, we treated subpopulations of each line with the antibiotic tetracycline for 2 generations. Each generation, 10% sucrose water containing tetracycline (1.25 mg/ml tetracycline at pH 7 with unbuffered Tris) was given to adult mosquitoes[36] via dental wicks and replaced every 2 days. Control subpopulations of each line were kept separately and fed 10% sucrose at the adult stage. We then reared the lines for another generation with no antibiotic treatment to allow microbiota recovery. This is important since the microbiome can have important roles in mosquito resistance to arboviruses and we only want to measure the effect of *Wolbachia*-mediated protection[57]. We transferred 100 ml of the larval rearing water from each control line to the corresponding antibiotic-treated line to re-introduce the resident microbiota, as is standard procedure[37]. This water was checked for egg and/or larval contamination. The following generation of mosquitoes (now 4 generations since the selection experiment) were then reared and injected with DENV as above (see "Selection experiment") and collected in 1.5 ml tubes containing 200 ul of TRIzol reagent after 7 days of infection. These samples were homogenised with a 3 mm glass bead each and stored at −80° C. RNA and DNA extraction was carried out as above ("Dengue virus load and *Wolbachia* density at generation 4"); DENV load was quantified by RT-qPCR (see "Dengue virus quantification"); and *Wolbachia* density was quantified by qPCR (see *Wolbachia* quantification).

Genomic Analysis

DNA was extracted from 90 individual mosquitoes from each line at generation 4. We extracted DNA using the TRIzol reagent (Invitrogen), using a modified version of the manufacturer's protocol with additional washing steps using phenol, chloroform and isoamylalcohol (please see corresponding step-by-step methods on Nature's Protocol Exchange). The DNA of 90 mosquitoes were pooled in equal volumes per line and sequenced using Illumina HiSeq3000 with 150 bp paired-end reads.

FastQC version 0.11.4 was used with default settings to check the quality of the raw reads. To minimise false positives, Trimmomatic version 0.36 was used to trim the 3' ends if quality was <20 and reads were discarded if trimming resulted in reads that were <50 bp in length. We mapped the resulting reads to the *Wolbachia* genome AE017196.1 and the *Aedes agypti* assembly Liverpool AGWG-AaegL5 using BWA ALN and checked for quality using qualimap version 2.2.1. Indel realignment was completed using GATK version 3.8.0. Duplicates were removed using picard version 2.17.8 and poor quality maps were removed using samtools 1.6 and filtering via hex flags. The quality was checked using qualimap. SNPs were called using popoolation2. SNPs were then filtered with a minimum coverage of 20 and a maximum of 200.

Mosquito Life History Traits and Fitness Estimation

To understand the impact of the strength of *Wolbachia*-mediated DENV blocking on mosquito fitness, we estimated population growth rates by calculating the per capita intrinsic rate of natural increase (r) for mosquitoes based on life history data collected from 3 replicate populations from each line of the High blocking, Low blocking and the Random blocking treatments. These included the median time to pupation, adult sex ratio, female adult daily survival over 3 bloodmeals and the size and timing of egg clutches over 3 bloodmeals. We used these data to construct Leslie matrix models to then calculate the asymptotic growth rate for a population that behaved exactly as the individuals observed in our experimental cages (models constructed as previously detailed[44]). This approach assumes density independence and has been used as a holistic estimate to capture mosquito fitness in previous studies on mosquito fitness[44,62,63].

We hatched offspring from mosquitoes at the end of the selection experiment by submerging eggs into autoclaved RO water and placing them into a vacuum chamber for 40 min. We used this reduced oxygen environment to induce synchronous hatching within each line to reduce variation in our data. We hatched lines in 3 batches, with each treatment being equally represented in each batch so that hatch time could be controlled for statistically. Hatched larvae were then separated from unhatched eggs and kept in trays of ~200 larvae in 2 L of autoclaved RO water and were fed daily with Tetramin tablets. The number of larvae that had pupated each day was recorded per tray and pupae were placed in cups of water within separate 30×30×30 cm cages for each replicate.

Once all pupae emerged to the adult stage we measured sex ratio. We then transferred 60-80 females and 40 males per replicate into 20×20×30 cm cages to allow for mating. We gave each population the chance to take a blood meal from a human volunteer for 15 minutes in a randomised order. The next day, we placed cups containing filter paper and autoclaved RO water into each cage to allow for female oviposition. We changed these cups after 5 and 8 days and counted the number of eggs laid per cage within each time interval to get a measure of egg laying rate. We repeated this process 2 more times, resulting in 3 bloodmeals. After each bloodmeal we removed females that did not feed so that we had an accurate estimate of eggs laid per female. At the same time, we also measured female mortality, removing dead mosquitoes each day and censoring mosquitoes that we removed because they did not feed[64]. Accidental deaths and escapees were also recorded and censored from the dataset.

Eggs were counted using an adapted version of a previously determined protocol[65]. This protocol uses a high-resolution colour scanner to take images of the egg papers and creates a reference curve of manually counted eggs and the total area of an image that is black using ImageJ (see FIG. 9). We used an Epson V39 flatbed scanner with 4800×4800 dpi. To ensure the highest accuracy, we carefully used a wet paintbrush to spread out eggs on the filter paper and we scanned each filter paper as they were still moist such that the eggs did not desiccate and change shape. Prior to using the ANALYZE: ANALYZE PARTICLES function in ImageJ, we set the upper threshold for calculating the total particle area at 95 by using the IMAGE:ADJUST:THRESHOLD function.

Statistical Analysis

All statistical analyses were performed in R version 3.2.2 (www.r-project.org/) and are listed in Table 2, along with sample sizes. Where multiple comparisons were made on a single data-set, P-values were corrected using the false discovery rate (FDR) method. For all mixed-effects models, the significance of fixed effects and their interactions was performed by sequentially removing model terms. Models were fit by maximum likelihood and statistically compared using a likelihood ratio test. We analysed $\log_{10}$ copies of DENV per mosquito at generation 4 using mixed-effects models that included Treatment as a fixed effect and line, batch of RNA extraction and RT-qPCR plate as random factors (FIG. 2a). We analysed $\log_{10}$ copies of DENV per mosquito over time using mixed-effects models that included Treatment, Generation and their interaction as fixed effects and line, batch of RNA extraction and RT-qPCR plate as random factors (FIG. 2b). We measured the effect of Wolbachia presence on $\log_{10}$ copies of DENV per mosquito by using a mixed effects model in the presence of Wolbachia and another in the absence of Wolbachia (FIG. 2c). Both models included Treatment as the fixed effect and line, batch of RNA extraction and RT-qPCR plate as random factors.

Figure 3:
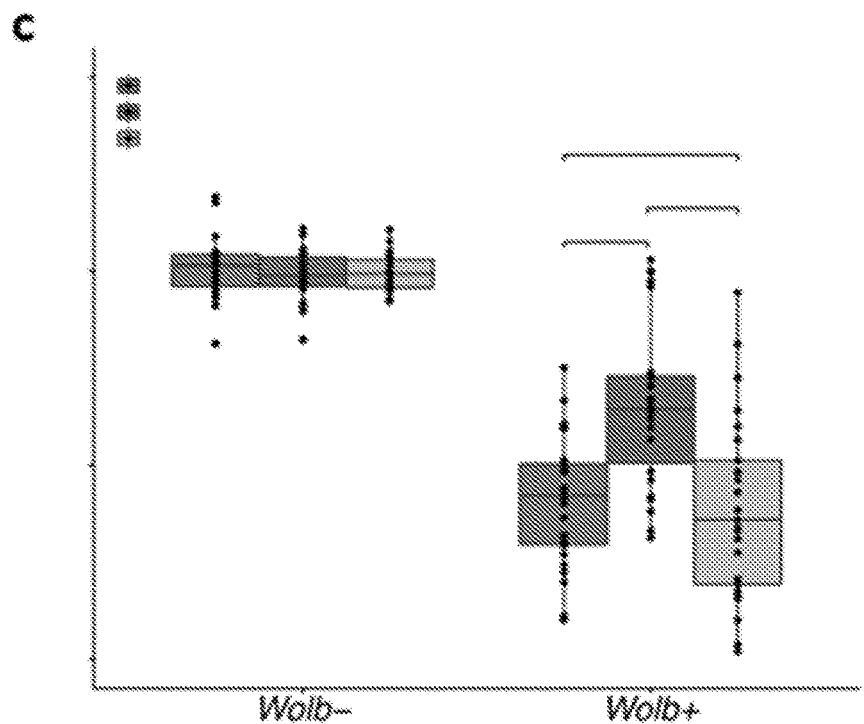
FIG. 3. *Wolbachia* density correlates with strength of DENV blocking. The correlation between the $log_{10}$ copies of DENV per mosquito and the density of *Wolbachia* cells.
Figure 3:
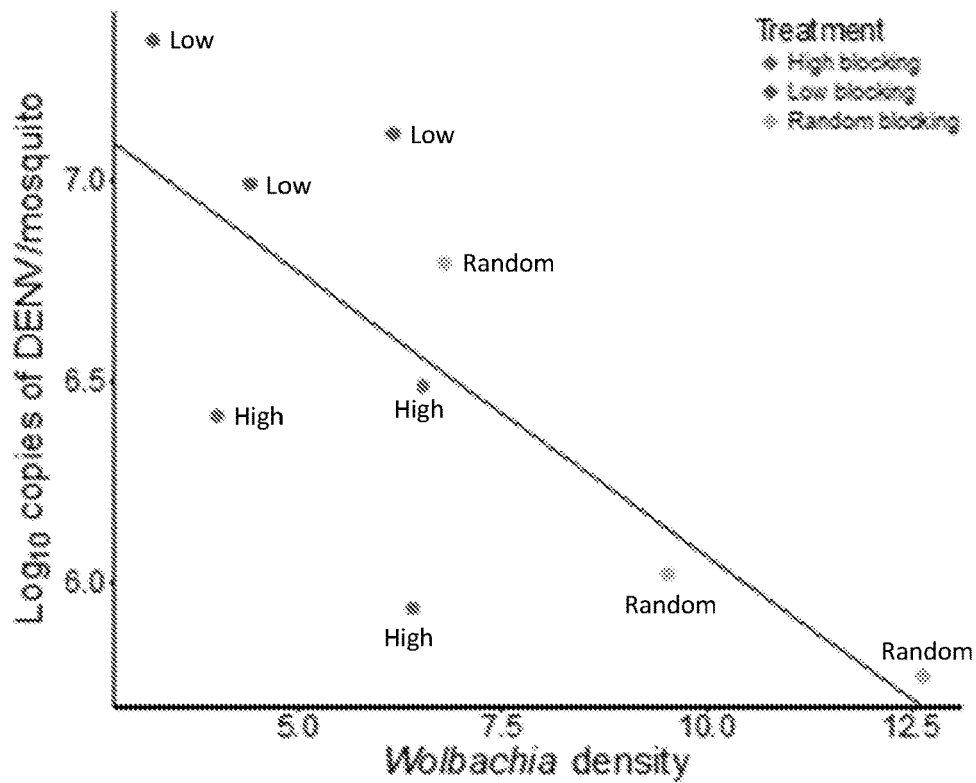

We tested for the presence of a significant correlation between $\log_{10}$ copies of DENV per mosquito and Wolbachia density in the bodies and the ovaries using a linear regression model with Wolbachia density as the independent variable (FIG. 3 and FIG. 8, respectively). We tested for a correlation between $\log_{10}$ copies of DENV per mosquito and the intrinsic growth rate of each line (with low and high juvenile survival separately) using mixed effects regression models including growth rate as the response variable, DENV load as the fixed effect and the order of hatching batch as a random effect (FIG. 6 and data FIG. 10). For each correlation, points represented population averages for each independent line. We calculated the reference curve for the automated counting of eggs using a linear regression model with the total particle area as the dependent variable and the number of eggs as the independent variable (FIG. 9).

REFERENCES

This reference listing is not intended to be an indication that any of the references are material to patentability.

1 Bhatt, S. et al. The global distribution and burden of dengue. *Nature* 496, 504-507, doi:10.1038/nature12060 (2013).
2 Dengue vaccine: WHO position paper—July 2016. *Wkly Epidemiol Rec* 91, 349-364 (2016).
3 World Health Organization. Global Strategy for dengue prevention and control, 2012-2020. (2012).
4 Moyes, C. L. et al. Contemporary status of insecticide resistance in the major *Aedes* vectors of arboviruses infecting humans. *PLoS Negl Trop Dis* 11, e0005625, doi:10.1371/journal.pntd.0005625 (2017).
5 Flores, H. A. & O'Neill, S. L. Controlling vector-borne diseases by releasing modified mosquitoes. *Nat Rev Microbiol* 16, 508-518, doi:10.1038/s41579-018-0025-0 (2018).
6 Guzman, M. G. et al. Dengue: a continuing global threat. *Nat Rev Microbiol* 8, S7-16, doi:10.1038/nrmicro2460 (2010).
7 Zug, R. & Hammerstein, P. Still a host of hosts for *Wolbachia*: analysis of recent data suggests that 40% of terrestrial arthropod species are infected. *PLoS One* 7, e38544, doi:10.1371/journal.pone.0038544 (2012).
8 Shropshire, J. D., On, J., Layton, E. M., Zhou, H. & Bordenstein, S. R. One prophage WO gene rescues cytoplasmic incompatibility in. *Proc Natl Acad Sci USA* 115, 4987-4991, doi:10.1073/pnas.1800650115 (2018).
9 Moreira, L. A. et al. A *Wolbachia* symbiont in *Aedes aegypti* limits infection with dengue, Chikungunya, and Plasmodium. *Cell* 139, 1268-1278, doi:10.1016/j.cell.2009.11.042 (2009).
10 Teixeira, L., Ferreira, A. & Ashburner, M. The bacterial symbiont *Wolbachia* induces resistance to RNA viral infections in *Drosophila melanogaster*. *PLoS Biol* 6, e2, doi:10.1371/journal.pbio.1000002 (2008).
11 Hedges, L. M., Brownlie, J. C., O'Neill, S. L. & Johnson, K. N. *Wolbachia* and virus protection in insects. *Science* 322, 702, doi:10.1126/science.1162418 (2008).
12 Gloria-Soria, A., Chiodo, T. G. & Powell, J. R. Lack of Evidence for Natural *Wolbachia* Infections in *Aedes aegypti* (Diptera: Culicidae). *J Med Entomol*, doi: 10.1093/jme/tjy084 (2018).
13 Dutra, H. L. et al. *Wolbachia* Blocks Currently Circulating Zika Virus Isolates in Brazilian *Aedes aegypti* Mosquitoes. *Cell Host Microbe* 19, 771-774, doi:10.1016/j.chom.2016.04.021 (2016).
14 Tan, C. H. et al. wMel limits zika and chikungunya virus infection in a Singapore *Wolbachia*-introgressed *A. aegypti* strain, wMel-Sg. *PLoS Negl Trop Dis* 11, e0005496, doi:10.1371/journal.pntd.0005496 (2017).
15 Ye, Y. H. et al. *Wolbachia* Reduces the Transmission Potential of Dengue-Infected *Aedes aegypti*. *PLoS Negl Trop Dis* 9, e0003894, doi:10.1371/journal.pntd.0003894 (2015).

16 Aliota, M. T., Peinado, S. A., Velez, I. D. & Osorio, J. E. The wMel strain of *Wolbachia* Reduces Transmission of Zika virus by *Aedes aegypti*. *Sci Rep* 6, 28792, doi:10.1038/5rep28792 (2016).

17 Aliota, M. T. et al. The wMel Strain of *Wolbachia* Reduces Transmission of Chikungunya Virus in *Aedes aegypti*. *PLoS Negl Trop Dis* 10, e0004677, doi:10.1371/journal.pntd.0004677 (2016).

18 O'Neill, S. L. The Use of *Wolbachia* by the World Mosquito Program to Interrupt Transmission of *Aedes aegypti* Transmitted Viruses. *Adv Exp Med Blot* 1062, 355-360, doi:10.1007/978-981-10-8727-1_24 (2018).

19 Hoffmann, A. A., Ross, P. A. & Rašić, G. *Wolbachia* strains for disease control: ecological and evolutionary considerations. *Evol Appl* 8, 751-768, doi:10.1111/eva.12286 (2015).

20 Hancock, P. A., White, V. L., Ritchie, S. A., Hoffmann, A. A. & Godfray, H. C. Predicting *Wolbachia* invasion dynamics in *Aedes aegypti* populations using models of density-dependent demographic traits. *BMC Biol* 14, 96, doi:10.1186/s12915-016-0319-5 (2016).

21 Walker, T. et al. The wMel *Wolbachia* strain blocks dengue and invades caged *Aedes aegypti* populations. *Nature* 476, 450-453, doi:10.1038/nature10355 (2011).

22 Jiggins, F. M. The spread of *Wolbachia* through mosquito populations. *PLoS Biol* 15, e2002780, doi:10.1371/journal.pbio.2002780 (2017).

23 Schmidt, T. L. et al. Local introduction and heterogeneous spatial spread of dengue-suppressing *Wolbachia* through an urban population of *Aedes aegypti*. *PLoS Biol* 15, e2001894, doi:10.1371/journal.pbio.2001894 (2017).

24 Terradas, G., Allen, S. L., Chenoweth, S. F. & McGraw, E. A. Family level variation in *Wolbachia*-mediated dengue virus blocking in *Aedes aegypti*. *Parasit Vectors* 10, 622, doi:10.1186/s13071-017-2589-3 (2017).

25 Di Giallonardo, F. & Holmes, E. C. Viral biocontrol: grand experiments in disease emergence and evolution. *Trends Microbiol* 23, 83-90, doi:10.1016/j.tim.2014.10.004 (2015).

26 Longdon, B. et al. The causes and consequences of changes in virulence following pathogen host shifts. *PLoS Pathog* 11, e1004728, doi:10.1371/journal.ppat.1004728 (2015).

27 Bull, J. J. & Turelli, M. *Wolbachia* versus dengue: Evolutionary forecasts. *Evol Med Public Health* 2013, 197-207, doi:10.1093/emph/eot018 (2013).

28 Rancès, E., Ye, Y. H., Woolfit, M., McGraw, E. A. & O'Neill, S. L. The relative importance of innate immune priming in *Wolbachia*-mediated dengue interference. *PLoS Pathog* 8, e1002548, doi:10.1371/journal.ppat.1002548 (2012).

29 Ant, T. H., Herd, C. S., Geoghegan, V., Hoffmann, A. A. & Sinkins, S. P. The *Wolbachia* strain wAu provides highly efficient virus transmission blocking in *Aedes aegypti*. *PLoS Pathog* 14, e1006815, doi:10.1371/journal.ppat.1006815 (2018).

30 Caragata, E. P. et al. Dietary cholesterol modulates pathogen blocking by *Wolbachia*. *PLoS Pathog* 9, e1003459, doi:10.1371/journal.ppat.1003459 (2013).

31 Bhattacharya, T., Newton, I. L. G. & Hardy, R. W. *Wolbachia* elevates host methyltransferase expression to block an RNA virus early during infection. *PLoS Pathog* 13, e1006427, doi:10.1371/journal.ppat.1006427 (2017).

32 Mayoral, J. G. et al. Wolbachia small noncoding RNAs and their role in cross-kingdom communications. *Proc Natl Acad Sci USA* 111, 18721-18726, doi:10.1073/pnas.1420131112 (2014).

33 Osborne, S. E., Iturbe-Ormaetxe, I., Brownlie, J. C., O'Neill, S. L. & Johnson, K. N. Antiviral protection and the importance of *Wolbachia* density and tissue tropism in *Drosophila simulans*. *Appl Environ Microbiol* 78, 6922-6929, doi:10.1128/AEM.01727-12 (2012).

34 Martinez, J. et al. Symbiont strain is the main determinant of variation in *Wolbachia*-mediated protection against viruses across *Drosophila* species. *Mol Ecol* 26, 4072-4084, doi:10.1111/mec.14164 (2017).

35 Chrostek, E. et al. *Wolbachia* variants induce differential protection to viruses in *Drosophila melanogaster*: a phenotypic and phylogenomic analysis. *PLoS Genet* 9, e1003896, doi:10.1371/journal.pgen.1003896 (2013).

36 Dobson, S. L. & Rattanadechakul, W. A novel technique for removing *Wolbachia* infections from *Aedes albopictus* (Diptera: Culicidae). *J Med Entomol* 38, 844-849 (2001).

37 McMeniman, C. J. et al. Stable introduction of a life-shortening *Wolbachia* infection into the mosquito *Aedes aegypti*. *Science* 323, 141-144, doi:10.1126/science.1165326 (2009).

38 Frentiu, F. D. et al. Limited dengue virus replication in field-collected *Aedes aegypti* mosquitoes infected with *Wolbachia*. *PLoS Negl Trop Dis* 8, e2688, doi:10.1371/journal.pntd.0002688 (2014).

39 Halbleib, J. M. & Nelson, W. J. Cadherins in development: cell adhesion, sorting, and tissue morphogenesis. *Genes Dev* 20, 3199-3214, doi:10.1101/gad.1486806 (2006).

40 Gu, J. et al. Potential roles of N-glycosylation in cell adhesion. *Glycoconj J* 29, 599-607, doi:10.1007/s10719-012-9386-1 (2012).

41 Xu, Y. et al. N-Glycosylation at Asn 402 Stabilizes N-Cadherin and Promotes Cell-Cell Adhesion of Glioma Cells. *J Cell Biochem* 118, 1423-1431, doi:10.1002/jcb.25801 (2017).

42 Miyoshi, K., Miyoshi, T. & Siomi, H. Many ways to generate microRNA-like small RNAs: non-canonical pathways for microRNA production. *Mol Genet Genomics* 284, 95-103, doi:10.1007/s00438-010-0556-1 (2010).

43 Maute, R. L. et al. tRNA-derived microRNA modulates proliferation and the DNA damage response and is downregulated in B cell lymphoma. *Proc Natl Acad Sci USA* 110, 1404-1409, doi:10.1073/pnas.1206761110 (2013).

44 Ohm, J. R. et al. Fitness consequences of altered feeding behavior in immune-challenged mosquitoes. *Parasit Vectors* 9, 113, doi:10.1186/s13071-016-1392-x (2016).

45 Martins, N. E. et al. Host adaptation to viruses relies on few genes with different cross-resistance properties. *Proc Natl Acad Sci USA* 111, 5938-5943, doi:10.1073/pnas.1400378111 (2014).

46 Terradas, G., Joubert, D. A. & McGraw, E. A. The RNAi pathway plays a small part in *Wolbachia*-mediated blocking of dengue virus in mosquito cells. *Sci Rep* 7, 43847, doi:10.1038/srep43847 (2017).

47 Hughes, G. L. et al. *Wolbachia* infections in Anopheles gambiae cells: transcriptomic characterization of a novel host-symbiont interaction. *PLoS Pathog* 7, e1001296, doi:10.1371/journal.ppat.1001296 (2011).

48 Colpitts, T. M. et al. Use of a tandem affinity purification assay to detect interactions between West Nile and dengue viral proteins and proteins of the mosquito vector. *Virology* 417, 179-187, doi:10.1016/j.virol.2011.06.002 (2011).

49 Thomas, S., Verma, J., Woolfit, M. & O'Neill, S. L. *Wolbachia*-mediated virus blocking in mosquito cells is dependent on XRN1-mediated viral RNA degradation and 50 Pan, X. et al. The bacterium *Wolbachia* exploits host innate immunity to establish a symbiotic relationship with the dengue vector mosquito *Aedes aegypti*. *ISME J* 12, 277-288, doi:10.1038/ismej.2017.174 (2018).
51 Xi, Z., Ramirez, J. L. & Dimopoulos, G. The *Aedes aegypti* toll pathway controls dengue virus infection. *PLoS Pathog* 4, e1000098, doi:10.1371/journal.ppat.1000098 (2008).
52 Ferguson, N. M. et al. Modeling the impact on virus transmission of *Wolbachia*-mediated blocking of dengue virus infection of *Aedes aegypti*. *Sci Transl Med* 7, 279ra237, doi:10.1126/scitranslmed.3010370 (2015).
53 Hoffmann, A. A. et al. Successful establishment of *Wolbachia* in *Aedes* populations to suppress dengue transmission. *Nature* 476, 454-457, doi:10.1038/nature10356 (2011).
54 Ye, Y. H. et al. Evolutionary potential of the extrinsic incubation period of dengue virus in *Aedes aegypti*. *Evolution* 70, 2459-2469, doi:10.1111/evo.13039 (2016).
55 Ritchie, S. A. et al. An explosive epidemic of DENV-3 in Cairns, Australia. *PLoS One* 8, e68137, doi:10.1371/journal.pone.0068137 (2013).
56 Ye, Y. H. et al. Comparative susceptibility of mosquito populations in North Queensland, Australia to oral infection with dengue virus. *Am J Trop Med Hyg* 90, 422-430, doi:10.4269/ajtmh.13-0186 (2014).
57 Jupatanakul, N., Sim, S. & Dimopoulos, G. The insect microbiome modulates vector competence for arboviruses. *Viruses* 6, 4294-4313, doi:10.3390/v6114294 (2014).
58 Kawecki, T. J. et al. Experimental evolution. *Trends Ecol Evol* 27, 547-560, doi:10.1016/j.tree.2012.06.001 (2012).
59 Zheng, M. L., Zhang, D. J., Damiens, D. D., Lees, R. S. & Gilles, J. R. Standard operating procedures for standardized mass rearing of the dengue and chikungunya vectors *Aedes aegypti* and *Aedes albopictus* (Diptera: Culicidae)—II—Egg storage and hatching. *Parasit Vectors* 8, 348, doi:10.1186/s13071-015-0951-x (2015).
60 Joshi, V., Mourya, D. T. & Sharma, R. C. Persistence of dengue-3 virus through transovarial transmission passage in successive generations of *Aedes aegypti* mosquitoes. *Am J Trop Med Hyg* 67, 158-161 (2002).
61 Yeap, H. L. et al. Assessing quality of life-shortening *Wolbachia*-infected *Aedes aegypti* mosquitoes in the field based on capture rates and morphometric assessments. *Parasit Vectors* 7, 58, doi:10.1186/1756-3305-7-58 (2014).
62 Paaijmans, K. P., Imbahale, S. S., Thomas, M. B. & Takken, W. Relevant microclimate for determining the development rate of malaria mosquitoes and possible implications of climate change. *Malar J* 9, 196, doi:10.1186/1475-2875-9-196 (2010).
63 Irvin, N., Hoddle, M. S., O'Brochta, D. A., Carey, B. & Atkinson, P. W. Assessing fitness costs for transgenic *Aedes aegypti* expressing the GFP marker and transposase genes. *Proc Natl Acad Sci USA* 101, 891-896, doi:10.1073/pnas.0305511101 (2004).
64 Joy, T. K., Arik, A. J., Corby-Harris, V., Johnson, A. A. & Riehle, M. A. The impact of larval and adult dietary restriction on lifespan, reproduction and growth in the mosquito *Aedes aegypti*. *Exp Gerontol* 45, 685-690, doi:10.1016/j.exger.2010.04.009 (2010).
65 Mains, J. W., Mercer, D. R. & Dobson, S. L. Digital image analysis to estimate numbers of *Aedes* eggs oviposited in containers. *J Am Mosq Control Assoc* 24, 496-501, doi:10.2987/5740.1 (2008).

TABLE 1

*Wolbachia* genes containing SNPs differentiated between Low and High blocking.

| # SNPs | min P-value | max P-value | Gene ID | Gene | Function | |
|---|---|---|---|---|---|---|
| 3 | 4.55E−61 | 5.32E−10 | WD_0095 | | D-alanine-D-alanine ligase Peptidoglycan biosynthesis | yellow |
| 53 | 1.77E−54 | 0.00669482 | WD_Wp23SB | 23SB | 23S ribosomal subunit Translation | blue |
| 1 | 9.35E−43 | N.A. | WD_1128 | murF | UDP-N-acetylmuramoylalanyl-D-glutamyl-2,6-diaminopimelate-D-alanyl-D-alanyl ligase Peptidoglycan biosynthesis | yellow |
| 7 | 8.16E−37 | 2.38E−25 | WD_tRNA-Ile-1 | tRNA-Ile-1 | tRNA Translation | blue |
| 34 | 6.50E−21 | 0.03017372 | WD_Wp16SA | 16SA | 16S ribosomal subunit Translation | blue |
| 2 | 1.12E−18 | 2.43E−06 | WD_0928 | dnaK | Chaperone protein, Stress response | grey |
| 2 | 1.03E−16 | 1.31E−16 | WD_0112 | gyrB | DNA gyrase, B subunit DNA topological change | green |
| 4 | 3.18E−14 | 2.21E−07 | WD_0227 | | Elongation factor Tu family protein Translation | blue |
| 4 | 5.45E−12 | 3.12E−05 | WD_0527 | uppS | Undecaprenyl diphosphate synthase Peptidoglycan biosynthesis | yellow |
| 1 | 1.77E−10 | N.A. | WD_tRNA-Thr-1 | tRNA-Thr-1 | tRNA Translation | blue |
| 1 | 5.49E−08 | N.A. | WD_0154 | uvrC | Excinuclease ABC, C subunit DNA repair in response to damage | grey |
| 1 | 1.62E−07 | N.A. | WD_0613 | | Glycosyl transferase, group 1 family protein Peptidoglycan biosynthesis | yellow |

TABLE 1-continued

Wolbachia genes containing SNPs differentiated between Low and High blocking.

| # SNPs | min P-value | max P-value | Gene ID | Gene | Function | |
|---|---|---|---|---|---|---|
| 2 | 1.83E−07 | 0.04057723 | WD_1202 | gyrA | DNA gyrase, A subunit DNA topological change | green |
| 3 | 4.43E−06 | 6.28E−05 | WD_0317 | lon | ATP-dependent protease La Degradation of misfolded proteins | grey |

TABLE 2

Statistical analyses and sample sizes

| Figure | Statistical test | Sample size | | | |
|---|---|---|---|---|---|
| 2a | DENV load by treatment (G4) Mixed effects model Random effects: Line; RNA extraction batch; and RT-qPCR plate Treatment: Chisq = 9.68, df = 7, P = 0.0079** Post-hoc Tukey comparisons: L-H: 0.0021** L-R: 0.0006*** R-H: 0.94 | | # Mosquitoes | | | |
| | | H1 | 30 | | |
| | | H2 | 2 | | |
| | | H3 | 30 | | |
| | | L1 | 13 | | |
| | | L2 | 30 | | |
| | | L3 | 30 | | |
| | | R1 | 29 | | |
| | | R2 | 30 | | |
| | | R3 | 30 | | |
| 2b | DENV load by treatment over time (G0, G2, G4) Mixed effects model Random effects: Line; RNA extraction batch; and RT-qPCR plate Treatment: Chisq = 6.73, df = 7, P = 0.03* Generation: Chisq = 0.1, df = 9, P = 0.95 Treatment * Generation: Chisq = 20.2, df = 13, P = 0.00046*** Post-hoc Tukey comparisons: | | # Mosquitoes | | | |
| | | Generation: | 0 | 2 | 4 |
| | | H1 | 10 | 10 | 10 |
| | | H2 | 10 | 10 | 10 |
| | | H3 | 10 | 10 | 10 |
| | | L1 | 10 | 10 | 2 |
| | | L2 | 10 | 10 | 10 |
| | | L3 | 10 | 10 | 10 |
| | | R1 | 10 | 10 | 10 |
| | | R2 | 10 | 10 | 10 |
| | | R3 | 10 | 10 | 9 |
| 2c | DENY load with & without Wolbachia (G8) Wolb− Mixed effects model Random effects: Line; RNA extraction batch; and qPCR plate Treatment: Chisq = 1.25, df = 7, P = 0.53, FDR-corrected P-value = 0.69 Values were removed from the Wolb− treatment if Wolbachia showed (i.e. incomplete tetracycline curing). Wolb+ Mixed effects model Random effects: Line; RNA extraction batch; and qPCR plate Treatment: Chisq = 12.9, df = 7, P = 0.0016** FDR-corrected P-value = 0.0032** Post-hoc Tukey comparisons: H-R: P = 0.95 R-L: P < 1e−05*** H-L: P = 2.14e−05 *** | | # Mosquitoes | | | |
| | | Treatment: | Wolb− | Wolb+ | |
| | | H1 | 9 | 9 | |
| | | H2 | 9 | 9 | |
| | | H3 | 5 | 8 | |
| | | L1 | 9 | 9 | |
| | | L2 | 8 | 9 | |
| | | L3 | 9 | 8 | |
| | | R1 | 4 | 9 | |
| | | R2 | 9 | 9 | |
| | | R3 | 8 | 7 | |
| 3 | Correlation of DENY load and Wolbachia density in A. aegypti bodies (G4) Linear regression model Wolbachia density: t = −2.9, df = 7, P = 0.02*, R² = 0.55 Log₁₀ copies of DENV are averages of data presented in FIG. 2a. Wolbachia density was measured from the same mosquitoes. | | # Mosquitoes | | | |
| | | H1 | 29 | | |
| | | H2 | 29 | | |
| | | H3 | 30 | | |
| | | L1 | 13 | | |
| | | L2 | 30 | | |
| | | L3 | 29 | | |
| | | R1 | 29 | | |
| | | R2 | 30 | | |
| | | R3 | 29 | | |
| 6 | Correlation of Aedes aegypti population growth rate (G5) with DENY load (G4) with low juvenile survival Population growth rate data was calculated using Leslie matrix models using data from 3 replicate populations per line per treatment (same as data FIG. 10) with juvenile survival estimated at 43%. Mixed effects regression model Random factors: hatch order | | # Larvae | | | |
| | | Tray: | 1 | 2 | 3 |
| | | H1 | 200 | 206 | 203 |
| | | H2 | 194 | 187 | 190 |
| | | H3 | 201 | 191 | 199 |
| | | L1 | 192 | 193 | 189 |
| | | L2 | 192 | 191 | 191 |
| | | L3 | 211 | 187 | 222 |

TABLE 2-continued

Statistical analyses and sample sizes

| Figure | Statistical test | Sample size | | | |
|---|---|---|---|---|---|
| | $Log_{10}$ copies of DENV per mosquito: Chisq = 9.13, df = 4, P = 0.0025**  FDR-corrected P-value: 0.0038** | R1 | 194 | 208 | 213 |
| | | R2 | 201 | 194 | 189 |
| | | R3 | 213 | 214 | 200 |
| | | | # Mosquitoes | | |
| | | Cage: | 1 | 2 | 3 |
| | | H1 | 86 | 79 | 66 |
| | | H2 | 82 | 65 | 73 |
| | | H3 | 35 | 80 | 64 |
| | | L1 | 90 | 59 | 39 |
| | | L2 | 81 | 80 | 72 |
| | | L3 | 79 | 83 | 73 |
| | | R1 | 78 | 78 | 77 |
| | | R2 | 81 | 67 | 78 |
| | | R3 | 87 | 82 | 54 |
| Extd data 1 | *Wolbachia* densities of samples treated or untreated with tetracycline (G8) *Wolbachia* density was measured from the same mosquitoes as in FIG. 2c. | Same as FIG. 2c | | | |
| Extd data 2 | Correlation of DENV load and *Wolbachia* density in *A. aegypti* ovaries (G4) Linear regression model *Wolbachia* density: t = −0.56, df = 7, P = 0.59, $R^2$ = 0.042 $Log_{10}$ copies of DENV are averages of data presented in FIG. 2a. *Wolbachia* density was measured from the same mosquitoes. | # Mosquitoes H1 11 H2 11 H3 12 L1 6 L2 11 L3 12 R1 12 R2 12 R3 12 | | | |
| Extd data 3 | Reference curve for estimation of egg numbers Linear regression model Egg number: t value = 49.426, df = 2, P = 3.08e−15 ***, $R^2$ = 0.995 Y = 183.1547X−8596.8768 | 14 egg papers of variable density | | | |
| Extd data 4 | Correlation of *Aedes aegypti* population growth rate (G5) with DENV load (G4) with high juvenile survival Population growth rate data was calculated using Leslie matrix models using data from 3 replicate populations per line per treatment (same as FIG. 6) with juvenile survival estimated at 92%. Mixed effects regression model Random factors: hatch order. $Log_{10}$ copies of DENV per mosquito: Chisq = 8.38, df = 4, P = 0.0038** FDR-corrected P-value: 0.0038** | Same as 4 | | | |

TABLE 3

Primers and probes

| Target | Genomic region | Direction | 5'-3' sequence | Tm |
|---|---|---|---|---|
| Dengue virus | 3'UTR | Fw | AAGGACTAGAGG TTAGAGGAGACCC (SEQ ID NO: 11) | 54 |
| | | Rv | CGTTCTGTGCCT GGAATGATG (SEQ ID NO: 12) | 58 |
| | | Probe | FAM-AACAGCATAT TGACGCTGGGAGAG ACCAGA-BHQ1/3 (SEQ ID NO: 18) | 60 |
| *Aedes aegypti* | AAEL004175 (RPS17) | Fw | TCCGTGGTATCTC CATCAAGCT (SEQ ID NO: 13) | 60 |
| | | Rv | CACTTCCGGCACG TAGTTGTC (SEQ ID NO: 14) | 60 |
| | | Probe | FAM-CAGGAGGAG GAACGTGAGCGC AG-BHQ1/3 (SEQ ID NO:19) | |

TABLE 3-continued

Primers and probes

| Target | Genomic region | Direction | 5'-3' sequence | Tm |
|---|---|---|---|---|
| Wolbachia pipientis | WD0513 | Fw | CAAATTGCTCTTG TCCTGTGG (SEQ ID NO: 15) | 60 |
| | | Rv | GGGTGTTAAGCAG AGTTACGG (SEQ ID NO: 16) | 60 |
| | | Probe | LC640-TGAAATG GAAAAATTGGCGA GGTGTA GG-3'Iowablack RQ-Sp (SEQ ID NO: 17) | |

The disclosure has been illustrated by the previous examples. Variations and modification of the specific techniques and approaches described herein will be apparent to those skilled in the art, given the benefit of the present disclosure, and are included in the scope of this invention.

What is claimed is:

1. A method for reducing Dengue virus viral load in *Aedes aegypti* mosquitoes, the method comprising administering to the *Aedes aegypti* mosquitoes or *Aedes aegypti* mosquito larvae an RNAi agent that inhibits the expression of *Aedes aegypti* alpha-mannosidase 2 and comprises a nucleotide sequence that is complementary to a nucleotide sequence that encodes *Aedes aegypti* alpha-mannosidase 2, or an RNAi agent that inhibits the expression of *Aedes aegypti* Cadherin87A and comprises a nucleotide sequence that is complementary to a nucleotide sequence that encodes *Aedes aegypti* Cadherin87A, or administering a combination of said RNAi agents, such that exposure of the *Aedes aegypti* mosquitoes to the Dengue virus results in lower Dengue virus viral load in the mosquitoes relative to a control value for Dengue virus viral load in mosquitoes that are exposed to the Dengue virus but do not comprise the administered RNAi agent.

2. The method of claim 1, wherein the mosquitoes are infected with *Wolbachia* bacteria.

3. The method of claim 1, wherein the mosquitoes are not infected by *Wolbachia* bacteria.

4. The method of claim 1, wherein the RNAi agent comprises double stranded RNA.

5. The method of claim 1, wherein the RNAi agent that comprises the nucleotide sequence that is complementary to a nucleotide sequence that encodes *Aedes aegypti* alpha-mannosidase 2 comprises SEQ ID NO: 5.

6. The method of claim 1, wherein the RNAi agent that comprises the nucleotide sequence that is complementary to a nucleotide sequence that encodes *Aedes aegypti* Cadherin87A comprises SEQ ID NO: 6.

* * * * *

SEQUENCE LISTING

<160> NUMBER OF SEQ ID NOS: 19

<210> SEQ ID NO 1
<211> LENGTH: 2053
<212> TYPE: PRT
<213> ORGANISM: Aedes aegypti

<400> SEQUENCE: 1

Met Ile Ala Ser Thr Gln Lys Gln Gln Arg Trp Thr Val Leu Ile
1               5                   10                  15

Pro Leu Leu Thr Ile Gly Phe Leu Ile Arg Thr Cys His Cys Asn Leu
                20                  25                  30

Pro Pro Ile Phe Thr Gln Asp Met Asn Asn Leu Ala Leu Pro Glu Thr
            35                  40                  45

Thr Pro Val Gly Ser Val Val Tyr Arg Leu Glu Gly Tyr Asp Pro Glu
        50                  55                  60

Gly Gly Asn Val Ser Phe Gly Leu Leu Gly Ser Asp Asn Phe Met Val
65                  70                  75                  80

Asp Pro Ile Ser Gly Asp Val Lys Val Ile Lys Pro Leu Asp Arg Glu
                85                  90                  95

Asp Gln Asp Thr Leu Ser Phe Ser Val Thr Ile Lys Asp Arg Ile Ser
            100                 105                 110

Thr Ala Gly Ile Asp Ser Glu Asn Asp Asn Val Val Asn Val Pro Ile
        115                 120                 125

Thr Ile Ile Val Leu Asp Glu Asn Asp Asn Pro Pro Glu Phe Arg Asn
    130                 135                 140

Val Pro Tyr Glu Thr Glu Val Leu Glu Asp Ala Lys Pro Gly Thr Thr
145                 150                 155                 160

Val Phe Ser Asp Ile Leu Val Thr Asp Arg Asp Thr Val Gly Asp Asn
                165                 170                 175

Leu Ile Val Asn Cys Ile Pro Gln Pro Gln Asn Pro Asp Ala Cys Glu
            180                 185                 190

Lys Phe Ala Ile Glu Thr Leu Glu Ser Gly Gln Asp Arg Leu Thr Ala
        195                 200                 205

Ser Val Val Leu Lys Gly Arg Leu Asp Tyr Asn Glu Arg Met Ile Tyr
    210                 215                 220

Gln Ile Leu Leu Glu Ala Thr Asp Gly Met Phe Asn Ala Thr Ala Gly
225                 230                 235                 240

Leu Glu Ile His Val Lys Asp Val Gln Asn Ser Ala Pro Val Phe Gln
                245                 250                 255

```
Gly Ser Leu Ala Ala Val Ile Asn Glu Asp Ser Lys Ile Gly Thr Leu
            260                 265                 270

Val Met Met Ile His Ala Arg Asp Gly Asp Arg Gly Gln Pro Arg Lys
        275                 280                 285

Ile Val Tyr Glu Leu Val Thr Asn Pro Met Asp Tyr Phe Leu Leu Asp
    290                 295                 300

Arg Gln Thr Gly Glu Leu Arg Thr Ala Lys Pro Leu Asp Lys Glu Ala
305                 310                 315                 320

Leu Pro Asp Asp Thr Gly Leu Ile Ile Leu Thr Val Lys Ala Arg Glu
                325                 330                 335

Leu Ile Asp Gly Val Pro Gly Asn Asp Asn Leu Thr Thr Ala Thr Thr
            340                 345                 350

Gln Ala Ser Ile Thr Ile Arg Asp Val Asn Asp Ser Pro Pro Met Phe
        355                 360                 365

Asn Lys Lys Glu Tyr Phe Val Ser Leu Ser Glu Asn Thr Ala Pro Gly
    370                 375                 380

Thr Pro Leu Pro Ile Glu Met Ser Val His Asp Pro Asp Val Gly Glu
385                 390                 395                 400

Asn Ala Val Phe Ser Leu Arg Leu Asn Asp Val Ser Glu Val Phe Asp
                405                 410                 415

Val Glu Pro Lys Leu Val Thr Gly Ser Ser Gln Ile Ser Ile Arg Val
            420                 425                 430

Ala Asn Gly Ser Leu Asp Tyr Glu Asn Pro Asn Gln Arg Lys Phe Ile
        435                 440                 445

Val Leu Val Ile Ala Glu Glu Thr Gln Thr Asn Pro Lys Leu Ser Ser
    450                 455                 460

Thr Ala Thr Leu Thr Val Ser Ile Thr Asp Ser Asn Asp Asn Arg Pro
465                 470                 475                 480

Ile Phe Glu Gln Asp Ser Tyr Ser Thr Val Ser Glu Thr Ala His
                485                 490                 495

Pro Gly His Leu Ile Thr Thr Ile Thr Ala Arg Asp Leu Asp Ser Gly
            500                 505                 510

His Phe Gly Asp Gln Gly Ile Arg Tyr Ser Leu Ser Gly Thr Gly Ala
        515                 520                 525

Glu Leu Phe Asn Val Asp Pro Ile Thr Gly Ala Ile Thr Val Ala Asp
    530                 535                 540

Cys Pro Ser Val Asp Asn Asp Asn Lys Arg Arg Arg Arg Arg
545                 550                 555                 560

Gln Ile Pro Ser Ser Asp Glu Leu Thr Gln Asp Tyr Pro Asp Met Lys
                565                 570                 575

Arg Phe Asn Val Ser Thr Asp Gly Arg Ser Gly Val Leu Asp Arg Gly
            580                 585                 590

Val Asp Tyr Met Ala Tyr Lys Ile Tyr Asn Ser Gly Glu Ser Asn Glu
        595                 600                 605

Tyr Arg Asp Val Asn Val Val Ala Pro Pro Thr Val Ser Ser Ser Trp
    610                 615                 620

Glu Thr Ser Ser Leu Glu Glu Ser Asp Ser Thr Pro Ala Ile Glu Ser
625                 630                 635                 640

Glu Glu Tyr Phe Thr Pro Ser Ser Thr Thr Pro Ile His Ser Asn
                645                 650                 655

Glu Ile Gln His Arg Ser Asp Val Gly Pro Gly Arg Ala Pro Cys Leu
            660                 665                 670
```

```
Asp Tyr Glu Asn Gln Ser Val Tyr Tyr Leu Ser Tyr Lys Ala Thr Asp
            675                 680                 685

Asp Glu Gly Arg Gly Gln Thr Ser Val Val Ser Leu Arg Ile Thr Leu
690                 695                 700

Leu Asp Ala Asn Asp Ser Pro Pro Val Cys Glu Ser Pro Leu Tyr Arg
705                 710                 715                 720

Ala Ser Val Asp Glu Gly Ala Thr Leu Phe Glu Pro Pro Leu Val Ile
            725                 730                 735

Lys Ala Arg Asp Pro Asp Val Ile Ser Glu Ile Asn Tyr Arg Ile Ile
            740                 745                 750

Gly Asn Glu Ala Ile Thr Arg His Phe Glu Ile Asp Lys Arg Ser Gly
            755                 760                 765

Gln Leu Thr Ile Ser Lys Ser Thr Ala Leu Asp Val Asn His Leu Lys
770                 775                 780

Ser Glu Asn Val Phe Phe Ala Val Glu Ala Ser Asp Gly Leu Phe Thr
785                 790                 795                 800

Thr Leu Cys Asn Val Asn Ile Thr Ile Arg Asp Val Asn Asn His Ala
                805                 810                 815

Pro Gln Phe Ser Arg Glu His Tyr Leu Ala Ser Ile Glu Glu Asn Phe
            820                 825                 830

Pro Ile Gly Thr Arg Val Glu Arg Leu Gln Ala Ile Asp Leu Asp Thr
            835                 840                 845

Gly Ile Asn Ala Glu Ile Arg Tyr Arg Ile Gln Gln Gly Ser Phe Asp
            850                 855                 860

Asp Phe Ala Ile Asp Asn Gln Thr Gly Val Val Thr Ile Ala Arg Lys
865                 870                 875                 880

Leu Asp Tyr Asp Arg Arg Asn Thr Tyr Gln Met Glu Ile Val Ala Ala
                885                 890                 895

Asp Leu Gly Thr Pro Ser Leu Ser Gly Thr Thr Leu Thr Val Ser
            900                 905                 910

Ile Ile Asn Ser Asn Asp Lys Ala Pro Tyr Phe Thr Pro Thr Thr Gln
            915                 920                 925

Arg Ala Glu Ile Ser Glu Asp Ala Glu Val Gly Thr Leu Val His Thr
930                 935                 940

Leu Val Ala Leu Asp Pro Asp Val Ala Ser Ser Glu Ala Leu Asp Tyr
945                 950                 955                 960

Ala Ala Thr Glu Pro Ile Thr Ala Val Asp Lys Asp Gly Lys Glu Val
            965                 970                 975

Arg Asp Thr Glu Asp Phe Lys Asp Met Phe Arg Ile Ala Arg Thr Gly
            980                 985                 990

Lys Val Phe Val Asn Arg Lys Leu  Gln Arg Asp Asp Phe Ala Val Ile
            995                 1000                1005

Arg Ile  Thr Val Leu Val Thr  Asp Thr Thr Ala Pro  Ser Ile Gln
    1010                1015                1020

Gln Gly  Glu Gly Leu Leu Ile  Ile Thr Ile Ile Asp  Val Asn Glu
    1025                1030                1035

Glu Pro  Pro Leu Phe Val Pro  Trp Thr Pro Ala  Asp Pro Arg
    1040                1045                1050

Tyr Arg  Phe Gln Val Leu Glu  Glu Gln Pro Ile Gly  Thr Ile Leu
    1055                1060                1065

Thr Thr  Met Gln Ala Thr Asp  Ala Asp Ser Thr Val  Ala Glu Tyr
    1070                1075                1080

Arg Met  Thr Asp Asn Ser His  Phe Glu Ile Asn Asn  Thr Thr Gly
```

-continued

```
            1085                1090                1095
Leu Ile Arg Thr Lys Ala Arg Ile Asp Tyr Glu Gln Thr Pro Thr
            1100                1105                1110
Ile Gln Phe Asn Val Thr Val Val Asp Thr Gly Ile Pro Gln Leu
            1115                1120                1125
Thr Ser Thr Ala Glu Val Thr Val Asp Ile Ile Asn Thr Asn Asp
            1130                1135                1140
Asn Asp Pro Ala Phe Asp Glu Pro Glu Tyr Glu Met Ser Val Val
            1145                1150                1155
Glu Asn Ala Pro Thr Gly Thr Val Val Gly Ile Val Ser Ala Arg
            1160                1165                1170
Asp Ala Asp Ser Gly Pro Tyr Gly Gln Ile Thr Tyr Ser Leu Val
            1175                1180                1185
Gly Asp His Ser Ala Ala Ser Phe Ala Ile Asp Pro Asp Thr Gly
            1190                1195                1200
Val Ile Thr Val Arg Asp Gly Thr Thr Leu Asp Arg Glu Arg Thr
            1205                1210                1215
Thr Glu Ile Gly Leu Thr Ala Ile Ala Thr Asp Arg Ala Pro Asp
            1220                1225                1230
Gly Thr Ser Arg Ser Thr Thr Ala Pro Val Thr Ile Lys Leu Leu
            1235                1240                1245
Asp Glu Asn Asp Asn Val Pro Thr Phe Ser Gln Lys Ile Tyr His
            1250                1255                1260
Ala Thr Val Ala Glu Asn Ala Ala Leu Asn Pro Pro Ala Ala Ile
            1265                1270                1275
Leu Gln Val Leu Ala Thr Asp Pro Asp Glu Gly Ala Ala Gly Asp
            1280                1285                1290
Val Lys Tyr Ser Ile Ile Gly Ser Asp Ile Glu Asn Thr Phe Arg
            1295                1300                1305
Leu Asp Ala Asn Ser Gly Ile Leu Tyr Pro Tyr Ala Ser Leu Leu
            1310                1315                1320
Gly Leu Asp Gly Asn Tyr Arg Ile Gln Ile Glu Ala Arg Asp Gly
            1325                1330                1335
Leu Gly Ser Gly Pro His Ser Asp Arg Ala Glu Ile Lys Ile Glu
            1340                1345                1350
Ile Gln Ser Ile Asn Gln His Arg Pro Ile Phe Ile Met Pro Ala
            1355                1360                1365
Leu Ser Asn Ala Thr Val Glu Ile Pro Glu Asn Leu Ala Met Thr
            1370                1375                1380
Asp Tyr Leu Val Met Thr Val Lys Ala Asn Asp Ser Asp Glu Gly
            1385                1390                1395
Thr Asn Gly Lys Val Leu Tyr His Leu Gln Val Asn Asn Gln Asn
            1400                1405                1410
Val Gln Glu Thr Asp Glu Phe Ile Ile Asn Glu Met Ser Gly Glu
            1415                1420                1425
Leu Arg Ile Arg Lys Pro Leu Asn Arg Lys Lys Gln Ala Arg Phe
            1430                1435                1440
Glu Leu Ile Leu Val Ala Arg Asp Gln Gly Thr Pro Ala Trp Phe
            1445                1450                1455
Glu Thr Leu Arg Phe Leu Thr Val Leu Leu Val Asp Val Asn Glu
            1460                1465                1470
Asn His Pro Glu Phe Pro Asp Ala Ser Asn Pro Tyr Arg Phe Phe
            1475                1480                1485
```

-continued

```
Ile Ala Glu Asn Ser Pro Arg Asp Ile Arg Ile Gly Lys Ile Gln
    1490                1495                1500

Ala Tyr Tyr Asp Thr Pro Asp Pro Lys Ile Tyr Tyr Tyr Met Met
    1505                1510                1515

Leu Gly Asn Glu Asp Gly Ala Phe Tyr Val Asp Lys Thr Thr Gly
    1520                1525                1530

Asp Ile Tyr Thr Asn Lys Thr Leu Asp Arg Glu Glu Ala Asp Val
    1535                1540                1545

Tyr Ala Leu Tyr Ile Lys Ala Ser Lys Lys Gln Asp Leu Leu Ile
    1550                1555                1560

Thr Glu Arg Asp Arg Met Met Met Ser Thr Lys Lys Leu Glu Arg
    1565                1570                1575

Asp Ser Thr Val Ala Lys Val Trp Ile Thr Val Leu Asp Val Asn
    1580                1585                1590

Asp Asn Pro Pro Val Phe Lys Gln Asp Val Tyr Tyr Ala Gly Val
    1595                1600                1605

Ser Ser Lys Ala Ala Ile Asn Glu Leu Val Thr Ile Val Asn Ala
    1610                1615                1620

Thr Asp Arg Asp Leu Gly Val Asn Ser Thr Met Glu Leu Phe Ile
    1625                1630                1635

Ser Gly Ser Tyr Leu Tyr Lys Tyr Gly Ala Thr Lys Thr Thr Gly
    1640                1645                1650

Ser Ile Val Pro Ser Pro Phe Thr Ile Ser Lys Asp Gly Arg Ile
    1655                1660                1665

Thr Thr Ala Asn Tyr Met Ala Glu Tyr Asn Gln Asp Arg Phe Ile
    1670                1675                1680

Leu Asp Ile Val Ala Lys Glu Val Glu Ser Pro Glu Arg Val Ala
    1685                1690                1695

Thr Thr Lys Val Tyr Val Trp Ile Phe Asn Pro Glu Gln Leu Val
    1700                1705                1710

Arg Val Ile Leu Ser Arg Pro Pro Ser Glu Val His Met Glu Arg
    1715                1720                1725

Asp Glu Ile Ile Ser Glu Leu Ser Asn Ala Thr Gln Lys Leu Ile
    1730                1735                1740

Ile Val Asp Glu Ile Arg Tyr His Val Asp Ser Leu Gly Arg Ile
    1745                1750                1755

Arg Met Asp Trp Cys Asp Met Tyr Phe His Ala Ile Asp Met Ser
    1760                1765                1770

Ser Gln Thr Ile Val Ser Val Glu Glu Ile Leu Arg Glu Ile Asp
    1775                1780                1785

Ala Lys Tyr Asp Phe Leu Gln Asp Tyr Asn Ala Gly Phe Ser Ile
    1790                1795                1800

Glu Asn Val Val Pro Ala Tyr Ala Thr Asn Val Gln Asp Glu Phe
    1805                1810                1815

Asp Leu Ala Leu Ala Ala Ile Ile Ala Leu Leu Ile Val Leu Phe
    1820                1825                1830

Val Gly Ala Val Ser Phe Ile Val Leu Cys Cys Cys Leu Lys His
    1835                1840                1845

Trp Val Ile Thr Ile Pro Asn Glu Thr Arg Arg Lys Asp Ala Leu
    1850                1855                1860

Ile Lys Lys Gln Ile Ile Glu Asp Leu Asn Thr Thr Glu Asn Pro
    1865                1870                1875
```

| | | | | | | | | | | |
|---|---|---|---|---|---|---|---|---|---|---|
| Leu | Trp | Ile | Glu | Gln | Lys | Leu | Lys | Leu | Tyr | Glu | Gln | Glu | Leu |
| | 1880 | | | | 1885 | | | | 1890 | | | |

Thr Met Gln Val Phe Ser Glu Pro Glu Leu Thr Gln Gln Gln
    1895                1900                1905

Gln His His His Gln Gln Leu Asn Ser Ser Asn Asn Thr Ser
    1910                1915                1920

Ser Ser Leu Ala Ser His Gln Asn Gln His His His Val Met Gln
    1925                1930                1935

Gln Gln Glu Gln Ala Leu Val Leu Gly Leu Asp Arg Arg Asp Ser
    1940                1945                1950

Tyr Pro Glu Leu Ser Gln Gly Gly Gly Asp Asn Thr Tyr Ala Thr
    1955                1960                1965

Ile Gln Pro Arg Asn Tyr Ala Ser Asn Leu Ser Ser Val Leu Met
    1970                1975                1980

Gly Thr Ser Gly Ile Gly Gly Gly Gly Gly Gly Ser Gly Asn
    1985                1990                1995

Gly Ala Ala Pro Ala Gly Gly Leu Ser Gly Glu Met Ser Asp Tyr
    2000                2005                2010

Ala Thr Leu Arg Asn Ser Arg Ala Pro Ser Met Tyr Glu Phe Arg
    2015                2020                2025

Gly Ser Thr Phe Gln Val Gln Gln Leu Asn Gly Gly Pro Gly Gly
    2030                2035                2040

Asp Gln Pro Asp Tyr Val Thr Glu Leu Ile
    2045                2050

<210> SEQ ID NO 2
<211> LENGTH: 9594
<212> TYPE: DNA
<213> ORGANISM: artificial sequence
<220> FEATURE:
<223> OTHER INFORMATION: cDNA encoding Cadherin protein

<400> SEQUENCE: 2

```
tagcaaaacg tagctgctcc gttggttcag actacagttg acgtcgcgat ttcaacccga      60
ttggattggc ttcccttcaa tccggacaaa aactcggaag aaacgtaaac gccgcttttc     120
gaacagagca tcttggttgc ttttggggcc tcgtgaagct cgtgtcgccg gatgagagga     180
tttggaaata cagcaacaat agcaggataa tctccatatc attggttgac tatggtagct     240
cgtcatcgct gtcgctggct cactggtgag caagggagga agcgtggtgg tgaataattc     300
gataggtgca attttcacgg tgattgctcg agtggtcgat tgagaaggac tggctgggaa     360
aaccggtttt ccaccaattc agtgtcgatt gtcgaaagaa accgacaaac agtatcgttg     420
ggttcgtttt gtgtggcgga gtgggttgag tgtctgatta gaaataaaag tggaagaata     480
tcatcactgg cagttatctg taactgattc gttgcaggcg tcggtaccgc acctggctcc     540
gcgaagcaat atcagctccg ctgttgatga aagttttgct ttaagttctt cagctccaag     600
tttctgttgt tgtttgcccg gttgttgttg tcagtgctgg tgtttctccc atccccggaa     660
accggtacca ttacataaag agcaaagttc ttcgccgtac acccaaggct tgcaaccgcg     720
aacacgatgc gatgctaaat cctaagccag tcttcgaggc gttccactag gacatttgtg     780
cctccttcgg gaaagtgatc tggcgtcgtc atgaatattt tatacgcgct acgacgagtg     840
tgcttcgctt ttgcgatttc ctgtcagtct gtgcaaaaat aatatcccac tcaatacaag     900
agcagaagca aaagccccca cagtaagaaa aatagtagca aagcagcata tcataatagt     960
cgttaagaat aaagaaaata taattgaaac gtgtttccga gcgaaaaggg aaaaagtgtt    1020
```

```
gcctcggcga gagttgcaca aaaagtggag gaaattaaaa gaagctacta ttctcgtaac   1080
gaaaagccaa gaagcgtggt tggttgtgcg aaggaaaaag tgaatgattt attcagtgga   1140
tcgtctctcg ggttcgttgg aggaaacgtg taagagaaga gcagtcagca gcaaggtgaa   1200
gattgtgcga aaactgtaaa tcaagcggaa cgacgacggc gacgaatatg aatgcgaaag   1260
ttgaagtcga cggccaggtc gtcttcatca gcatcatcag agaagttgtg ggctgtagtg   1320
acgggtggtg taaagtgtag gagtctgctg gtaaagctga gttgtagtgg ttttgttttt   1380
atcaagaaag gattccaaga aagaagaaaa gaacatttaa ggagagtagt gtctttggcg   1440
tttggagctt tgccggtgcg gaacccaatt agagcagcta agaaagatt catctttcgt    1500 aattcaatat ctctaaactg aacggaagtg aactagaatt gtgtgtgtgt ggcaaggacg   1560
accaggcgac gaagcagccg ccattcagca atgatagcct ccacccagaa gcagcaacag   1620
cgatggacag ttttaatacc gctcctaacg atagggttcc tgattcggac atgtcactgc   1680
aacctgccgc cgattttcac gcaggacatg aacaacttgg ccctgccgga dacaactccg   1740
gtgggaagcg tcgtttaccg gctggagggt tacgatccgg agggcggtaa cgtctcgttt   1800
gggctgctcg gctcggacaa ctttatggtg gacccaatca gtggggacgt caaggtgata   1860
aaaccgctgg accgtgagga ccaggacacc ctctccttct cggtgaccat caaggatcgc   1920
atcagcaccg caggaatcga ttccgagaac gacaacgtgg tcaacgttcc catcacgata   1980
atcgtcctgg acgaaaacga caacccaccg gaatttcgca atgttcccta cgaaacagag   2040
gtcctggagg acgccaagcc aggcaccacc gtgttcagcg atatcctggt taccgatcgg   2100
gacaccgtcg gagataacct gatcgtgaac tgtattccac aaccgcagaa cccggatgct   2160
tgcgaaaagt tcgccatcga aaccctcgaa agcggtcagg atcgactaac ggcttcggtg   2220
gtgctgaagg gtcgcctaga ctacaacgaa cggatgatct accagattct gctggaggct   2280
accgatggga tgttcaacgc cacggctgga ctggagatcc acgtgaagga tgttcagaac   2340
agtgcgccgg tgttccaagg atcgttggcg gcggtaatca acgaggacag caagatcggg   2400
acgctggtga tgatgatcca cgcaagggat ggcgatcggg gtcaaccgag gaagattgtc   2460
tacgaattag ttacgaaccc aatggattac ttcttgctgg atcgtcaaac gggtgagcta   2520
cgcacggcca aaccactcga caaggaagcc cttcccgacg acaccgggtt gataatcctg   2580
acggttaaag ctcgcgagct gatcgacgga gttcccggta atgacaatct gaccacggca   2640
acaacacaag cgtcgatcac gattcgcgat gtgaacgatt ctccaccgat gttcaacaaa   2700
aaggaatact tcgtatcgct gtcggagaat acggctccgg gaacgccact tccgatcgaa   2760
atgagcgttc atgatccgga tgttggagag aacgctgtgt tttctctacg cttgaatgat   2820
gtttcggaag tgttcgatgt ggagccaaaa ttggtgacgg atcgtcaca gattagtatt    2880 cgtgtagcga atggttcgct ggattacgaa aaccctaacc aacggaagtt catcgtattg   2940
gtgatcgctg aagaaaccca gacgaaccct aagctgtcat cgacagctac tttaacggtg   3000
tctatcaccg actcgaatga caaccgtccg atcttcgagc aggactcgta ctctacaact   3060
gtatcggaaa ctgctcatcc cggtcatttg ataacgacca tcaccgccag agatctcgac   3120
tcaggtcatt tcgcgaccaa aggaattcgg tattccttgt ctggaacggg agccgaactc   3180
ttcaacgtcg acccgataac cggcgctata acggtcgctg attgcccatc cgtagacaac   3240
gacaacaaca aaagacgtcg tcggcgacgt cagattcctt catccgatga gctgactcaa   3300
gactacccgg atatgaaacg tttcaacgtg tcaaccgacg gacgttcggg cgtcctagac   3360
```

```
cgtggcgtag actatatggc ctacaagatc tacaacagtg gcgaatcgaa cgagtaccga    3420
gacgtgaatg tcgtcgcacc tccaacggtt tccagcagct gggaaacgtc cagtttggag    3480
gaaagcgact ccaccccggc catcgagtcg gaagaatact tcacgccatc tagcaccacc    3540
actcccatcc actcgaacga aatccagcac cgttcggatg tgggcccagg gcgagctcct    3600
tgcttggact acgaaaatca atcggtgtac tatctgtcct acaaggccac ggatgacgag    3660
ggccggggtc aaacgtcggt agtatcgctc cggatcaccc ttctggatgc gaacgattcg    3720
ccgccggtgt gcgagagccc tctctatagg gcatcggtcg acgagggagc caccctattt    3780
gagccgccgc tcgtcatcaa agcccgcgat ccggacgtta tttcggaaat taattatcgc    3840
ataattggta acgaagcaat tacgcgccat ttcgaaatcg acaaacggtc cggacagttg    3900
accatctcca agagtaccgc cctggacgtg aaccatctga agtcggaaaa cgtgttcttc    3960
gccgtggagg caagcgatgg cctcttcacc accctgtgca acgtgaacat caccatccgg    4020
gacgtgaaca accatgcacc gcagttctcc cgggagcact atcttgcctc gatcgaggag    4080
aacttcccga ttggcacccg agtcgaacgt ttacaggcaa tcgatttgga taccggcatc    4140
aacgccgaga tcaggtaccg catccagcag ggaagcttcg atgactttgc catcgacaac    4200
caaaccgggg tggtgaccat cgcccggaag ttggactacg accggaggaa cacctaccag    4260
atggaaatag tggcagcgga tctgggcacc ccaagtctgt cggggacaac caccctgacg    4320
gtgagcatca tcaatagcaa cgacaaagcc ccgtacttta cgccgactac tcagcgggcg    4380
gaaatatcgg aggatgcgga agtgggaacg ttggtccaca cgctggtggc actcgatccg    4440
gatgtggcgt ccagcgaagc gttggattat gcggcaacgg aacccatcac ggccgttgac    4500
aaggacggaa aggaggtgcg ggacacggaa gatttcaagg acatgttccg catcgatcgg    4560
accgaaaagg tgttcgtcaa tcggaagctg cagcgggatg atttgcggt gatccgaatc    4620 acggttctgg taacggacac aaccgcccca tcgattcagc agggcgaagg tctcctcata    4680
atcacaatca tcgacgtaaa tgaagagcca ccgctgttcg tgcccccgtg gactccggcg    4740
gatccccgct accggttcca ggtgctggag gaacaaccga tcggtaccat cctgacgacg    4800
atgcaagcaa cagatgccga ctcgaccgtc gccgagtacc ggatgacaga taacagccat    4860
ttcgagataa acaacacaac aggtctgatc cgcaccaaag cccgtatcga ttacgagcaa    4920
acgccaacga tccagttcaa cgtcaccgtg gtggacaccg gaatcccgca gttgacgtcc    4980
accgccgaag taacggtcga catcatcaac accaacgaca acgatccggc cttcgacgag    5040
cctgagtacg aaatgtccgt cgtggaaaac gcacccaccg gaacggttgt gggcatagtt    5100
tcagcgcggg atgccgactc gggaccgtat ggccaaatca cctactccct ggtcggtgac    5160
cacagtgctg ccagctttgc catcgatcca gacaccggag ttatcacggt gcgcgacggc    5220
acaaccttgg accgtgaacg gacaacggaa atcggcctca ctgccattgc cacggatcgg    5280
gccccggatg gaaccagccg gtcgaccacc gcaccggtta ccatcaaaact gctggacgag    5340 aacgacaatg tgccgacctt ctcgcagaag atttatcacg ccacggtagc ggaaaatgcg    5400
gcactcaatc caccggcagc aatcttgcag gttttggcca ccgatccgga cgagggcgct    5460
gctggggacg tgaaatatag catcatcggt agcgatattg aaaacacctt ccggctggac    5520
gcaaactcgg gcatcctgta tccgtacgcc agtttgctgg gactcgacgg caactatcgc    5580
atccaaatcg aggcccgcga tggcctagga tccggacctc acagcgatcg ggctgaaatt    5640
aaaattgaaa tacaaagcat caaccagcat cgtccgattt tcatcatgcc ggcactgtcc    5700
aacgcaacgg tggaaatccc cgagaattta gcgatgacgg attatctcgt gatgacggtt    5760
```

```
aaagcgaacg acagcgacga gggaacgaac ggcaaagttt tgtaccatct gcaggtcaac      5820
aaccagaacg tccaggaaac ggacgagttc atcatcaacg aaatgtccgg cgaactgcgc      5880
attcgcaagc ccctcaaccg caagaagcag gcccgcttcg agttgatcct ggtggcccgg      5940
gaccagggta cccctgcgtg gttcgaaacg ctccgtttcc tcaccgtact gctggtcgac      6000
gtcaacgaaa accacccgga gtttccggac gcctcaaacc cctacaggtt cttcatcgcc      6060
gagaacagtc ctcgggacat ccgcatcggt aaaatccagg cctattacga cacacccgac      6120
ccgaaaatct actactacat gatgctcggc aacgaggatg gagcgttcta cgtggacaaa      6180
accaccggcg atatctacac caacaaaacg ctggaccgcg aggaagcgga tgtctacgct      6240
ctctatatca aagccagcaa gaaacaagac ctgctgatca ctgagcgcga tcggatgatg      6300
atgtcgacca aaaagctgga acgcgatagc acggttgcga aggtctggat cacagtcctc      6360
gatgtcaacg acaatccccc ggtctttaaa caggacgttt actacgctgg cgtaagctcc      6420
aaggctgcca tcaacgaatt ggtgacaatt gtcaatgcga ccgatcgaga tctgggcgtg      6480
aactctacca tggaactgtt catcagcggg tcttatcttt acaaatacgg agctacgaag      6540
acaactggta gcatagttcc aagtccgttc actatttcca aggacggtcg tataactacc      6600
gcaaactaca tggccgaata taaccaggac cgtttcattc tggacattgt agcaaaagag      6660
gtggaatctc ctgagcgagt tgccaccacc aaagtctacg tctggatctt caatccagaa      6720
caactagtgc gtgtgatcct gtcgaggcca ccctcggaag ttcacatgga gcgagatgag      6780
atcatatccg aactttcgaa tgccacccag aagctgatta ttgtcgatga gattcgatac      6840
cacgtggaca gcttgggtcg cattcggatg gattggtgcg acatgtactt ccatgcgatc      6900
gatatgagtt cgcagacgat cgtgtcggta gaggagattc tgcgggagat cgacgccaaa      6960
tatgatttcc tacaggatta caatgccggc ttttcgatcg agaacgtagt cccggcctac      7020
gcaaccaacg tccaggacga gttcgatttg gccctggctg cgataatcgc cctgctgata      7080
gtgctgtttg tcggtgccgt aagcttcatc gtcctgtgct gctgtctcaa acattgggtc      7140
attacgattc cgaacgaaac cagaagaaag gacgccttga tcaaaaagca gattatcgaa      7200
gatttaaata cgaccgagaa tccactttgg atcgagcaaa aactgaagct ctacgaagag      7260
caggaactga cgatgcaagt gttttccgag ccggaactga cgcaacagca gcagcagcac      7320
caccaccaac agcagttgaa cagctcgaac aatacttcgt cgtcgttggc cagccaccag      7380
aaccagcacc accatgtgat gcaacagcag gaacaagcgt tggtcctggg gctggatcgg      7440
cgggattcgt acccggaatt gtcccaaggg ggcggcgata acacgtacgc caccatccag      7500
ccacgcaatt atgcgtccaa tctgagctcg gtgctgatgg gcactagcgg gattggtggc      7560
ggcggcggtg gcggaagcgg aaacggtgcg gccccggcag gcggactgag cggagaaatg      7620
tcggattatg cgacactgcg gaacagcagg gcaccctcga tgtacgagtt ccgaggttca      7680
accttccagg tacagcagct aaacggtgga cccggcggtg accagccaga ctacgtgacg      7740
gaactgattt aagagtaaac aaccttcgaa cagcatcgaa ccgttttgac ccaactcagc      7800
cccaaaagtg caacagtgga acaaaccgtt ttacgctctc gagatggaca gagaaagaga      7860
gagcaacatc acttttgggg tttttagcat aggatatcat caggagacta gaaagcggtt      7920
tggaatttac aaaccaaccg gaatcgccgg attgccaatt tggatttgta gaaaatgaat      7980
gctcaatgtg tatgacaccc gaatgaaata ctcaagtgaa ggaaaagttc ggaaagcgat      8040
tttttaaatt actgatgaga ggcacagatt acaaaacact ctttgataga caataaatag      8100
```

-continued

| | |
|---|---|
| gagatatctt aaaaggatag tatttatgac ggaggaagca acattgaaga gataaacgca | 8160 |
| cccggagaaa attgaatcat tccacacgcg tactcattcc gagtttaagt tgtaattaat | 8220 |
| ttaagttcac aaaaatacat taacagatga ccaccagaat cgaattcgag ctatcacgac | 8280 |
| ccgactcccc cttcatttaa aggtgctcga taggcaggga gcggacgagt ggccatttac | 8340 |
| ttcacttgga tacctcggcg gtctggggcc agcggccatt tcgagctcat tataatttct | 8400 |
| cccattttct gccaattacc aacgaacgtt cgctccacca cactctcaca cgtggtcggt | 8460 |
| accggcacgc gcttgagttc aacaaatgaa tgcaattaaa aattacgcaa aacgagattg | 8520 |
| ggggaaaaat tctgcgcacc aaaaggcatc aatgtgcaat ttttcgagag aggcaggaag | 8580 |
| aatatactga aagggataag aggtcgaatg tgtcgaaata gtcgaaatca agcattttc | 8640 |
| gaatgggttt ccctacgaaa ggcggaaatc acgaaaggct caactcgtaa aagctgaaaa | 8700 |
| tatcaaaata ctgaatggta ttcaagtctt ctctagtaaa tctagtttct agatgtcatc | 8760 |
| ttgcaattca actagcccga atgacactaa cttgcaagca tcttatccga actttatgaa | 8820 |
| cattcagctt ttttgtttc ggccttaagt tggaatcctt cggatgttac ttttctaggg | 8880 |
| ttgcacagca tccagtgaac tgacaatggc agttgaagag gcacaattta ataattttga | 8940 |
| aaattactta caaattcgtt gacataaaaa aaactccgtg agctcactag aaaattgtaa | 9000 |
| aaaatgtcgt tttgatacaa cctgtatgaa aaatttgttt taactcaaaa cttattacga | 9060 |
| gtttcaaaat caattcagtt caaatcagca tcaaacgcct catttcgttc aatactcttt | 9120 |
| cgttgagaat atttgtctac cgttcgcatt tggaatacaa ctttatgta tttcgaccta | 9180 |
| aagaccattc gacctattat cgcgatgcga acaaccccc aactgtgaag tgaatatcag | 9240 |
| cgcgtgtcgt tcgaaaaaaa aagactcaaa atccaaccg ccgacgccaa accgtcgagg | 9300 |
| tatcgagagt cgaacattgt aaataattaa atctagcaaa atggatgaga atatttaaat | 9360 |
| tattaaaaat caattatgtt aacgagttta cagagacatg cgggagggtg agggcttcga | 9420 |
| acaagggtct gagggattgc atcgccctcg ggctttagtt tcgatagcca gcctcggtgc | 9480 |
| gataaaaaag ggctcgaccg atccaattca gcgagagcgt caagagtaac tgcccatttt | 9540 |
| gtgaaaggat tgaaaagag gacgacgcta cgaaaggaca gctaccctct atcg | 9594 |

<210> SEQ ID NO 3
<211> LENGTH: 1226
<212> TYPE: PRT
<213> ORGANISM: Aedes aegypti

<400> SEQUENCE: 3

```
Met Thr Val Lys Ile Phe Arg Arg Gly Ser Ala Arg Cys Ile Gly Leu
1               5                   10                  15

Leu Ser Ala Phe Val Thr Ile Leu Leu Cys Leu Tyr Tyr Ile Ser Met
            20                  25                  30

Gly Gln Pro Ser Asn Thr Pro Thr Thr Thr Ala Thr Ser Gly Gly Ser
        35                  40                  45

Ser Leu His Lys Asp Ala Ala Leu His Gln Lys Arg Leu Ser Asn Leu
    50                  55                  60

His Ala Asp Pro His His Gly Ala Gly Ser Asn Pro Asn Ala Asn Gln
65                  70                  75                  80

Ser Trp His Ser Trp Leu Arg Asn Asn Leu Asn Ser Ile Asn Asn Gly
                85                  90                  95

Gly Asn Gly Lys Asp Arg Pro Pro Gly Leu Gly Pro Glu Val Ser Asp
            100                 105                 110
```

```
Ser Gly Gly Tyr Pro Asp Gly Asp Gly Gly Gly Val Gly Ala
            115             120             125

Ala Ala Ala Ala Val Ala Gly Ser His Pro Pro Arg Phe Ser Ala Lys
130             135             140

Trp Asp Glu Cys Val Ala Leu Glu Glu Thr Pro Thr Asp Ile Thr Thr
145             150             155             160

Gly Asp Glu Tyr Gly Asn Phe Asp Phe Gln Pro Glu Trp Met Lys Thr
            165             170             175

Lys Glu Tyr Trp Asp Lys Asp Phe Glu Ser Arg Tyr Glu Lys Leu Gln
            180             185             190

Lys Asp Pro Asn Arg Pro Pro Leu Lys Ile Val Val Pro His Ser
            195             200             205

His Asn Asp Pro Gly Trp Leu Lys Thr Phe Val Asn Tyr Phe Gln Ser
210             215             220

Asp Ser Arg Gln Ile Leu Asn Leu Ala Val Thr Lys Met Pro Glu Tyr
225             230             235             240

Asn Asn Met Ser Phe Ile Trp Ser Glu Ile Ser Phe Leu Gln Leu Trp
            245             250             255

Trp Asp Gln Ala His Pro Thr Lys Gln Arg Ile Leu Lys Lys Leu Val
            260             265             270

Lys Ser Gly Arg Leu Glu Ile Thr Thr Gly Gly Trp Val Met Thr Asp
275             280             285

Glu Ala Asn Ala His Leu Tyr Ala Met Val Asp Gln Leu Ile Glu Gly
            290             295             300

His Gln Trp Val Lys Thr Asn Leu Asn Val Thr Pro Lys Ser Gly Trp
305             310             315             320

Ser Ile Asp Pro Phe Gly His Gly Ser Thr Val Pro Tyr Leu Leu Ala
            325             330             335

Ala Ser Gly Phe Glu Gly Thr Ile Ile Gln Arg Ile His Tyr Ala Trp
            340             345             350

Lys Gln Trp Phe Ala Arg His Arg Tyr Gly Asp Phe Leu Trp Ser Pro
            355             360             365

Tyr Trp Arg Thr Pro Ser Ser Gly Leu Asp Arg Lys His Thr Leu Leu
            370             375             380

Thr His Asn Met Pro Phe Asp Ile Tyr Ser Ile Lys His Ser Cys Gly
385             390             395             400

Pro His Pro Phe Ile Cys Leu Asn Phe Asp Phe Arg Lys Ile Pro Gly
            405             410             415

Glu Tyr Thr Glu Tyr Ser Ile Lys Ala Gln Phe Ile Thr Pro Glu Asn
            420             425             430

Ile Glu Ser Lys Ala Asp Leu Leu Met Glu Gln Tyr Ser Arg Thr Ala
            435             440             445

Ser Leu Phe Pro His Asn Val Ala Leu Ile Pro Val Gly Asp Asp Phe
450             455             460

Arg Tyr Asn Lys Asp Lys Glu Met Glu Gln Gln Tyr Thr Asn Tyr Lys
465             470             475             480

Lys Leu Ile Asp Tyr Ile Asn Glu Asn Arg Asn Lys Tyr Lys Ala Glu
            485             490             495

Ile Ser Phe Gly Thr Pro Lys Asp Tyr Phe Asn Ala Ile Lys Glu Arg
            500             505             510

Tyr Asp Lys Phe Pro Thr Leu Lys Gly Asp Phe Phe Val Tyr Ala Asp
            515             520             525

Ile Phe Asn Glu Gly Arg Pro Ala Tyr Trp Ser Gly Tyr Phe Thr Thr
```

-continued

```
                530                 535                 540
Arg Pro Tyr Tyr Lys Ile Leu Ser Arg Glu Leu Glu His Asn Leu Arg
545                 550                 555                 560

Ser Leu Glu Ile Leu Phe Thr Leu Ala Phe Asn Arg Ala Arg Gln Ala
                565                 570                 575

Gly Asn Ser Asn Ala Phe Lys Ile Tyr Glu Lys Asn Tyr Glu Lys Met
                580                 585                 590

Ile Leu Ala Arg Arg Asn Leu Gly Leu Phe Gln His His Asp Ala Ile
                595                 600                 605

Thr Gly Thr Ser Lys Ala Asn Val Met Arg Asp Tyr Ala Leu Arg Leu
                610                 615                 620

Phe Glu Ser Ile Gln Asp Ser Val Lys Leu Gln Glu Lys Thr Ile Glu
625                 630                 635                 640

Leu Leu Val Gln Lys Lys Gly Thr Glu His Asn Phe Leu Ile Gly Glu
                645                 650                 655

Leu Glu Arg Asp Asn Phe Ser Lys Leu Pro Arg Lys Thr Pro Leu Ile
                660                 665                 670

Val Thr Glu Ala Arg Ser Thr Asp Phe Val Val Tyr Asn Ala Leu Ala
                675                 680                 685

Gln Glu Arg Ile Glu Val Val Leu Ile Arg Thr Leu Thr Pro Arg Val
                690                 695                 700

Lys Ile Leu Asp Pro Lys Gly Asn Pro Met Asn Ile Gln Ile Asn Pro
705                 710                 715                 720

Val Trp Asn Ile Thr Glu Thr Ser Ser Tyr Ala Ser Arg Lys Ile Ile
                725                 730                 735

Pro Ser Asp Lys Glu Tyr Glu Ile Met Phe Val Ala Lys Leu Ala Pro
                740                 745                 750

Leu Ser Leu Thr Thr Phe Thr Ala Thr Tyr Asp Asp Glu Phe Lys Pro
                755                 760                 765

Lys Met Ala Thr Leu Tyr Cys Asn Glu Cys Gln Asp Glu Lys Asn Glu
                770                 775                 780

Ile Phe Glu Ile Arg Asn Lys Gln Pro Gly Asp Ile Gln Leu Glu Asn
785                 790                 795                 800

Phe Lys Met Arg Leu Leu Phe Asp Glu Gln Ser Gly Phe Leu Lys Ser
                805                 810                 815

Val Thr Lys Lys Asn Met Gly Lys Gln Ile Gln Cys Ala Ile Lys Phe
                820                 825                 830

Ala Ala Tyr Lys Ser Ala Gln Phe His Ser Gly Ala Tyr Leu Phe Lys
                835                 840                 845

Thr Asp Pro Glu Gln Arg Asn Ser Lys Glu Ile Leu Glu Gln Tyr
850                 855                 860

Asn Asp Met Thr Ile Leu Ile Thr Ser Gly Pro Leu Ala Ser Asp Val
865                 870                 875                 880

Thr Ala Ile Tyr Gly Pro Phe Leu Ala His Thr Val Arg Ile Phe Asn
                885                 890                 895

Ser Asn Thr Val Leu Asp Asn Gly Ile Phe Ile Glu Asn Asp Ile Asp
                900                 905                 910

Phe Glu Met Pro Pro Lys Asn Arg Glu Thr Glu Leu Phe Met Arg Phe
                915                 920                 925

Val Thr Asp Ile Glu Asn Gly Ala Ser Glu Asn Pro Glu Phe Phe Ser
                930                 935                 940

Asp Leu Asn Gly Phe Gln Tyr Gln Lys Arg Val Lys Val Pro Ser Ile
945                 950                 955                 960
```

Gly Ile Glu Gly Asn Tyr Phe Pro Ile Thr Ser Gly Ala Phe Ile Gln
            965                 970                 975

Asp Asp Lys Met Arg Leu Thr Leu Leu Thr Thr His Ala Gln Gly Ala
        980                 985                 990

Ala Ser Leu Glu Pro Gly Gln Leu Glu Val Met Leu Asp Arg Arg Thr
    995                1000                1005

Leu Tyr Asp Asp Tyr Arg Gly Met Gly Glu Gly Val Val Asp Ser
   1010                1015                1020

Arg Leu Thr Arg His Arg Phe Trp Val Val Leu Glu Asn Ile Glu
   1025                1030                1035

Ser His Ser Pro Pro Leu Ala Glu Asn Pro Pro Gly Pro Ala Asp
   1040                1045                1050

Glu Pro Lys Pro Ala Glu Phe Gln Leu Pro Ser Ile Phe Ala Asn
   1055                1060                1065

Gln Leu Thr Asn Gly Leu Asn Tyr Pro Ala Asn Leu Phe Ile Val
   1070                1075                1080

Glu Lys Tyr Asp Glu Ser Asn Gln Ile Glu Leu Asn Arg Ala Val
   1085                1090                1095

Gln Leu Leu Ala Ala Pro Phe Pro Cys Asp Leu His Ile Leu Asn
   1100                1105                1110

Leu Arg Thr Leu Thr Glu Gly Asn Leu Pro Leu Phe Pro Ser Ser
   1115                1120                1125

Gly Ala Leu Leu Val Leu His Arg Gln Gly Tyr Asp Cys Arg Ile
   1130                1135                1140

Gly Gly Glu Glu Val Val Asn Tyr Phe Cys Asn Asn Ser Ser Ser
   1145                1150                1155

Ser Val Ser Leu Ser Ser Asn Ser Asn Asn Tyr Lys Asn Val Asp
   1160                1165                1170

Lys Tyr Asn Ser Arg Leu Gln Leu Phe Gly Gly Val Gln Ile Glu
   1175                1180                1185

Gln Ile Thr Gly Thr Ser Leu Thr Gly Leu His Pro Gly Ala Pro
   1190                1195                1200

Val Arg Ser Val Gly Asp Ile Phe Leu Glu Pro Met Glu Leu Arg
   1205                1210                1215

Thr Phe Asn Leu Thr Phe Val Lys
   1220                1225

<210> SEQ ID NO 4
<211> LENGTH: 7138
<212> TYPE: DNA
<213> ORGANISM: artificial sequence
<220> FEATURE:
<223> OTHER INFORMATION: sequence of cDNA encoding alpha mannidose

<400> SEQUENCE: 4
cactacaccg cctcgccatt gcattttgga ccgtggaaag ccggatcggg gatctaatct      60
tgatgtagcc gattacctcc acaccgtacc cacaaaaagg atcgcccgag tagaagaaca     120
cttgaacgtg gccagcagca gcagcttaga cgtcgccatc atctattcga agaacaaaaa     180
tcctagaaaa tgtaattttc attccaccgg caagaccaaa gtgaattaaa ctgaactccc     240
ccggatgtga agtcctgttt tagcttgttg tgtgagtgtt tgtgtgtcag aagacagagg     300
aaaaatcata aagtgtcaca ttctaccgtg agtgaaacgt gaaagccgca tcggcaccca     360
taaatgagtg aatatcgcgc gccgaaagtt tagggtggaa aattgcaccg agttggtggg     420

-continued

```
gtgctgcttc ctgtttattg ccccataatc aagtgccgag ggagcagaag cagaaaaaag    480
gtgcctgcag cgccgcagca tcatgaccgt gaaaattttc cgccggggtt cggcccgctg    540
catagggctc ctgtcggctt cgtaaccat tttgctgtgc ttgtactaca tctcgatggg    600
acagccatca acacgccaa cgacgaccgc cacttccggt ggctcctcgc tccacaagga    660
tgctgccctg caccagaaac gattaagcaa ccttcatgca gatccgcacc acggcgccgg    720
gagcaatccg aatgcaaacc aatcctggca cagttggctg cggaacaatc tcaattcgat    780
caacaacggt ggcaacggca aggatcgacc gcccggcctg ggaccggaag tgtccgacag    840
tggaggctac ccggatggtg atgggggtgg aggtggtgtc ggggctgctg ctgcagcagt    900
ggccggaagt catccgcctc ggttcagcgc caagtgggac gaatgtgtcg cactggagga    960
aaccccaacc gatatcacca ccggcgatga gtatggaaat ttcgacttcc agcccgaatg   1020
gatgaaaaca aaggaatact gggacaagga cttcgagagc cgttacgaga agctgcagaa   1080
ggatccgaac cgaccccgt tgaagattgt ggtagttccg cactcccata atgaccccgg   1140
gtggttgaag accttcgtca actacttcca gtcggattcg aggcagattc tgaacttggc   1200
cgtcactaag atgcccgagt acaacaacat gtcgtttata tggagtgaga tcagcttttct  1260 gcagttatgg tgggatcaag cacatcccac caagcagagg atattgaaaa agttggtgaa   1320
atcaggtcgt ttggagatca ctactggagg ctgggtcatg acggatgaag cgaatgctca   1380
tctttatgcg atggttgatc agcttattga aggtcatcaa tgggtcaaaa ccaatctgaa   1440
cgtaactccg aagagcggat ggagtataga tccttttgga catggtagta ccgtcccata   1500
cttgttagca gcaagtggtt ttgaaggaac catcatccaa cggatacact acgcgtggaa   1560
gcaatggttc gcccgtcatc gatacggaga tttcctgtgg agtccctact ggcgaacacc   1620
ttctagtggt ctggatcgaa agcacactct cctgactcat aacatgccct tcgacatcta   1680
ctcaatcaaa cattcctgcg ggccacatcc attcatctgc cttaatttcg acttccgcaa   1740
gattcctggc gagtatactg aatactcgat caaagctcag ttcatcacac cggaaaacat   1800
cgaatccaaa gctgaccttc tcatggagca atactcgcgt actgcttccc tgttccctca   1860
caatgtggca ctgattcccg ttggagacga tttccgttac aacaaggata agaaatgga   1920 gcaacagtac accaactaca agaagctgat cgactatatc aacgagaacc gcaacaagta   1980
caaggcggaa atcagctttg gtactccgaa ggactacttc aatgccatca ggaacgcta   2040 cgataaattc ccgactttga aggagactt tttcgtctac gcagacatct tcaacgaagg   2100
gcgtccagca tactggtctg atatttcac cacccgaccg tattacaaga ttctcagtcg   2160
agaactcgaa cacaaccttc gtagcttgga aattctgttc accttggctt caaccgagc   2220 caggcaagct ggtaattcca atgccttcaa gatctacgaa agaactacg agaagatgat   2280 ccttgctagg cggaacctag ccttttccca acatcacgat gccatcaccg aacgtccaa   2340 agccaatgtg atgcgagact acgctctgag gctgtttgaa agcatccaag actccgtcaa   2400
gcttcaagag aaaaccatag aactgctcgt ccagaagaaa ggcaccgagc acaactttct   2460
gatcggagag ctggagcggg ataacttcag caaactccct cggaagactc ctctgatcgt   2520
cacggaagca cggagtacgg acttcgtggt ctacaacgcc ctcgcgcaag aacggataga   2580
agtcgttctg atcagaacac tgaccccgcg cgttaaaatt ctcgatccga aggtaaccc   2640 aatgaacata caaatcaacc cggtgtggaa catcacggaa acttcatctt acgcatcccg   2700
gaagatcatt ccctcggaca aggagtacga aatcatgttt gtggcgaagc tggcacctct   2760
ttcgctaacg accttacgg ccacctatga cgacgagttc aaaccgaaga tggcaacgct   2820
```

```
gtactgcaac gagtgccaag atgagaaaaa tgagatattc gagatccgga acaaacaacc    2880
gggcgacatt cagctggaaa acttcaaaat gaggctgttg tttgatgagc agagcggttt    2940
cttgaagtcc gtgactaaga aaaacatggg taagcaaatt cagtgcgcga tcaagtttgc    3000
cgcgtacaag agtgcgcagt tccactctgg tgcgtatctg ttcaagacgg atccggagca    3060
aaggaattca gagaaagaga tactagagca gtataatgac atgacaattc tgataacttc    3120
cggcccactg gcaagtgacg ttacagcaat ctacggacca ttcctggctc acaccgtgcg    3180
gatattcaac tccaacacgg tgctggataa cggaatcttc atcgagaatg acatcgactt    3240
tgagatgcct ccaaagaaca gggaaacaga actgtttatg cgttttgtga cagacattga    3300
gaatggggct agcgaaaacc ctgaattctt ctcagatctt aatggattcc agtatcagaa    3360
gcgagtgaag gtcccatcga tcggtatcga gggcaactac ttccctatca ccagcggggc    3420
attcattcaa gatgataaga tgaggctaac tttgctcacg acccacgctc aaggcgctgc    3480
cagcttggaa cccggacagc tggaagtaat gctcgatagg cgaactctgt acgacgacta    3540
tcgtggtatg ggagaaggcg ttgtggacag tcgcctgacc cgacatcgat tctgggttgt    3600
tctagagaat attgaatccc attcgccacc gttagctgag aaccctccgg ggccagctga    3660
cgaaccaaaa cccgccgaat tcaactgcc tagtatattt gccaatcagc tcaccaacgg    3720
gctcaactat ccgccaatc tgttcatcgt ggaaaagtac gacgaaagta accagataga    3780
gctgaaccgg gcggtccaac tgctggccgc tccgttcccc tgtgatctcc acattctgaa    3840
tctccgaacc ctaaccgagg gtaacctgcc cctgtttccg tcgagcggag ctctgctggt    3900
tctacaccgg caaggctacg actgccggat aggtggcgaa gaagtagtaa attattttg    3960 taacaatagt agtagtagcg taagtcttag tagtaatagt aacaattaca aaatgtagaa    4020
taagtacaat agccggctgc agctctttgg tggggtgcag atcgaacaaa ttaccggcac    4080
gtcgttaacg ggtttgcacc cggggcaccg ggtgcgttcc gtgggggaca ttttccttga    4140
accgatggaa ctgcggacgt tcaacctgac gttcgtcaag tgagaagggg agagcggtgg    4200
cggtggcgaa gagacatcaa gcgaaaggct tccactgggt tcctggtttt ggattggttt    4260
tagaaagttg ttacaaaggt ggtccttgga tagttggctg ggaatcagtt cgggctaaag    4320
attggatgtc ggttttctgt ggtcacttta tggtgcttga ttttaaaata cgattgtaag    4380
attatctttc tttcatgccg ataccagatc cgagtagctg cattctttta acgtgaaggg    4440
tcggcttgac ataatttatc caggcatttg cccagaagat tatttttat ggtgctatga    4500 cctgcgccaa aatgttacga caacaaactc gattgcctct agtttcttga tcgtcccaaa    4560
cttccaaggt cctgctctac ttggtcatgc cacctaagtc ggagcgccct tccccggccg    4620
gattcgaggt gaactccatt tttggaggat ttatcacaat tacccagccc atcgtactct    4680
ttcagcattg aagactttct agatatatca agttcaccgt agagttgcgc aagctattgg    4740
ttcatacgtt tgctggcatg aatttcactc aaaaggcttc ggtgtgatgc aaacgcaata    4800
aatttttact cagacgttgt tgcaagggtt tgaacggctt gctcattggt tgattcaaac    4860
acagagtgta ataagaaaaa ctcagcaatc acagaaaaag aaaaccgtct tcgtgagtct    4920
cgtctcagtt cttaagcgtt tcctacgcat cgagataggc gattattatt cttgtcagta    4980
gcaaaccagc ccttaagcca gatttgttgc tgaaaaggaa ccgctaaaga cgttaatcgc    5040
cgacttcttg ccgaaatttc ctatagtgag ttccgtttga actgacattt cttttcaact    5100
gcgtactgcg atcagaaaaa gggctttctt gatcgatttg ttacaggcat ttcccataga    5160
```

| | |
|---|---|
| tatttaagca aatcaggctt tagcctgttt tactgctatc tgtaacgttt ttccgatggt | 5220 |
| tcatttgatg tggaaattag tttaacgggt tcaatcgccc tcgtacctat cccttgggtt | 5280 |
| caatatatgc aaagaagtat tagtgacatg acatgataga cagtcataat caacgaggga | 5340 |
| cgatgtatac atcctatagg aatacgaatt gcagagattg tgacgggaat aagtgcggtg | 5400 |
| atccttcatt aaatccgaaa tgcgaaaact gcagatatag tgcgcttatc ggacttgtag | 5460 |
| ttcagaacca ttgcatttga attttttgct cttattcatt ttactgttac tgtgcataaa | 5520 |
| ctaaagatgc tacaaataac agatatctaa gtccaaattg aaaactggca agaatgttaa | 5580 |
| ccacaaacga tgatttaacg gcctttcaaa ctggcaacac gtgtagcgtc gctgatatca | 5640 |
| tggtgaaaat gaaacatttc aggatgttct taatcactac caattaacac aacatgctga | 5700 |
| tccacgttga tatgtgggtc aagtgatatc accatagttg ggtttgaatg cttatacaac | 5760 |
| ttttgagaag gttttttgttc caacatcgat aacttttcct gtgcttgaac ttagatacta | 5820 |
| agacagcaaa tgtcaaaaat atgagtcact tgtggaaatg tcttctaagt catcgccatt | 5880 |
| tgtctctcat tgcttctaca gaaattgaat tcgatcatca agaccaagct atcaaaacca | 5940 |
| gatacggaat caaacataag aaaatacaaa cgacatcact ctcttccaag tctatccgat | 6000 |
| atgtgaatct cacaaatatt gatctgaact agggcaacaa ttttttcgaat atggttttaa | 6060 |
| gttattttat tgaaaacaaa aacagcagct gaatcatttc acacgacata gacgaatcta | 6120 |
| agcagaaccc ctcaatgtaa tcattccact tttttaagaga agaaaaaaca agaaatctgg | 6180 |
| tccagtatat attgttagat ttattattac tgaacaatgc aaaaaatccc cacaatttaa | 6240 |
| ttttatgttc gaaacaaaaa gtgcatgtac cattcaagtt ggaaagaaac ctctttgctc | 6300 |
| tgtattgtac ataccaaaat ctagcccgta gaatctcctt atctacatac ttttgtgatt | 6360 |
| atagtgttag tgatacgttt cttccctgat tcttcgattt ctgttgaaaa cttccattca | 6420 |
| tttccatcct gggtccaatt taaataccctc tatccttcac aaacgatttg ttctttcaat | 6480 |
| cacagctatg atatttaaag ttttaaccac cgtccagcag gattagttgt tgtcacataa | 6540 |
| aattccctac ttttattagt tactatttat taattaaatc taggatacccc ctaaaatagt | 6600 |
| gagcgtgcgg acgagcagct aatcccaaat gagcccctga tataaacttg tttgatatta | 6660 |
| tcctacataa taacaactac gatcaaaagc gattttacaa agaaaaaaaa agcaaagcac | 6720 |
| ctacaaggta atgcaaaaga gcaaaacaaa aaaaactagc aaaagatagt aagtaagcaa | 6780 |
| atcatcgcgt atgtttagaa aaaggattag ttgttttata aaaggaaatg aacctactgc | 6840 |
| agctagaaat taaattttaa aggaaataac ggatcaaccg agcaggaatg aacaaccata | 6900 |
| ttcttaaact agaagagaaa gaatttaact attttattgt ttattgtccc gtcgttgaat | 6960 |
| ctccgtttat tttacattga tgtctaaagc gtctgtcaga aaatgtgtga ccagttgtag | 7020 |
| taaaatttgt tttaacagt aaattaacca tttgtgcagc tcggaagttt acagttgatt | 7080 |
| tcattgcaaa aagtaatcat tacatttttt gttgcaaaat atgtattgat agaacaaa | 7138 |

<210> SEQ ID NO 5
<211> LENGTH: 649
<212> TYPE: RNA
<213> ORGANISM: artificial sequence
<220> FEATURE:
<223> OTHER INFORMATION: RNAi strand

<400> SEQUENCE: 5

| | |
|---|---|
| gggauaacuu cagcaaacuc ccucggaaga cuccucugau cgucacggaa gcacggagua | 60 |
| cggacuucgu ggucuacaac gcccucgcgc aagaacggau agaagucguu cugaucagaa | 120 |

```
cacugacccc gcgcguuaaa auucucgauc cgaaagguaa cccaaugaac auacaaauca    180
acccggugug aacaucacg gaaacuucau cuuacgcauc ccggaagauc auucccucgg    240
acaaggagua cgaaaucaug uuuguggcga agcuggcacc ucuuucgcua acgaccuuua    300
cggccaccua ugacgacgag uucaaaccga agauggcaac gcuguacugc aacgagugcc    360
aagaugagaa aaaugagaua uucgagaucc ggaacaaaca accgggcgac auucagcugg    420
aaaacuucaa aaugaggcug uuguuugaug agcagagcgg uuucuugaag uccgugacua    480
agaaaaacau ggguaagcaa auucagugcg cgaucaaguu ugccgcguac aagagugcgc    540
aguuccacuc uggugcguau cuguucaaga cggauccgga gcaaaggaau ucagagaaag    600
agauacuaga gcaguauaau gacaugacaa uucugauaac uuccggccc              649

<210> SEQ ID NO 6
<211> LENGTH: 680
<212> TYPE: RNA
<213> ORGANISM: artificial sequence
<220> FEATURE:
<223> OTHER INFORMATION: RNAi strand

<400> SEQUENCE: 6
gggacauccg caucgguaaa auccaggccu auuacgacac acccgacccg aaaaucuacu    60
acuacaugau gcucggcaac gaggauggag cguucuacgu ggacaaaacc accggcgaua    120
ucuacaccaa caaaacgcug gaccgcgagg aagcggaugu cuacgcucuc uauaucaaag    180
ccagcaagaa acaagaccug cugaucacug agcgcgaucg gaugaugaug ucgaccaaaa    240
agcuggaacg cgauagcacg guugcgaagg ucuggaucac aguccucgau gucaacgaca    300 auccccggu cuuuaaacag gacguuuacu acgcuggcgu aagcuccaag gcugccauca    360
acgaauuggu gacaauuguc aaugcgaccg aucgagaucu gggcgugaac ucuaccaugg    420
aacuguucau cagcgggucu uaucuuuaca aauacggagc uacgaagaca acugguagca    480
uaguuccaag uccguucacu auuuccaagg acggucguau aacuaccgca aacuacaugg    540
ccgaauauaa ccaggaccgu ucauucugg acauuguagc aaaagaggug gaaucuccug    600
agcgaguugc caccaccaaa gucuacgucu ggaucuucaa uccagaacaa cuagugcgug    660
ugauccuguc gaggccaccc                                               680

<210> SEQ ID NO 7
<211> LENGTH: 38
<212> TYPE: DNA
<213> ORGANISM: artificial sequence
<220> FEATURE:
<223> OTHER INFORMATION: primer

<400> SEQUENCE: 7
taatacgact cactataggg ataacttcag caaactcc                           38

<210> SEQ ID NO 8
<211> LENGTH: 37
<212> TYPE: DNA
<213> ORGANISM: artificial sequence
<220> FEATURE:
<223> OTHER INFORMATION: primer

<400> SEQUENCE: 8
taatacgact cactataggg ccggaagtta tcagaat                            37

<210> SEQ ID NO 9
```

```
<211> LENGTH: 35
<212> TYPE: DNA
<213> ORGANISM: artificial sequence
<220> FEATURE:
<223> OTHER INFORMATION: primer

<400> SEQUENCE: 9
taatacgact cactataggg acatccgcat cggta                              35

<210> SEQ ID NO 10
<211> LENGTH: 35
<212> TYPE: DNA
<213> ORGANISM: artificial sequence
<220> FEATURE:
<223> OTHER INFORMATION: primer

<400> SEQUENCE: 10
taatacgact cactataggg tggcctcgac aggat                              35

<210> SEQ ID NO 11
<211> LENGTH: 25
<212> TYPE: DNA
<213> ORGANISM: artificial sequence
<220> FEATURE:
<223> OTHER INFORMATION: primer

<400> SEQUENCE: 11
aaggactaga ggttagagga gaccc                                         25

<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12
cgttctgtgc ctggaatgat g                                             21

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
tccgtggtat ctccatcaag ct                                            22

<210> SEQ ID NO 14
<211> LENGTH: 23
<212> TYPE: DNA
<213> ORGANISM: artificial sequence
<220> FEATURE:
<223> OTHER INFORMATION: primer

<400> SEQUENCE: 14
caggaggagg aacgtgagcg cag                                           23

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15
```

-continued

```
caaattgctc ttgtcctgtg g                                             21

<210> SEQ ID NO 16
<211> LENGTH: 21
<212> TYPE: DNA
<213> ORGANISM: artificial sequence
<220> FEATURE:
<223> OTHER INFORMATION: GGGTGTTAAGCAGAGTTACGG

<400> SEQUENCE: 16
gggtgttaag cagagttacg g                                             21

<210> SEQ ID NO 17
<211> LENGTH: 28
<212> TYPE: DNA
<213> ORGANISM: artificial sequence
<220> FEATURE:
<223> OTHER INFORMATION: probe

<400> SEQUENCE: 17
tgaaatggaa aaattggcga ggtgtagg                                      28

<210> SEQ ID NO 18
<211> LENGTH: 30
<212> TYPE: DNA
<213> ORGANISM: artificial sequence
<220> FEATURE:
<223> OTHER INFORMATION: probe

<400> SEQUENCE: 18
aacagcatat tgacgctggg agagaccaga                                    30

<210> SEQ ID NO 19
<211> LENGTH: 23
<212> TYPE: DNA
<213> ORGANISM: artificial sequence
<220> FEATURE:
<223> OTHER INFORMATION: probe

<400> SEQUENCE: 19
caggaggagg aacgtgagcg cag                                           23
```